US012778998B2

(12) United States Patent
Song et al.

(10) Patent No.: US 12,778,998 B2
(45) Date of Patent: Nov. 3, 2026

(54) MESENCHYMAL STEM CELLS THAT ENABLE TUMOR TARGETING IMPROVEMENT AND VIRUS MASS-PRODUCTION

(71) Applicant: DATES BIO CO., LTD., Seoul (KR)

(72) Inventors: Jae Jin Song, Seoul (KR); Soo Jin Choi, Seoul (KR); Jeong A Hong, Seoul (KR); Hye Jin Choi, Seoul (KR)

(73) Assignee: DATES BIO CO., LTD., Seoul (KR)

(*) Notice: Subject to any disclaimer, the term of this patent is extended or adjusted under 35 U.S.C. 154(b) by 909 days.

(21) Appl. No.: 17/926,340

(22) PCT Filed: Oct. 27, 2021

(86) PCT No.: PCT/KR2021/015179

§ 371 (c)(1),
(2) Date: Nov. 18, 2022

(87) PCT Pub. No.: WO2022/092795

PCT Pub. Date: May 5, 2022

(65) Prior Publication Data

US 2023/0210927 A1 Jul. 6, 2023

(30) Foreign Application Priority Data

Oct. 27, 2020 (KR) ........................ 10-2020-0139918

(51) Int. Cl.

| | |
|---|---|
| ***C12N 15/86*** | (2006.01) |
| ***A61K 35/28*** | (2015.01) |
| ***A61K 35/761*** | (2015.01) |
| ***A61K 38/16*** | (2006.01) |
| ***A61P 35/00*** | (2006.01) |
| ***C12N 5/0775*** | (2010.01) |
| ***C12N 15/63*** | (2006.01) |

(52) U.S. Cl.

CPC ............ *A61K 35/761* (2013.01); *A61K 35/28* (2013.01); *A61K 38/162* (2013.01); *A61P 35/00* (2018.01); *C12N 5/0667* (2013.01); *C12N 15/635* (2013.01); *C12N 15/86* (2013.01); *C12N 2710/10332* (2013.01); *C12N 2710/10343* (2013.01); *C12N 2710/10352* (2013.01); *C12N 2710/10371* (2013.01)

(58) Field of Classification Search

CPC .... A61K 35/761; A61K 35/28; A61K 38/162; A61P 35/00; C12N 5/0667; C12N 15/635; C12N 15/86; C12N 2710/10332; C12N 2710/10343; C12N 2710/10352; C12N 2710/10371; C12N 2510/00; C12N 9/1276; C12N 2710/10322; C12N 2710/10032; C07K 14/005; C07K 14/705

See application file for complete search history.

(56) References Cited

U.S. PATENT DOCUMENTS

| | | | | |
|---|---|---|---|---|
| 2008/0292592 A1* | 11/2008 | Chada | .................... | C07K 14/47 435/235.1 |
| 2018/0360996 A1 | 12/2018 | Song et al. | | |
| 2021/0069253 A1 | 3/2021 | Yun et al. | | |

FOREIGN PATENT DOCUMENTS

| | | | | |
|---|---|---|---|---|
| EP | 3725875 A1 * | 10/2020 | ........... | C12N 5/0663 |
| KR | 10-2017-0067667 A | 6/2017 | | |
| KR | 10-2019-0070890 A | 6/2019 | | |
| KR | 10-2019-0139763 A | 12/2019 | | |
| KR | 20190139763 A * | 12/2019 | ........... | C12N 5/0663 |
| WO | 2019235771 A1 | 12/2019 | | |

OTHER PUBLICATIONS

Arap, M.A., Lahdenranta, J., Mintz, P.J., Hajitou, A., Sarkis, Á.S., Arap, W. and Pasqualini, R., 2004. Cell surface expression of the stress response chaperone GRP78 enables tumor targeting by circulating ligands. Cancer cell, 6(3), pp. 275-284. (Year: 2004).*

Kim, S., Yoon, Y.M., Han, Y.S., Lee, J.H., Hur, J. and Lee, S.H., 2018. Administration of Cripto in GRP 78 overexpressed human MSC s enhances stem cell viability and angiogenesis during human MSC transplantation therapy. Cell Proliferation, 51(5), p. e12463. (Year: 2018).*

Notice of Refusal of Japanese Application 2022-572629, dated Dec. 11, 2023, 12 pages.

Ullah et al. "Mesenchymal Stromal Cell Homing: Mechanisms and Strategies for Improvement", iScience, CellPress Reviews, 421-438, May 31, 2019. 18 pages.

Li et al. "Glucose regulated protein 78 promotes cell invasion via regulation of uPA production and secretion in colon cancer cells", BMB Reports. 2014; 47(8): 445-450. 2018. 6 pages.

International Searching Authority (ISA/KR). International Search Report. PCT Application No. PCT/ Issued on Jan. 28, 2022. 11 pages.

Chen, Hao, et al. "A novel adenoviral vector carrying an all-in-one Tet-On system with an autoregulatory loop for tight, inducible transgene expression." BMC biotechnology 15.1 (2015): 1-8.

Simonsen, Janne L., et al. "Telomerase expression extends the proliferative life-span and maintains the osteogenic potential of human bone marrow stromal cells." Nature biotechnology 20.6 (2002): 592-596.

Kia, Azadeh, et al. "Dual Systemic Tumor Targeting with Ligand-Directed Phage and Grp78 Promoter Induces Tumor RegressionLigand Systemic Targeting of the Grp78 Promoter." Molecular cancer therapeutics 11.12 (2012): 2566-2577.

(Continued)

*Primary Examiner* — Jeremy C Flinders
*Assistant Examiner* — Masudur Rahman
(74) *Attorney, Agent, or Firm* — Meunier Carlin & Curfman LLC

(57) ABSTRACT

The present invention relates to the preparation of mesenchymal stem cells, which are for the proliferation of viral vectors and viruses, and enable virus production and release timing control such that tumor targeting can be improved and viruses can be mass-produced. In addition, the tumorigenesis of mesenchymal stem cells of the present invention can be fundamentally blocked, safety is secured by enabling virus production and release to be controlled at desired time points, and antitumor effects can be maximized.

9 Claims, 47 Drawing Sheets

Specification includes a Sequence Listing.

(56) References Cited

OTHER PUBLICATIONS

Xia, Xi, et al. "Mesenchymal stem cells as carriers and amplifiers in CRAd delivery to tumors." Molecular cancer 10.134 (2011): 1-12.
Kerrigan, Brittany C. Parker, et al. "Mesenchymal stromal cells for the delivery of oncolytic viruses in gliomas." Cytotherapy 19.4 (2017): 445-457.
De Silva, Naomi, et al. "Double trouble for tumours: exploiting the tumour microenvironment to enhance anticancer effect of oncolytic viruses." Cytokine & growth factor reviews 21.2-3 (2010): 135-141.
Nakashima, Hiroshi, Balveen Kaur, and E. A. Chiocca. "Directing systemic oncolytic viral delivery to tumors via carrier cells." Cytokine & growth factor reviews 21.2-3 (2010): 119-126.

* cited by examiner

【FIG.1】
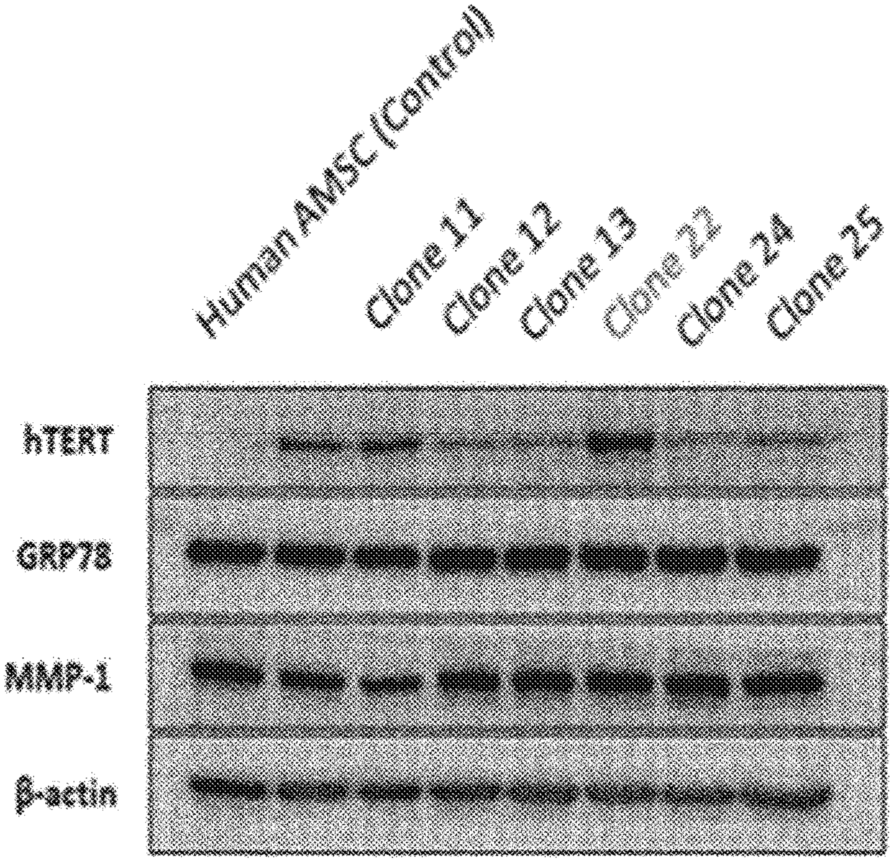
【FIG.2】
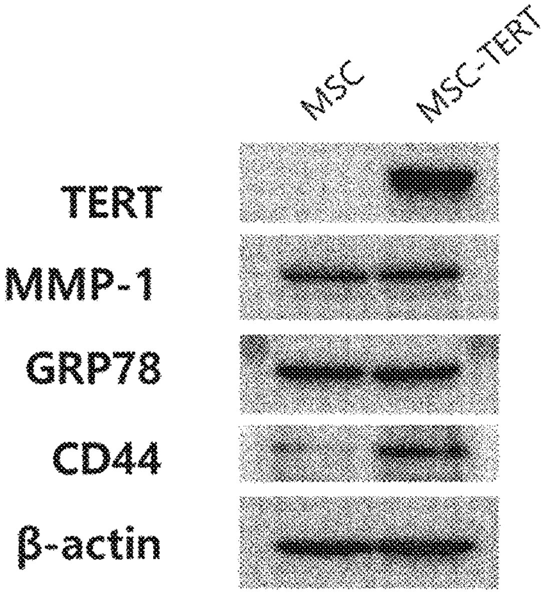

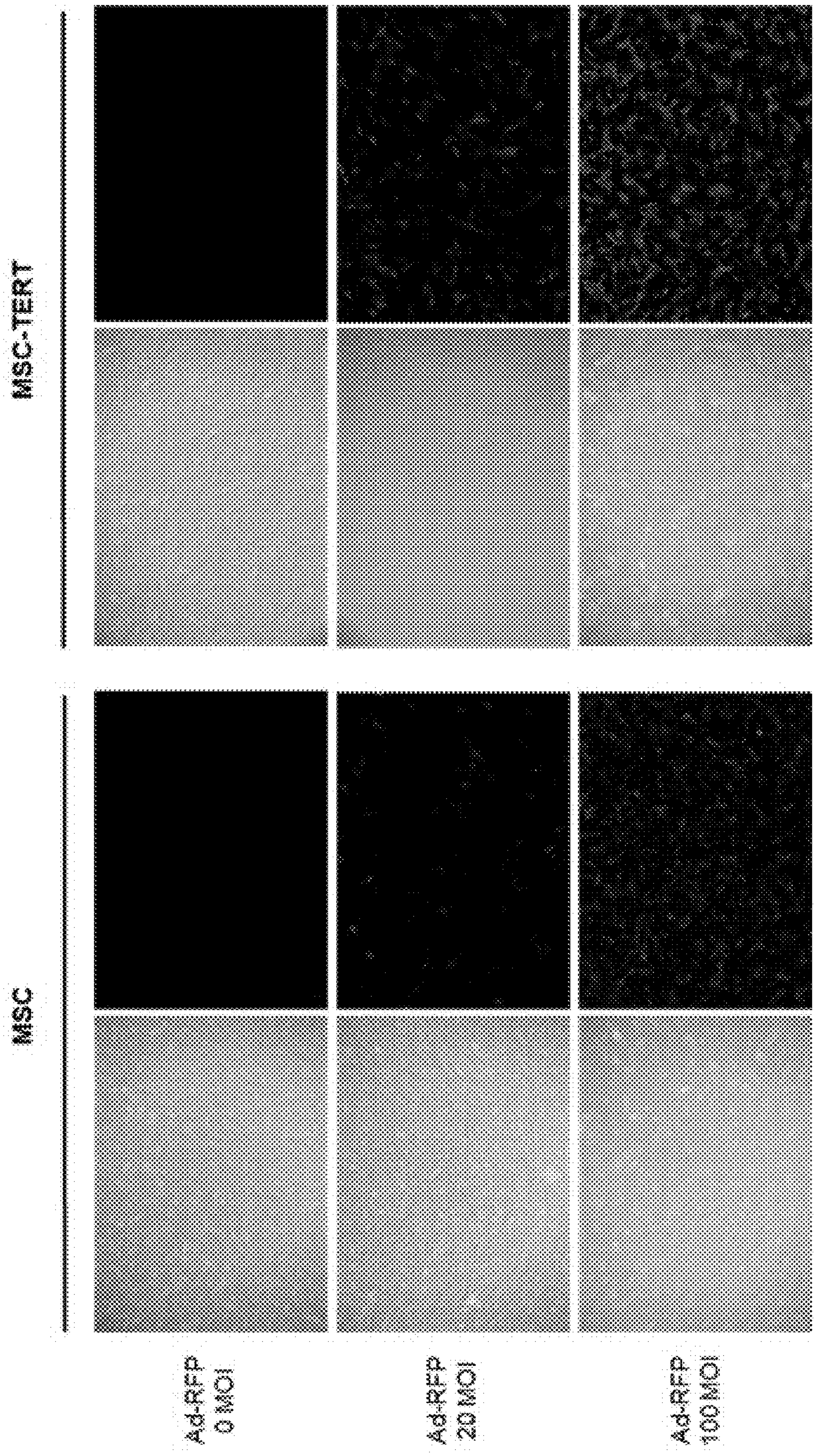
【FIG.3】

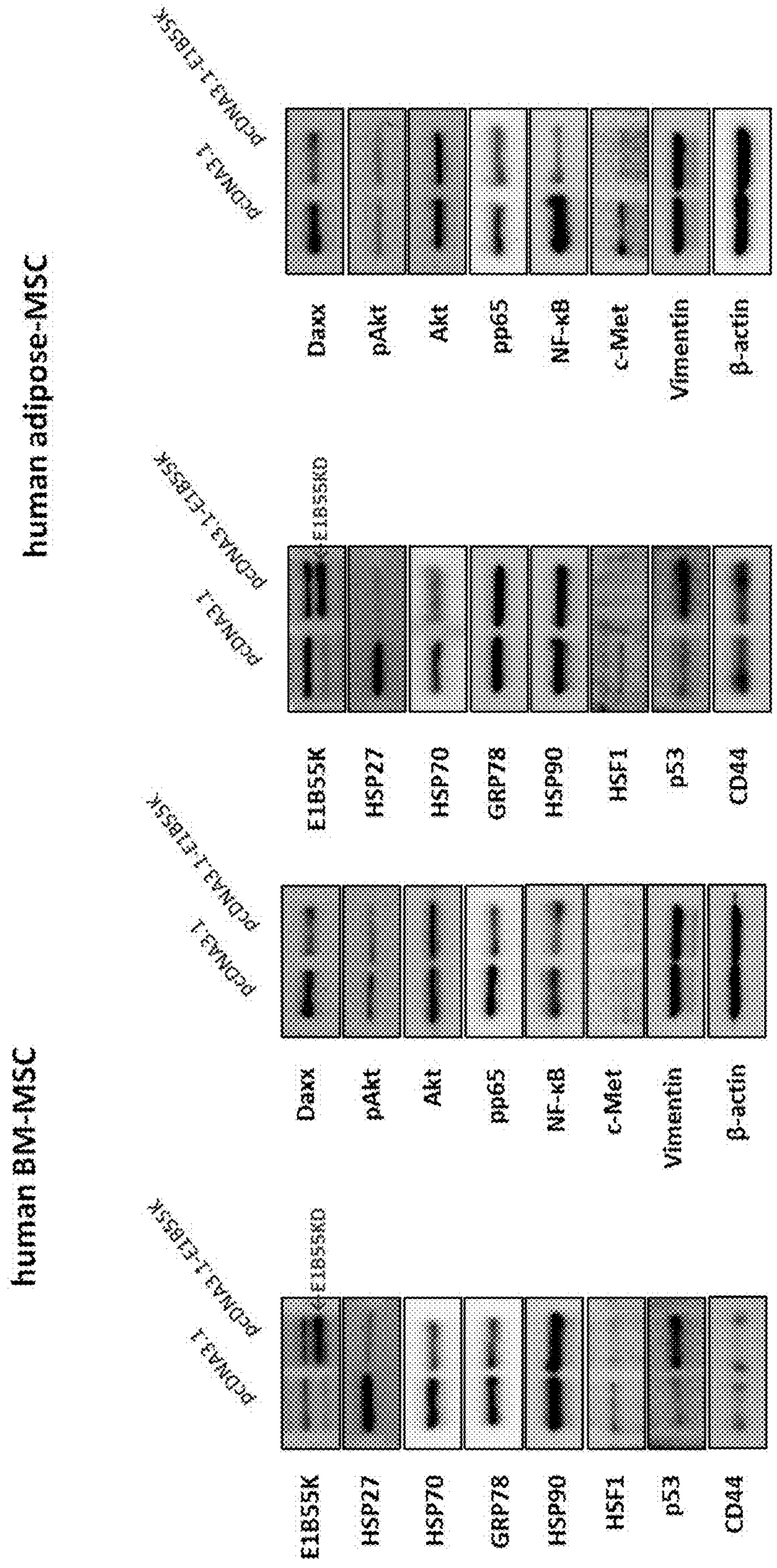
【FIG.4】

【FIG.5】
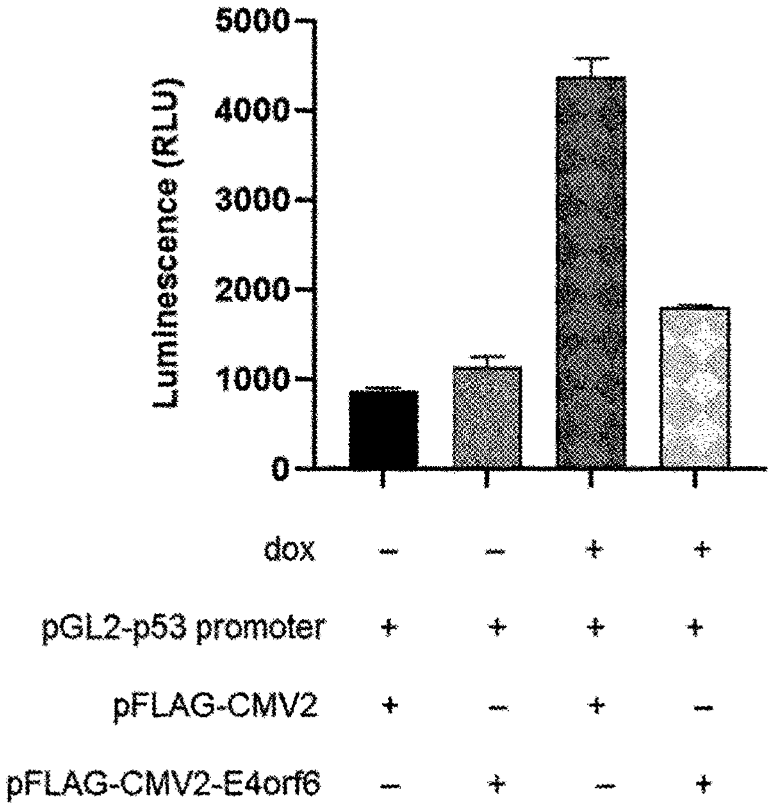
【FIG.6】
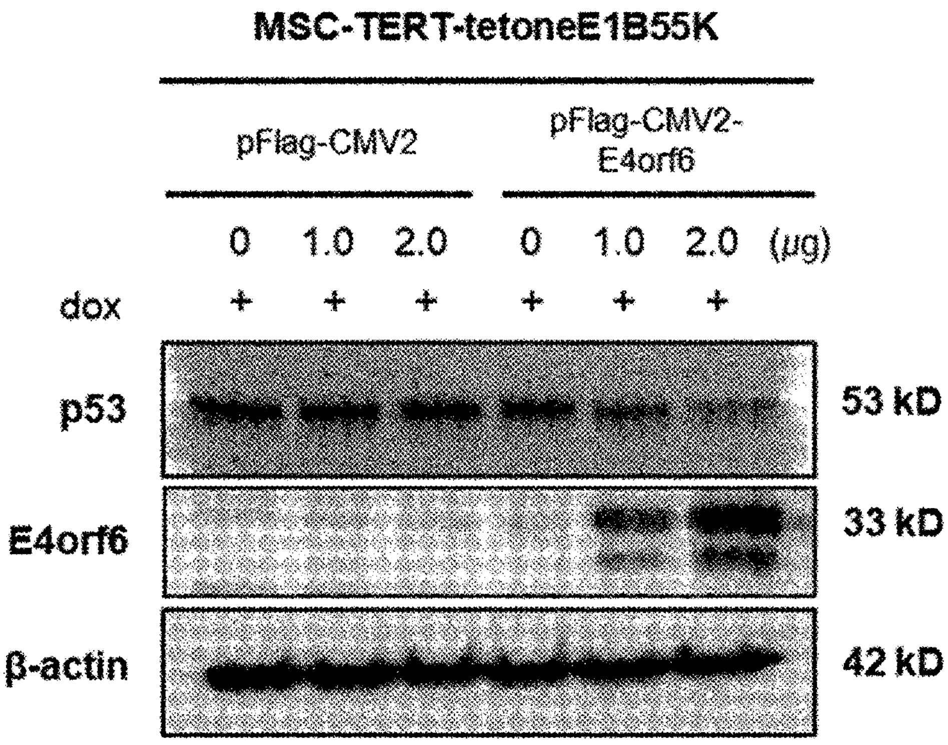

【FIG.7】

Flag tag

```
Flag-E4orf6    ------------------------GACTACAAAGACGATGACGACAAGCTTATGACTACG
sample2        AACCGTCAGAATTGATCTACCATGGACTACAAAGACGATGACGACAAGCTTATGACTACG
                                       ************************************

Flag-E4orf6    TCCGGCGTTCCATTTGGCATGACACTACGACCAACACGATCTCGGTTGTCTCGGCGCACT
sample2        TCCGGCGTTCCATTTGGCATGACACTACGACCAACACGATCTCGGTTGTCTCGGCGCACT
               ************************************************************

Flag-E4orf6    CCGTACAGTAGGGATCGTCTACCTCCTTTTGAGACAGAAACCCGCGCTACCATACTGGAG
sample2        CCGTACAGTAGGGATCGTCTACCTCCTTTTGAGACAGAAACCCGCGCTACCATACTGGAG
               ************************************************************

Flag-E4orf6    GATCATCCGCTGCTGCCCGAATGTAACACTTTGACAATGCACAACGTGAGTTACGTGCGA
sample2        GATCATCCGCTGCTGCCCGAATGTAACACTTTGACAATGCACAACGTGAGTTACGTGCGA
               ************************************************************

Flag-E4orf6    GGTCTTCCCTGCAGTGTGGGATTTACGCTGATTCAGGAATGGGTTGTTCCCTGGGATATG
sample2        GGTCTTCCCTGCAGTGTGGGATTTACGCTGATTCAGGAATGGGTTGTTCCCTGGGATATG
               ************************************************************

Flag-E4orf6    GTTCTAACGCGGGAGGAGCTTGTAATCCTGAGGAAGTGTATGCACGTGTGCCTGTGTTGT
sample2        GTTCTAACGCGGGAGGAGCTTGTAATCCTGAGGAAGTGTATGCACGTGTGCCTGTGTTGT
               ************************************************************

Flag-E4orf6    GCCAACATTGATATCATGACGAGCATGATGATCCATGGTTACGAGTCCTGGGCTCTCCAC
sample2        GCCAACATTGATATCATGACGAGCATGATGATCCATGGTTACGAGTCCTGGGCTCTCCAC
               ************************************************************

Flag-E4orf6    TGTCATTGTTCCAGTCCCGGTTCCCTGCAGTGTATAGCCGGCGGGCAGGTTTTGGCCAGC
sample2        TGTCATTGTTCCAGTCCCGGTTCCCTGCAGTGTATAGCCGGCGGGCAGGTTTTGGCCAGC
               ************************************************************

Flag-E4orf6    TGGTTTAGGATGGTGGTGGATGGCGCCATGTTTAATCAGAGGTTTATATGGTACCGGGAG
sample2        TGGTTTAGGATGGTGGTGGATGGCGCCATGTTTAATCAGAGGTTTATATGGTACCGGGAG
               ************************************************************

Flag-E4orf6    GTGGTGAATTACAACATGCCAAAAGAGGTAATGTTTATGTCCAGCGTGTTTATGAGGGGT
sample2        GTGGTGAATTACAACATGCCAAAAGAGGTAATGTTTATGTCCAGCGTGTTTATGAGGGGT
               ************************************************************

Flag-E4orf6    CGCCACTTAATCTACCTGCGCTTGTGGTATGATGGCCACGTGGGTTCTGTGGTCCCCGCC
sample2        CGCCACTTAATCTACCTGCGCTTGTGGTATGATGGCCACGTGGGTTCTGTGGTCCCCGCC
               ************************************************************

Flag-E4orf6    ATGAGCTTTGGATACAGCGCCTTGCACTGTGGGATTTTGAACAATATTGTGGTGCTGTGC
sample2        ATGAGCTTTGGATACAGCGCCTTGCACTGTGGGATTTTGAACAATATTGTGGTGCTGTGC
               ************************************************************

Flag-E4orf6    TGCAGTTACTGTGCTGATTTAAGTGAGATCAGGGTGCGCTGCTGTGCCCGGAGGACAAGG
sample2        TGCAGTTACTGTGCTGATTTAAGTGAGATCAGGGTGCGCTGCTGTGCCCGGAGGACAAGG
               ************************************************************

Flag-E4orf6    CGCCTTATGCTGCGGGCGGTGCGAATCATCGCTGAGGAGACCACTGCCATGTTGTATTCC
sample2        CGCCTTATGCTGCGGGCGGTGCGAATCATCGCTGAGGAGACCACTGCCATGTTGTATTCC
               ************************************************************

Flag-E4orf6    TGCAGGACGGAGCGGCGGCGGCAGCAGTTTATTCGCGCGCTGCTGCAGCACCACCGCCCT
sample2        TGCAGGACGGAGCGGCGGCGGCAGCAGTTTATTCGCGCGCTGCTGCAGCACCACCGCCCT
               ************************************************************

Flag-E4orf6    ATCCTGATGCACGATTATGACTCTACCCCCATGTAG------------------------
sample2        ATCCTGATGCACGATTATGACTCTACCCCCATGTAGTCTAGAGGATCCCGGGTGGCATCC
               ************************************
```

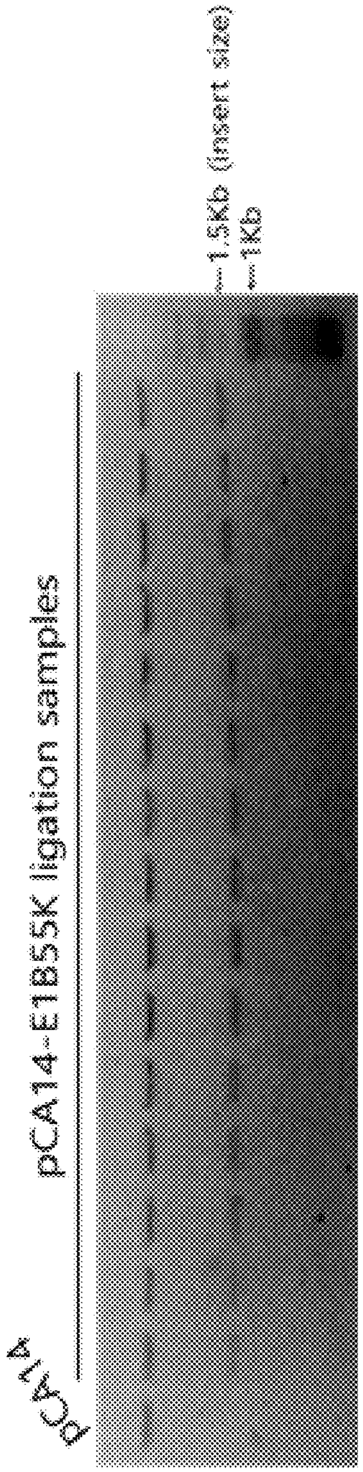
【FIG.8】

【FIG.9a】

E1B55K forward

```
E1B55K         ------------------------------------------------------------
pCA14-E1B55K   AAGACACCGGGACCGATCCAGCCTGGGGATCTTCGAGTCGAGGGATCCCTCGAGTCTAGA

E1B55K         atggagcgaagaaacccatctgagcggggggtacctgctggattttctggccatgcatct
pCA14-E1B55K   ATGGAGCGAAGAAACCCATCTGAGCGGGGAGTACCTGCTGGATTTTCTGGCCATGCATCT
               ***************************** ******************************

E1B55K         gtggagagcggttgtgagacacaagaatcgcctgctactgttgtcttccgtccgcccggc
pCA14-E1B55K   GTGGAGAGCGGTTGTGAGACACAAGAATCGCCTGCTACTGTTGTCTTCCGTCCGCCCGGC
               ************************************************************

E1B55K         gataataccgacggaggagcagcagcagcagcaggaggaagccaggcggcggcggcagga
pCA14-E1B55K   GATAATACCGACGGAGGAGCAGCAGCAGCAGCAGGAGGAAGCCAGGCGGCGGCGGCAGGA
               ************************************************************

E1B55K         gcagagcccatggaacccgagagccggcctggaccctcgggaatgaatgttgtacaggtg
pCA14-E1B55K   GCAGAGCCCATGGAACCCGAGAGCCGGCCTGGACCCTCGGGAATGAATGTTGTACAGGTG
               ************************************************************

E1B55K         gctgaactgtatccagaactgagacgcattttgacaattacagaggatgggcaggggcta
pCA14-E1B55K   GCTGAACTGTATCCAGAACTGAGACGCATTTTGACAATTACAGAGGATGGGCAGGGGCTA
               ************************************************************

E1B55K         aagggggtaaagagggagcggggggcttgtgaggctacagaggaggctaggaatctagct
pCA14-E1B55K   AAGGGGGTAAAGAGGGAGCGGGGGGCTTGTGAGGCTACAGAGGAGGCTAGGAATCTAGCT
               ************************************************************

E1B55K         tttagcttaatgaccagacaccgtcctgagtgtattacttttcaacagatcaaggataat
pCA14-E1B55K   TTTAGCTTAATGACCAGACACCGTCCTGAGTGTATTACTTTTCAACAGATCAAGGATAAT
               ************************************************************

E1B55K         tgcgctaatgagcttgatctgctggcgcagaagtattccatagagcagctgaccacttac
pCA14-E1B55K   TGCGCTAATGAGCTTGATCTGCTGGCGCAGAAGTATTCCATAGAGCAGCTGACCACTTAC
               ************************************************************

E1B55K         tggctgcagccaggggatgattttgaggaggctattagggtatatgcaaaggtggcactt
pCA14-E1B55K   TGGCTGCAGCCAGGGGATGATTTTGAGGAGGCTATTAGGGTATATGCAAAGGTGGCACTT
               ************************************************************

E1B55K         aggccagattgcaagtacaagatcagcaaacttgtaaatatcaggaattgttgctacatt
pCA14-E1B55K   AGGCCAGATTGCAAGTACAAGATCAGCAAACTTGTAAATATCAGGAATTGTTGCTACATT
               ************************************************************

E1B55K         tctgggaacggggccgaggtggagatagatacggaggatagggtggcctttagatgtagc
pCA14-E1B55K   TCTGGGAACGGGGCCGAGGTGGAGATAGATACGGAGGATAGGGTGGCCTTTAGATGTAGC
               ************************************************************

E1B55K         atgataaatatgtggccgggggtgcttggcatggacggggtggttattatgaatgtaagg
pCA14-E1B55K   ATGATAAATATGTGGCCGGGGGTGCTTGGCATGGACGGGGTGGTTATTATGAATGTAAGG
               ************************************************************

E1B55K         tttactggccccaattttagcggtacggttttcctggccaataccaaccttatcctacac
pCA14-E1B55K   TTTACTGGCCCCAATTTTAGCGGTACGGTTTTCCTGGCCAATACCAACCTTATCCTACAC
               ************************************************************

E1B55K         ggtgtaagcttctatgggtttaacaatacctgtgtggaagcctggaccgatgtaagggtt
pCA14-E1B55K   GGTGTTAGCTTCTATGGGTTTAACAATACCTGTGTGGAAGCCTGGACCGATGTAAGGGTT
               ***** ******************************************************

E1B55K         cggggctgtgccttttactgctgctggaagggggtggtgtgtcgccccaaaagcagggct
pCA14-E1B55K   CGGGGCTGTGCCTTTTACTGCTGCTGGAAGGGGGTGGTGTGTCGCCCCAAAAGCAGGGCT
               ************************************************************
```

【FIG.9b】

E1B55K reverse

```
E1B55K          tttactggccccaattttagcggtacggttttcctggccaataccaaccttatcctacac
pCA14-E1B55K    TTTACTGGCCCCAATTTTAGCGGTACGGTTTTCCTGGCCAATACCAACCTTATCCTACAC
                ************************************************************

E1B55K          ggtgtaagcttctatgggtttaacaatacctgtgtggaagcctggacccgatgtaagggtt
pCA14-E1B55K    GGTGTTAGCTTCTATGGGTTTAACAATACCTGTGTGGAAGCCTGGACCCGATGTAAGGGTT
                ***** ******************************************************

E1B55K          cggggctgtgccttttactgctgctggaagggggtggtgtgtcgccccaaaagcagggct
pCA14-E1B55K    CGGGGCTGTGCCTTTTACTGCTGCTGGAAGGGGGTGGTGTGTCGCCCCAAAAGCAGGGCT
                ************************************************************

E1B55K          tcaattaagaaatgcctctttgaaaggtgtaccttgggtatcctgtctgagggtaactcc
pCA14-E1B55K    TCAATTAAGAAATGCCTCTTTGAAAGGTGTACCTTGGGTATCCTGTCTGAGGGTAACTCC
                ************************************************************

E1B55K          agggtgcgccacaatgtggcctccgactgtggttgcttcatgctagtgaaaagcgtggct
pCA14-E1B55K    AGGGTGCGCCACAATGTGGCCTCCGACTGTGGTTGCTTCATGCTAGTGAAAAGCGTGGCT
                ************************************************************

E1B55K          gtgattaagcataacatggtatgtggcaactgcgaggacagggcctctcagatgctgacc
pCA14-E1B55K    GTGATTAAGCATAACATGGTATGTGGCAACTGCGAGGACAGGGCCTCTCAGATGCTGACC
                ************************************************************

E1B55K          tgctcggacggcaactgtcacctgctgaagaccattcacgtagccagccactctcgcaag
pCA14-E1B55K    TGCTCGGACGGCAACTGTCACCTGCTGAAGACCATTCACGTAGCCAGCCACTCTCGCAAG
                ************************************************************

E1B55K          gcctggccagtgtttgagcataacatactgacccgctgttccttgcatttgggtaacagg
pCA14-E1B55K    GCCTGGCCAGTGTTTGAGCATAACATACTGACCCGCTGTTCCTTGCATTTGGGTAACAGG
                ************************************************************

E1B55K          aggggggtgttcctaccttaccaatgcaatttgagtcacactaagatattgcttgagccc
pCA14-E1B55K    AGGGGGGTGTTCCTACCTTACCAATGCAATTTGAGTCACACTAAGATATTGCTTGAGCCC
                ************************************************************

E1B55K          gagagcatgtccaaggtgaacctgaacggggtgtttgacatgaccatgaagatctggaag
pCA14-E1B55K    GAGAGCATGTCCAAGGTGAACCTGAACGGGGTGTTTGACATGACCATGAAGATCTGGAAG
                ************************************************************

E1B55K          gtgctgaggtacgatgagacccgcaccaggtgcagaccctgcgagtgtggcggtaaacat
pCA14-E1B55K    GTGCTGAGGTACGATGAGACCCGCACCAGGTGCAGACCCTGCGAGTGTGGCGGTAAACAT
                ************************************************************

E1B55K          attaggaaccagcctgtgatgctggatgtgaccgaggagctgaggcccgatcacttggtg
pCA14-E1B55K    ATTAGGAACCAGCCTGTGATGCTGGATGTGACCGAGGAGCTGAGGCCCGATCACTTGGTG
                ************************************************************

E1B55K          ctggcctgcacccgcgctgagtttggctctagcgatgaagatacagattga---------
pCA14-E1B55K    CTGGCCTGCACCCGCGCTGAGTTTGGCTCTAGCGATGAAGATACAGATTGAAAGCTTGTC
                ***************************************************
```

【FIG.10a】
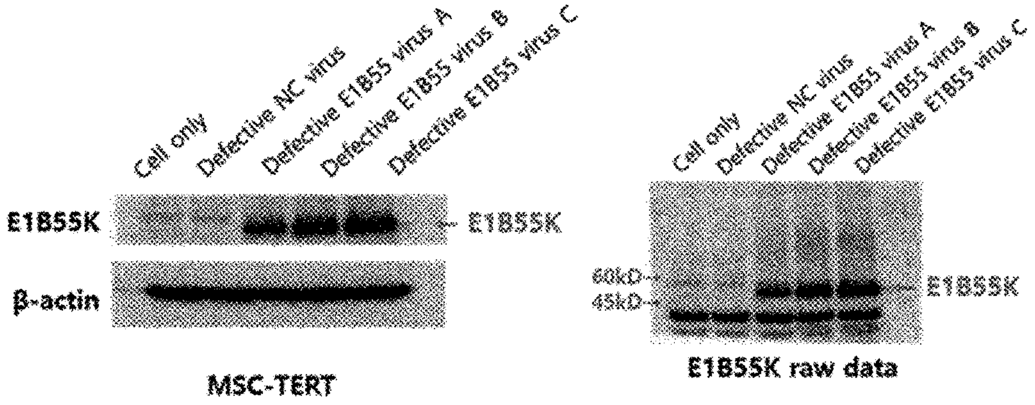
【FIG.10b】
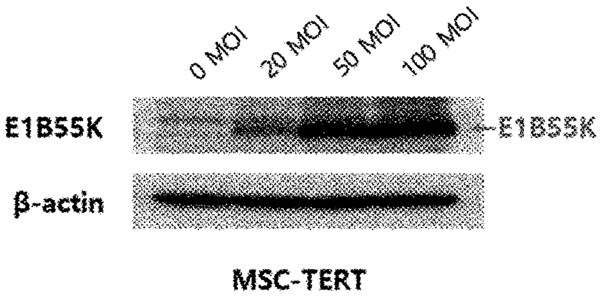
【FIG.11】
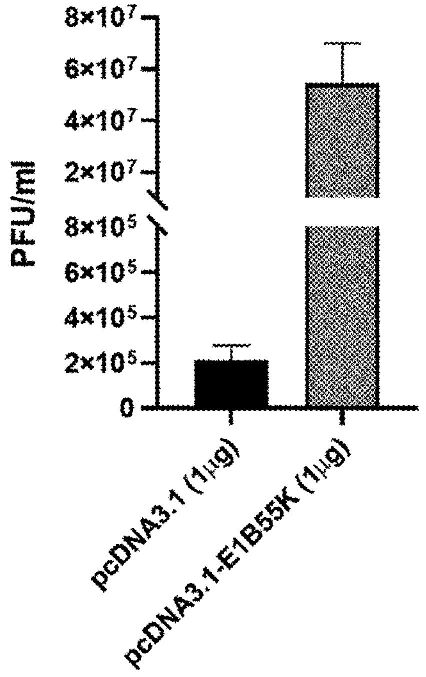

【FIG.12】
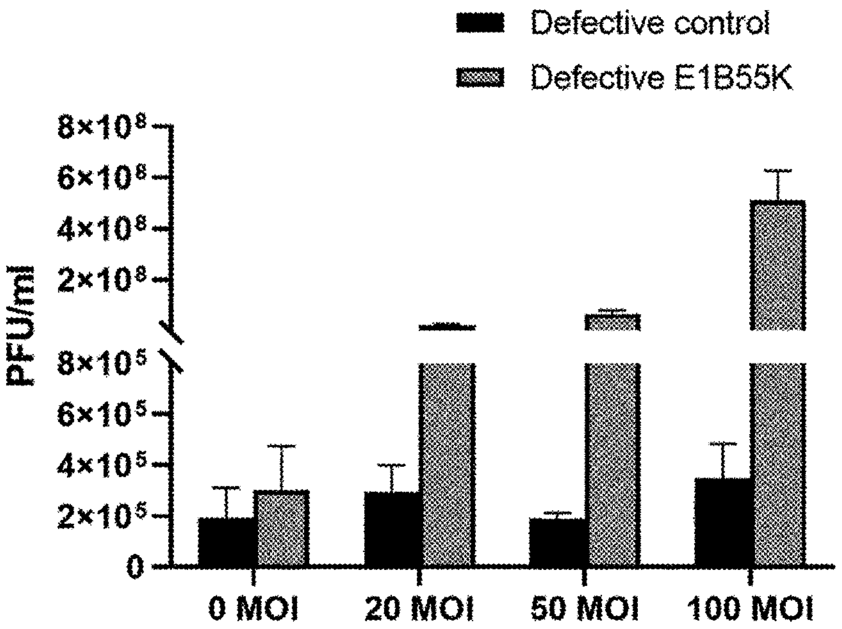

【FIG.13】

Protocol Summary

The following are the steps required to create a doxycycline-inducible expression system using retrovirus (see Figure 2).

1. Clone your gene of interest into the pRetroX-TetOne Vector using In-Fusion HD (Section V).
2. Pilot test Tet-based induction of your construct using transient transfection (Section VI).
3. Produce retroviral supernatants using the Retro-X Universal Packaging System (Section VII).
4. Transduce your target cells with TetOne virus (Section IX).

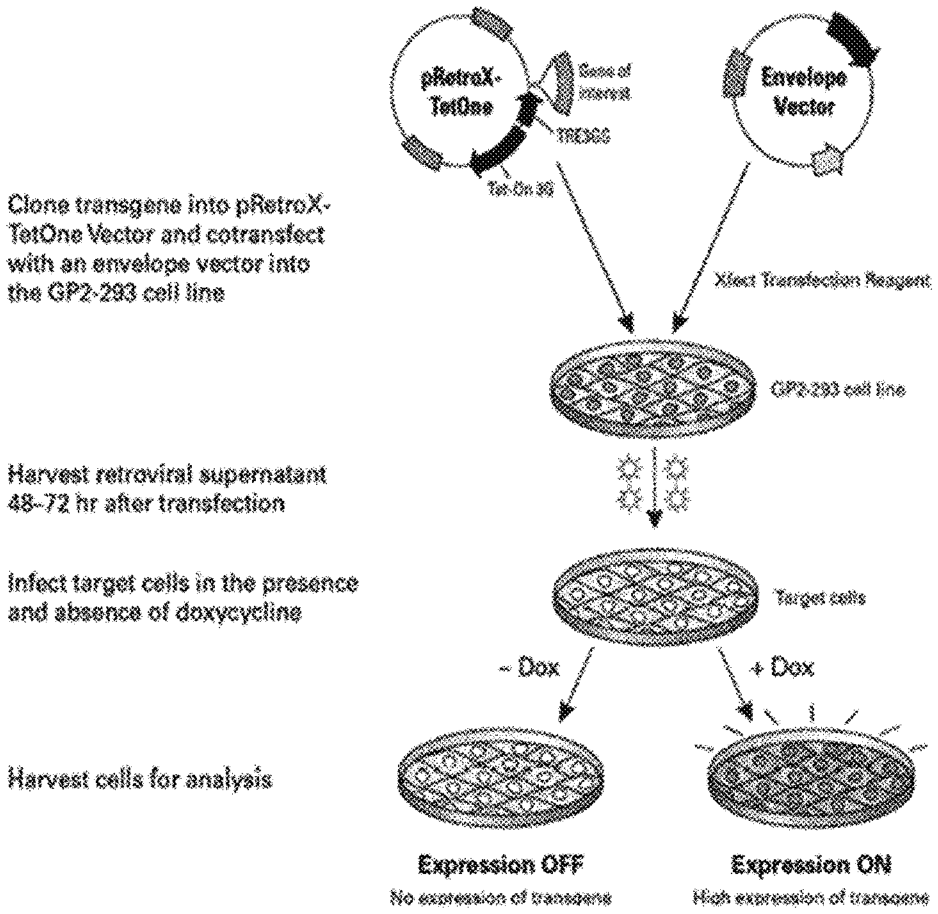

【FIG.14】
| STEP | TEMP | TIME |
|---|---|---|
| Initial Denaturation | 95℃ | 2min |
| 30 cylcle | 95℃ | 40 seconds |
| | 61℃ | 40 seconds |
| | 72℃ | 1min 50 seconds |
| Final Extension | 72℃ | 5minutes |
| | Actual amount |
|---|---|
| 2x Master Mix | 25㎕ |
| 10 μM Forward primer | 2㎕ |
| 10 μM Reverse primer | 2㎕ |
| DNA template | 1㎕ |
| DW | 20㎕ |
| Sum | 50㎕ |
【FIG.15】
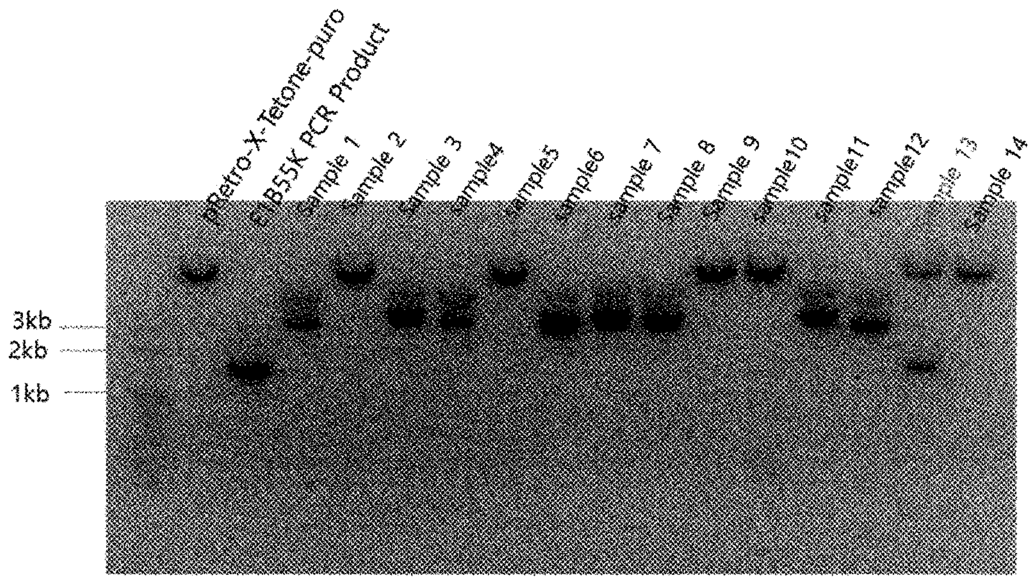

【FIG.16】
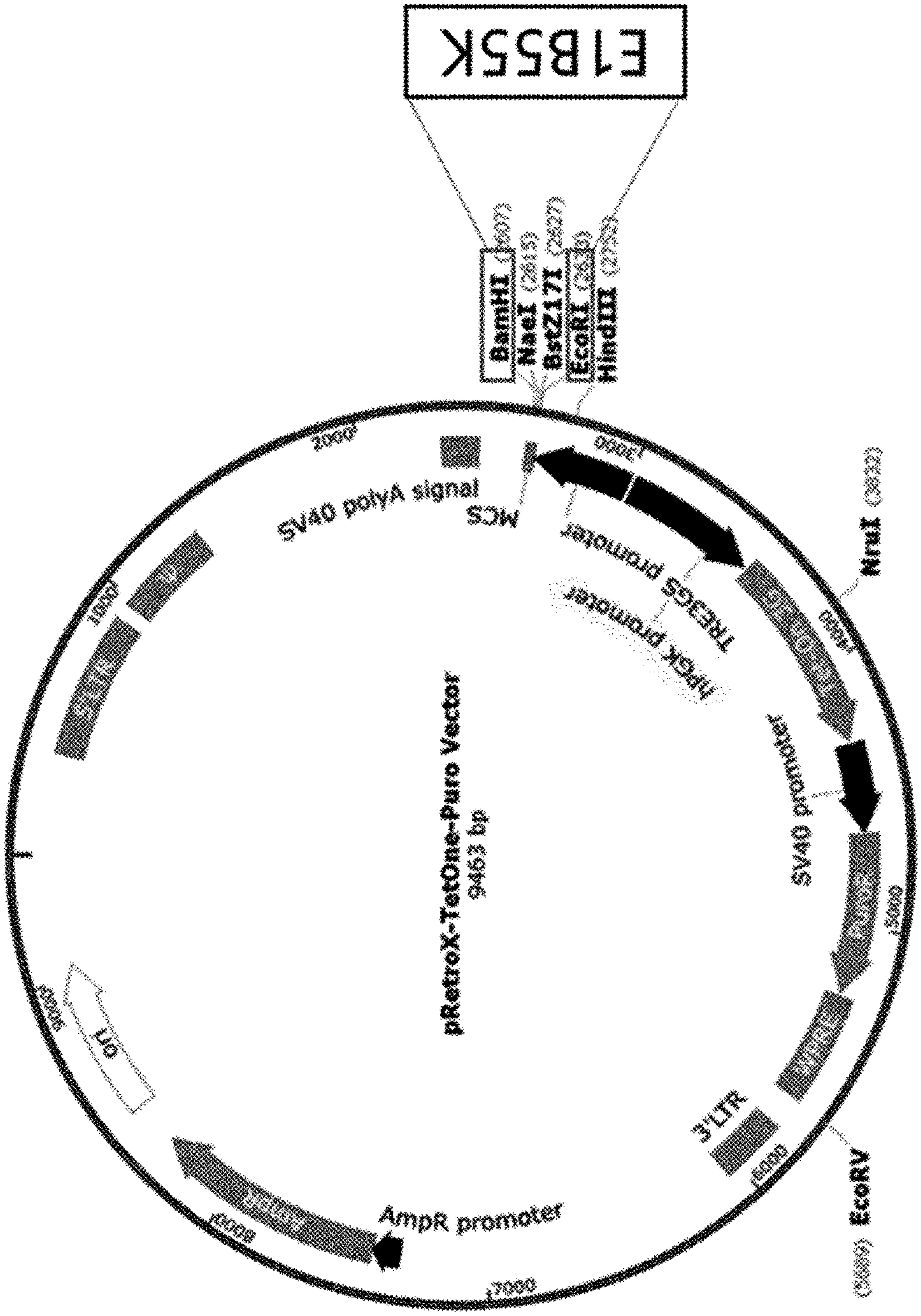

【FIG.17a】

Primer: E1B55K In-fusion EcoRI sense

```
E1B55K_sequence         atggagcgaagaaacccatctgagcggggagtacctgctggattttctggccatgcatct
sample_forward_primer   --------------------CCGGGGGGCAGTACCTGCTGGATTCTCTGGCCATGCATCT
                                               * *** *************** ***************

E1B55K_sequence         gtggagagcggttgtgagacacaagaatcgcctgctactgttgtcttccgtccgcccggc
sample_forward_primer   GTGGAGAGCGGTTGTGAGACACAAGAATCGCCTGCTACTGTTGTCTTCCGTCCGCCCGGC
                        ************************************************************

E1B55K_sequence         gataataccgacggaggagcagcagcagcagcaggaggaagccaggcggcggcggcagga
sample_forward_primer   GATAATACCGACGGAGGAGCAGCAGCAGCAGCAGGAGGAAGCCAGGCGGCGGCGGCAGGA
                        ************************************************************

E1B55K_sequence         gcagagcccatggaacccgagagccggcctggaccctcgggaatgaatgttgtacaggtg
sample_forward_primer   GCAGAGCCCATGGAACCCGAGAGCCGGCCTGGACCCTCGGGAATGAATGTTGTACAGGTG
                        ************************************************************

E1B55K_sequence         gctgaactgtatccagaactgagacgcattttgacaattacagaggatgggcaggggcta
sample_forward_primer   GCTGAACTGTATCCAGAACTGAGACGCATTTTGACAATTACAGAGGATGGGCAGGGGCTA
                        ************************************************************

E1B55K_sequence         aagggggtaaagagggagcgggggggcttgtgaggctacagaggaggctaggaatctagct
sample_forward_primer   AAGGGGGTAAAGAGGGAGCGGGGGGCTTGTGAGGCTACAGAGGAGGCTAGGAATCTAGCT
                        ************************************************************

E1B55K_sequence         tttagcttaatgaccagacaccgtcctgagtgtattacttttcaacagatcaaggataat
sample_forward_primer   TTTAGCTTAATGACCAGACACCGTCCTGAGTGTATTACTTTTCAACAGATCAAGGATAAT
                        ************************************************************

E1B55K_sequence         tgcgctaatgagcttgatctgctggcgcagaagtattccatagagcagctgaccacttac
sample_forward_primer   TGCGCTAATGAGCTTGATCTGCTGGCGCAGAAGTATTCCATAGAGCAGCTGACCACTTAC
                        ************************************************************

E1B55K_sequence         tggctgcagccaggggatgattttgaggaggctattagggtatatgcaaaggtggcactt
sample_forward_primer   TGGCTGCAGCCAGGGGATGATTTTGAGGAGGCTATTAGGGTATATGCAAAGGTGGCACTT
                        ************************************************************

E1B55K_sequence         aggccagattgcaagtacaagatcagcaaacttgtaaatatcaggaattgttgctacatt
sample_forward_primer   AGGCCAGATTGCAAGTACAAGATCAGCAAACTTGTAAATATCAGGAATTGTTGCTACATC
                        ***********************************************************
```

【FIG.17a】 (Continued)

```
E1B55K_sequence                tctgggaacggggccgaggtggagatagatacggaggatagggtggcctttagatgtagc
sample_forward_primer          TCTGGGAACGGGGCCGAGGTGGAGATAGATACGGAGGATAGGGTGGCCTTTAGATGTAGC
                               ************************************************************

E1B55K_sequence                atgataaatatgtggccgggggtgcttggcatggacggggtggttattatgaatgtaagg
sample_forward_primer          ATGATAAATATGTGGCCGGGGGTGCTTGGCATGGACGGGGTGGTTATTATGAATGTAAGG
                               ************************************************************

E1B55K_sequence                tttactggccccaatttttagcggtacggttttcctggccaataccaaccttatcctacac
sample_forward_primer          TTTACTGGCCCCAATTTTTAGCGGTACGGTTTTCCTGGCCAATACCAACCTTATCCTACAC
                               ************************************************************

E1B55K_sequence                ggtgttagcttctatgggtttaacaatacctgtgtggaagcctggaccgatgtaagggtt
sample_forward_primer          GGTGTTAGCTTCTATGGGTTTAACAATACCTGTGTGGAAGCCTGGACCGATGTAAGGGTT
                               ************************************************************

E1B55K_sequence                cggggctgtgccttttactgctgctggaagggggtggtgtgtcgccccaaaagcagggct
sample_forward_primer          CGGGGCTGTGCCTTTTACTGCTGCTGGAAGGGGGTGGTGTGTCGCCCCAAAAGCAGGGCT
                               ************************************************************

E1B55K_sequence                tcaattaagaaatgcctctttgaaaggtgtaccttgggtatcctgtctgagggtaactcc
sample_forward_primer          TCAATTAAGAAATGCCTCTTTGAAAGGTGTACCTTGGGTATCCTGTCTGAGGGTAACTCC
                               ************************************************************

E1B55K_sequence                agggtgcgccacaatgtggcctccgactgtggttgcttcatgctagtgaaaagcgtggct
sample_forward_primer          AGGGTGCGCCACAATGTGGCCTCCGACTGTGGTTGCTTCATGCTAGTGAAAAGCGTGGCT
                               ************************************************************

E1B55K_sequence                gtgattaagcataacatggtatgtggcaactgcgaggacagggcctctcagatgctgacc
sample_forward_primer          GTGATTAAGCATAACATGGTATGTGGCAACTGCGAGGACAGGGCCTCTCAGATGCTGACC
                               ************************************************************

E1B55K_sequence                tgctcggacggcaactgtcacctgctgaagaccattcacgtagccagccactctcgcaag
sample_forward_primer          TGCTCGGACGGCAACTGTCACCTGCTGAAGACATTCACGTAGCCAGCCCTTTCGCAA--G
                               ********************************  *        *   **  ** *    *

E1B55K_sequence                gcctggccagtgtttgagcataacatactgacccgctgttccttgcatttgggtaacagg
sample_forward_primer          GCTG-GCCAGG--GTTGAGCATACCTACTGACCCCCTGTTCCTTGCTTTGGGAAAAA---
                               **   *****    *       ** ********* ********** ** **   **
```

【FIG.17b】

Primer: E1B55K internal primer

```
E1B55K_sequence           ggtgttagcttctatgggtttaacaatacctgtgtggaagcctggaccgatgtaagggtt
sample_internal_primer    ----------------------------------ACCTGTAATTTGTTTATTTGGGCGTA
                                                                    *      ** *  * **

E1B55K_sequence           cggggctgtgccttttactgctgctggaagggggtggtgtgtcgccccaaaagcagggct
sample_internal_primer    GGTCGGGCGTGCTTTTACTGCTGCTGGAAGGGGGTGGTGTGTCGCCCCAAAAGCAGGGCT
                           *  *      *************************************************

E1B55K_sequence           tcaattaagaaatgcctctttgaaaggtgtaccttgggtatcctgtctgagggtaactcc
sample_internal_primer    TCAATTAAGAAATGCCTCTTTGAAAGGTGTACCTTGGGTATCCTGTCTGAGGGTAACTCC
                          ************************************************************

E1B55K_sequence           agggtgcgccacaatgtggcctccgactgtggttgcttcatgctagtgaaaagcgtggct
sample_internal_primer    AGGGTGCGCCACAATGTGGCCTCCGACTGTGGTTGCTTCATGCTAGTGAAAAGCGTGGCT
                          ************************************************************

E1B55K_sequence           gtgattaagcataacatggtatgtggcaactgcgaggacagggcctctcagatgctgacc
sample_internal_primer    GTGATTAAGCATAACATGGTATGTGGCAACTGCGAGGACAGGGCCTCTCAGATGCTGACC
                          ************************************************************

E1B55K_sequence           tgctcggacggcaactgtcacctgctgaagaccattcacgtagccagccactctcgcaag
sample_internal_primer    TGCTCGGACGGCAACTGTCACCTGCTGAAGACCATTCACGTAGCCAGCCACTCTCGCAAG
                          ************************************************************

E1B55K_sequence           gcctggccagtgtttgagcataacatactgacccgctgttccttgcatttgggtaacagg
sample_internal_primer    GCCTGGCCAGTGTTTGAGCATAACATACTGACCCGCTGTTCCTTGCATTTGGGTAACAGG
                          ************************************************************

E1B55K_sequence           aggggggtgttcctaccttaccaatgcaatttgagtcacactaagatattgcttgagccc
sample_internal_primer    AGGGGGGTGTTCCTACCTTACCAATGCAATTTGAGTCACACTAAGATATTGCTTGAGCCC
                          ************************************************************

E1B55K_sequence           gagagcatgtccaaggtgaacctgaacggggtgtttgacatgaccatgaagatctggaag
sample_internal_primer    GAGAGCATGTCCAAGGTGAACCTGAACGGGGTGTTTGACATGACCATGAAGATCTGGAAG
                          ************************************************************

E1B55K_sequence           gtgctgaggtacgatgagacccgcaccaggtgcagaccctgcgagtgtggcggtaaacat
sample_internal_primer    GTGCTGAGGTACGATGAGACCCGCACCAGGTGCAGACCCTGCGAGTGTGGCGGTAAACAT
                          ************************************************************

E1B55K_sequence           attaggaaccagcctgtgatgctggatgtgaccgaggagctgaggcccgatcacttggtg
sample_internal_primer    ATTAGGAACCAGCCTGTGATGCTGGATGTGACCGAGGAGCTGAGGCCCGATCACTTGGTG
                          ************************************************************

E1B55K_sequence           ctggcctgcacccgcgctgagtttggctctagcgatgaagatacagattga---------
sample_internal_primer    CTGGCCTGCACCCGCGCTGAGTTTGGCTCTAGCGATGAAGATACAGATTGAGGATCCAGA
                          ***************************************************
```

【FIG.17c】

TTT→TTC
Phe(Phenylalanine)

Primer: E1B55K 5' near internal reverse primer

```
E1B55_sequence            ---------atggagcgaagaaacccatctgagcggggagtacctgctggattttctggc
sample_5'_near_reverse    AAAGAATTCATGGAGCGAAGAAACCCATCTGAGCGGGGAGTACCTGCTGGATTCTCTGGC
                                   ******************************************** ******

E1B55_sequence            catgcatctgtggagagcggttgtgagacacaagaatcgcctgctactgttgtcttccgt
sample_5'_near_reverse    CATGCATCTGTGGAGAGCGGTTGTGAGACACAAGAATCGCCTGCTACTGTTGTCTTCCGT
                          ************************************************************

E1B55_sequence            ccgcccggcgataataccgacggaggagcagcagcagcagcaggaggaagccaggcggcg
sample_5'_near_reverse    CCGCCCGGCGATAATACCGACGGAGGAGCAGCAGCAGCAGCAGGAGGAAGCCAGGCGGCG
                          ************************************************************

E1B55_sequence            gcggcaggagcagagcccatggaacccgagagccggcctggaccctcgggaatgaatgtt
sample_5'_near_reverse    GCGGCAGGAGCAGAGCCCATGGAACCCGAGAGCCGGCCTGGACCCTCGGGAATGAATGTT
                          ************************************************************

E1B55_sequence            gtacaggtggctgaactgtatccagaactgagacgcattttgacaattacagaggatggg
sample_5'_near_reverse    GTACAGGTGGCTGAACTGTATCCAGAACTGAGACGCATTTTGACAATTACAGAGGATGGG
                          ************************************************************

E1B55_sequence            caggggctaaagggggtaaagagggagcggggggcttgtgaggctacagaggaggctagg
sample_5'_near_reverse    CAGGGGCTAAAGGGGGTAAAGAGGGAGCGGGGGGCTTGTGAGGCTACAGAGGAGGCTAGG
                          ************************************************************

E1B55_sequence            aatctagcttttagcttaatgaccagacaccgtcctgagtgtattacttttcaacagatc
sample_5'_near_reverse    AATCTAGCTTTTAGCTTAATGACCAGACACCGTCCTGAGTGTATTACTTTTCAACAGATC
                          ************************************************************

E1B55_sequence            aaggataattgcgctaatgagcttgatctgctggcgcagaagtattccatagagcagctg
sample_5'_near_reverse    AAGGATAATTGCGCTAATGAGCTGATCTGCGCGCAGACGCGCCAACAAAACAAGAGTCCA
                          ***********************         *  *  *    *    *   **   *
```

【FIG.17d】

Primer:E1B55K In-fusion BamHI antisense

```
E1B55K_sequence          gctgaactgtatccagaactgagacgcattttgacaattacagaggatgggcaggggcta
sample_reverse_primer    ----------------------------------------AAAGGAT--GGCAGGGCT-
                                                                  * *****  *   *****

E1B55K_sequence          aagggggtaaagagggagcgggggggcttgtgaggctacagaggaggctaggaatctagct
sample_reverse_primer    ---AAAGGGGTAAAGAGGAGCGGGGGCTTGGAGGCTACAGAGGAGGCTAGGAATCTAGCT
                               *     * *  * * ****  *  *****************************

E1B55K_sequence          tttagcttaatgaccagacaccgtcctgagtgtattacttttcaacagatcaaggataat
sample_reverse_primer    TTTAGCTTAATGACCAGACACCGTCCTGAGTGTATTACTTTTCAACAGATCAAGGATAAT
                         ************************************************************

E1B55K_sequence          tgcgctaatgagcttgatctgctggcgcagaagtattccatagagcagctgaccacttac
sample_reverse_primer    TGCGCTAATGAGCTTGATCTGCTGGCGCAGAAGTATTCCATAGAGCAGCTGACCACTTAC
                         ************************************************************

E1B55K_sequence          tggctgcagccaggggatgattttgaggaggctattagggtatatgcaaaggtggcactt
sample_reverse_primer    TGGCTGCAGCCAGGGGATGATTTTGAGGAGGCTATTAGGGTATATGCAAAGGTGGCACTT
                         ************************************************************

E1B55K_sequence          aggccagattgcaagtacaagatcagcaaacttgtaaatatcaggaattgttgctacatt
sample_reverse_primer    AGGCCAGATTGCAAGTACAAGATCAGCAAACTTGTAAATATCAGGAATTGTTGCTACATC
                         ***********************************************************

E1B55K_sequence          tctgggaacggggccgaggtggagatagatacggaggatagggtggcctttagatgtagc
sample_reverse_primer    TCTGGGAACGGGGCCGAGGTGGAGATAGATACGGAGGATAGGGTGGCCTTTAGATGTAGC
                         ************************************************************

E1B55K_sequence          atgataaatatgtggccgggggtgcttggcatggacggggtggttattatgaatgtaagg
sample_reverse_primer    ATGATAAATATGTGGCCGGGGGTGCTTGGCATGGACGGGGTGGTTATTATGAATGTAAGG
                         ************************************************************

E1B55K_sequence          tttactggccccaattttagcggtacggttttcctggccaataccaaccttatcctacac
sample_reverse_primer    TTTACTGGCCCCAATTTTAGCGGTACGGTTTTCCTGGCCAATACCAACCTTATCCTACAC
                         ************************************************************

E1B55K_sequence          ggtgttagcttctatgggtttaacaatacctgtgtggaagcctggaccgatgtaagggtt
sample_reverse_primer    GGTGTTAGCTTCTATGGGTTTAACAATACCTGTGTGGAAGCCTGGACCGATGTAAGGGTT
                         ************************************************************
```

【FIG.17d】 (Continued)

```
E1B55K_sequence          cggggctgtgccttttactgctgctggaagggggtggtgtgtcgccccaaaagcagggct
sample_reverse_primer    CGGGGCTGTGCCTTTTACTGCTGCTGGAAGGGGGTGGTGTGTCGCCCCAAAAGCAGGGCT
                         ************************************************************

E1B55K_sequence          tcaattaagaaatgcctctttgaaaggtgtaccttgggtatcctgtctgagggtaactcc
sample_reverse_primer    TCAATTAAGAAATGCCTCTTTGAAAGGTGTACCTTGGGTATCCTGTCTGAGGGTAACTCC
                         ************************************************************

E1B55K_sequence          agggtgcgccacaatgtggcctccgactgtggttgcttcatgctagtgaaaagcgtggct
sample_reverse_primer    AGGGTGCGCCACAATGTGGCCTCCGACTGTGGTTGCTTCATGCTAGTGAAAAGCGTGGCT
                         ************************************************************

E1B55K_sequence          gtgattaagcataacatggtatgtggcaactgcgaggacagggcctctcagatgctgacc
sample_reverse_primer    GTGATTAAGCATAACATGGTATGTGGCAACTGCGAGGACAGGGCCTCTCAGATGCTGACC
                         ************************************************************

E1B55K_sequence          tgctcggacggcaactgtcacctgctgaagaccattcacgtagccagccactctcgcaag
sample_reverse_primer    TGCTCGGACGGCAACTGTCACCTGCTGAAGACCATTCACGTAGCCAGCCACTCTCGCAAG
                         ************************************************************

E1B55K_sequence          gcctggccagtgtttgagcataacatactgacccgctgttccttgcatttgggtaacagg
sample_reverse_primer    GCCTGGCCAGTGTTTGAGCATAACATACTGACCCGCTGTTCCTTGCATTTGGGTAACAGG
                         ************************************************************

E1B55K_sequence          aggggggtgttcctaccttaccaatgcaatttgagtcacactaagatattgcttgagccc
sample_reverse_primer    AGGGGGGTGTTCCTACCTTACCAATGCAATTTGAGTCACACTAAGATATTGCTTGAGCCC
                         ************************************************************

E1B55K_sequence          gagagcatgtccaaggtgaacctgaacggggtgtttgacatgaccatgaagatctggaag
sample_reverse_primer    GAGAGCATGTCCAAGGTGAACCTGAACGGGGTGTTTGACATGACCATGAAGATCTGGAAG
                         ************************************************************

E1B55K_sequence          gtgctgaggtacgatgagacccgcaccaggtgcagaccctgcgagtgtggcggtaaacat
sample_reverse_primer    GTGCTGAGGTACGATGAGACCCGCACCAGGTGCAGACCCTGCGAGTGTGGCGGTAAACAT
                         ************************************************************

E1B55K_sequence          attaggaaccagcctgtgatgctggatgtgaccgaggagctgaggcccgatcacttggtg
sample_reverse_primer    ATTAGGAACCAGCCTGTGATGCTGGATGTGACCGAGGAGCTGAGGCCCGATCACTTGGTG
                         ************************************************************

E1B55K_sequence          ctggcctgcacccgcgctgagtttggctctagcgatgaagatacagattga
sample_reverse_primer    CTGGCCTGCACCCGCGCTGAGTTTGGCCCCCGT------------------
                         ************************** *  *
```

【FIG.18】
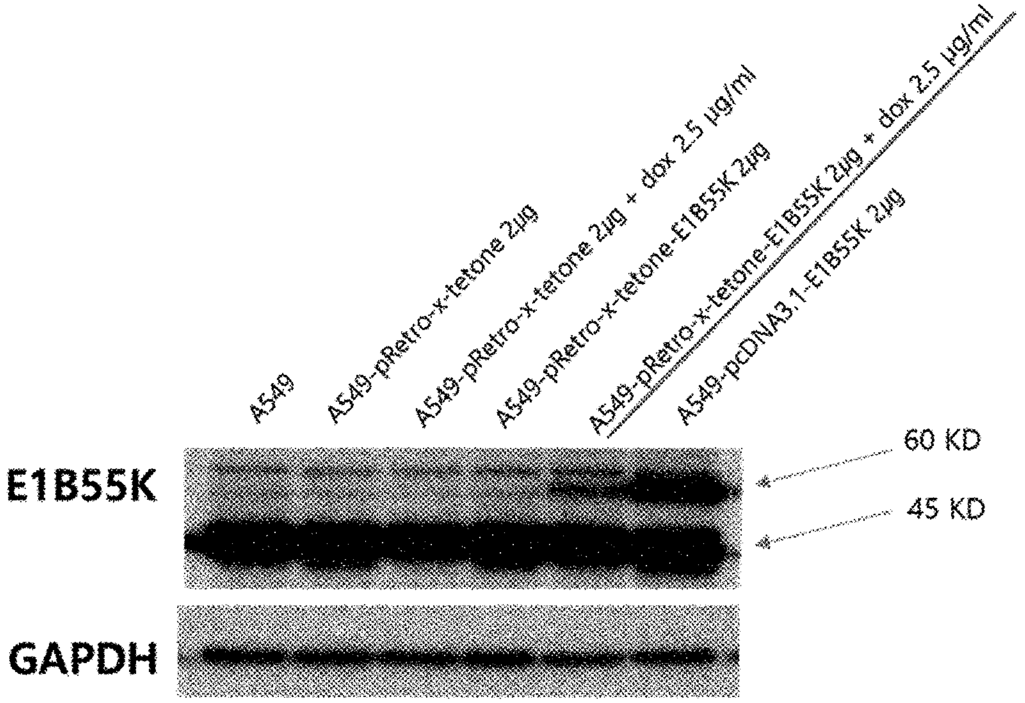
【FIG.19】
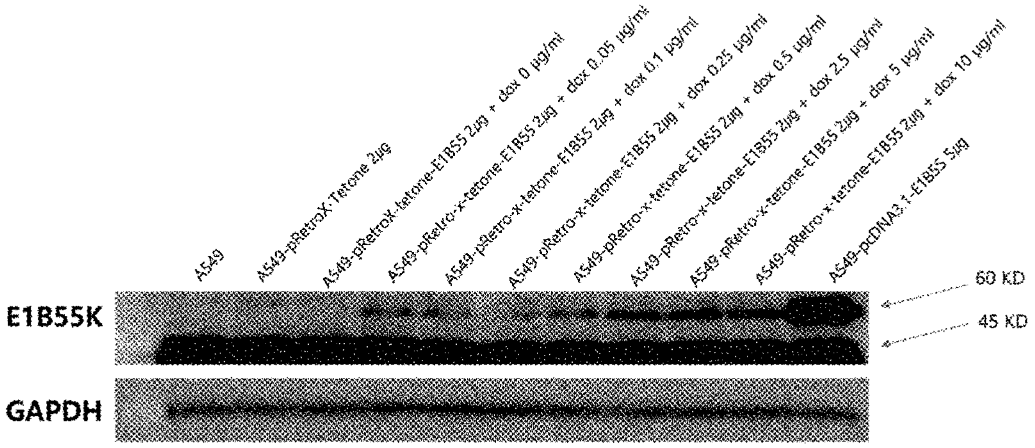

【FIG.20】
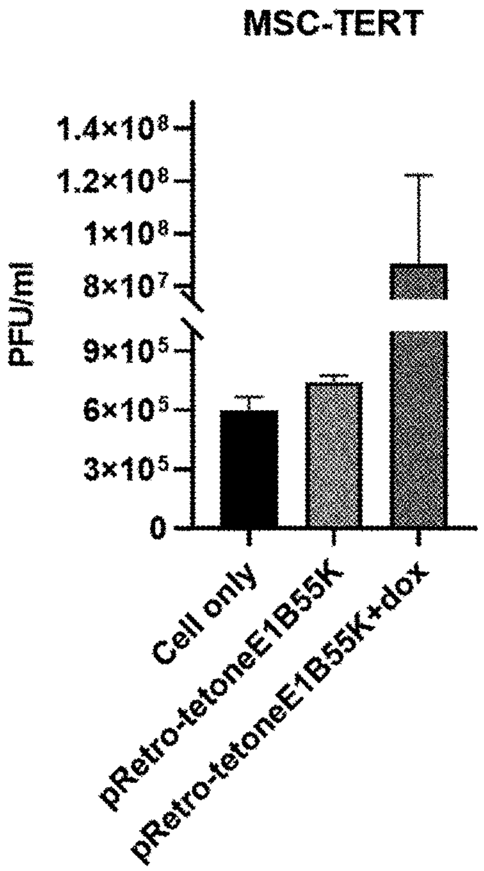
【FIG.21】
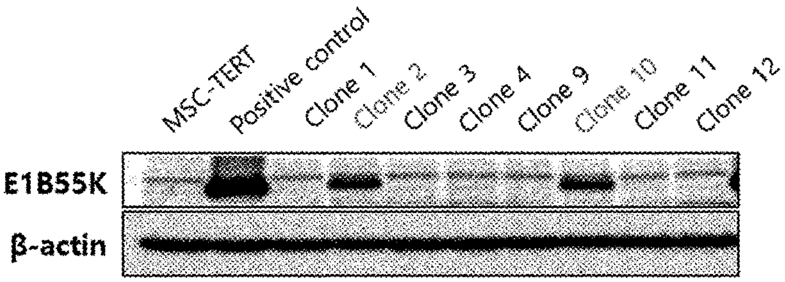

【FIG.22】
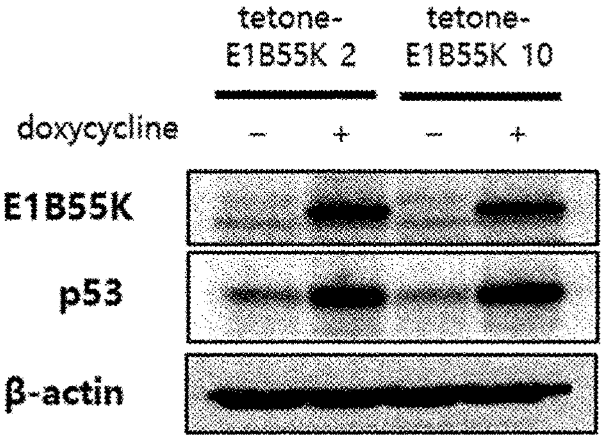
【FIG.23】
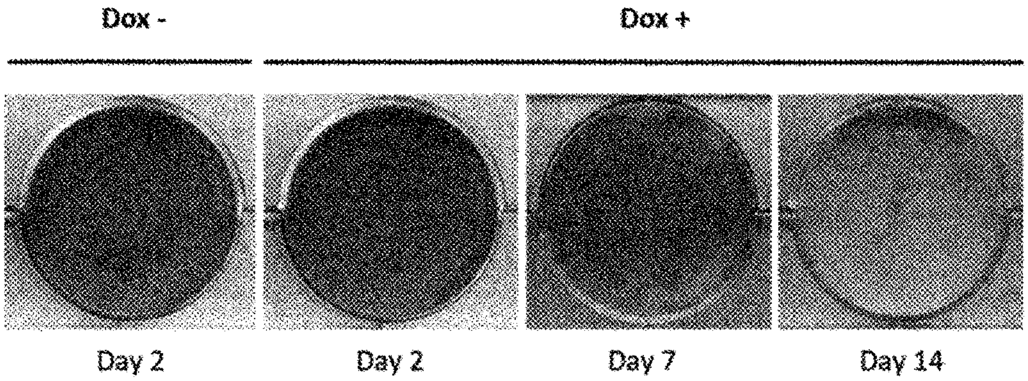

【FIG.24a】
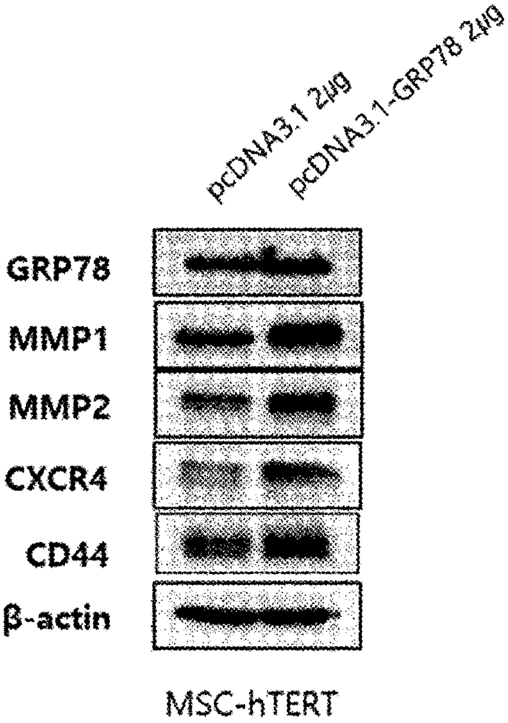
【FIG.24b】
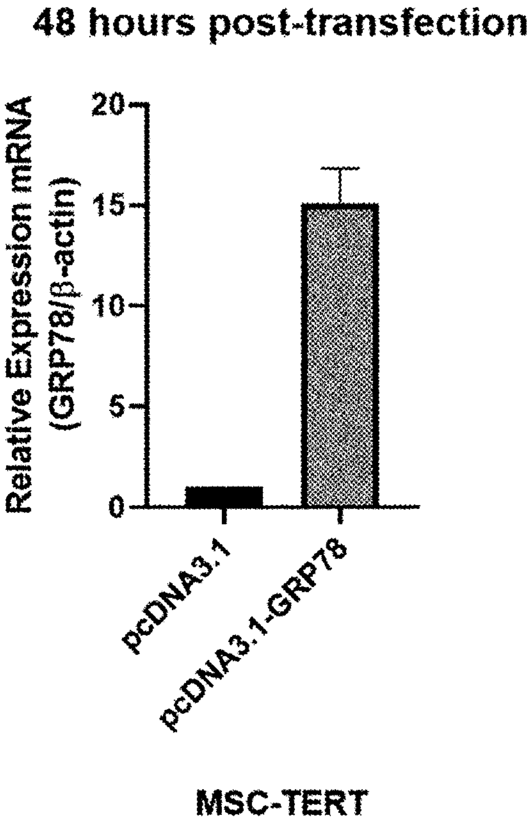

【FIG.25】
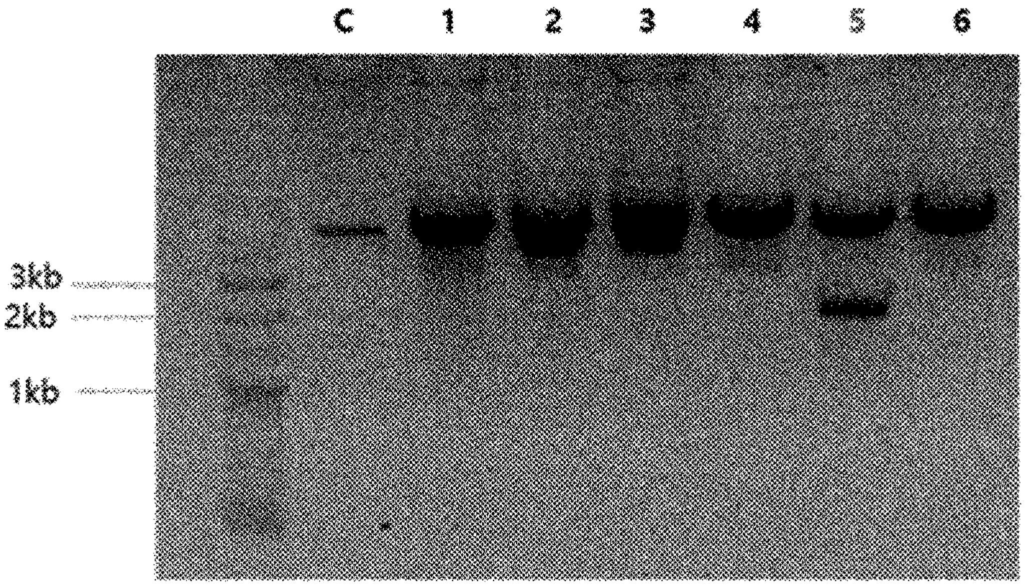
【FIG.26】
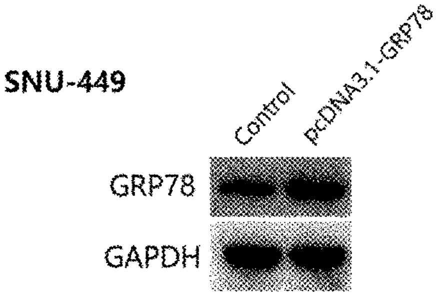

【FIG.27a】 pcDNA3.1 GRP78 forward

```
NM_005347_GRP78      --------------------------------------------atgaagctctccctgg
pcDNA3.1GRP78        TGGTGGAATTCTGCAGATATCCAGCACAGTGGCGGCCGCTCGAGATGAAGCTCTCCCTGG
                                                                 ****************

NM_005347_GRP78      tggccgcgatgctgctgctgctcagcgcggcgcgggccgaggaggaggacaagaaggagg
pcDNA3.1GRP78        TGGCCGCGATGCTGCTGCTGCTCAGCGCGGCGCGGGCCGAGGAGGAGGACAAGAAGGAGG
                     ************************************************************

NM_005347_GRP78      acgtgggcacggtggtcggcatcgacctggggaccacctactcctgcgtcggcgtgttca
pcDNA3.1GRP78        ACGTGGGCACGGTGGTCGGCATCGACCTGGGGACCACCTACTCCTGCGTCGGCGTGTTCA
                     ************************************************************

NM_005347_GRP78      agaacggccgcgtggagatcatcgccaacgatcagggcaaccgcatcacgccgtcctatg
pcDNA3.1GRP78        AGAACGGCCGCGTGGAGATCATCGCCAACGATCAGGGCAACCGCATCACGCCGTCCTATG
                     ************************************************************

NM_005347_GRP78      tcgccttcactcctgaaggggaacgtctgattggcgatgccgccaagaaccagctcacct
pcDNA3.1GRP78        TCGCCTTCACTCCTGAAGGGGAACGTCTGATTGGCGATGCCGCCAAGAACCAGCTCACCT
                     ************************************************************

NM_005347_GRP78      ccaaccccgagaacacggtctttgacgccaagcggctcatcggccgcacgtggaatgacc
pcDNA3.1GRP78        CCAACCCCGAGAACACGGTCTTTGACGCCAAGCGGCTCATCGGCCGCACGTGGAATGACC
                     ************************************************************

NM_005347_GRP78      cgtctgtgcagcaggacatcaagttcttgccgttcaaggtggttgaaaagaaaactaaac
pcDNA3.1GRP78        CGTCTGTGCAGCAGGACATCAAGTTCTTGCCGTTCAAGGTGGTTGAAAAGAAAACTAAAC
                     ************************************************************

NM_005347_GRP78      catacattcaagttgatattggaggtgggcaaacaaagacatttgctcctgaagaaattt
pcDNA3.1GRP78        CATACATTCAAGTTGATATTGGAGGTGGGCAAACAAAGACATTTGCTCCTGAAGAAATTT
                     ************************************************************

NM_005347_GRP78      ctgccatggttctcactaaaatgaaagaaaccgctgaggcttatttgggaaagaaggtta
pcDNA3.1GRP78        CTGCCATGGTTCTCACTAAAATGAAAGAAACCGCTGAGGCTTATTTGGGAAAGAAGGTTA
                     ************************************************************

NM_005347_GRP78      cccatgcagttgttactgtaccagcctattttaatgatgcccaacgccaagcaaccaaag
pcDNA3.1GRP78        CCCATGCAGTTGTTACTGTACCAGCCTATTTTAATGATGCCCAACGCCAAGCAACCAAAG
                     ************************************************************

NM_005347_GRP78      acgctggaactattgctggcctaaatgttatgaggatcatcaacgagcctacggcagctg
pcDNA3.1GRP78        ACGCTGGAACTATTGCTGGCCTAAATGTTATGAGGATCATCAACGAGCCTACGGCAGCTG
                     ************************************************************

NM_005347_GRP78      ctattgcttatggcctggataagagggagggggagaagaacatcctggtgtttgacctgg
pcDNA3.1GRP78        CTATTGCTTATGGCCTGGATAAGAGGGAGGGGGAGAAGAACATCCTGGTGTTTGACCTGG
                     ************************************************************

NM_005347_GRP78      gtggcggaaccttcgatgtgtctcttctcaccattgacaatggtgtcttcgaagttgtgg
pcDNA3.1GRP78        GTGGCGGAACCTTCGATGTGTCTCTTCTCACCATTGACAATGGTGTCTTCGAAGTTGTGG
                     ************************************************************

NM_005347_GRP78      ccactaatggagatactcatctgggtggagaagactttgaccagcgtgtcatggaacact
pcDNA3.1GRP78        CCACTAATGGAGATACTCATCTGGGTGGAGAAGACTTTGACCAGCGTGTCATGGAACACT
                     ************************************************************

NM_005347_GRP78      tcatcaaactgtacaaaaagaagacgggcaaagatgtcaggaaagacaatagagctgtgc
pcDNA3.1GRP78        TCATCAAACTGTACAAAAAGAAGACGGGCAAAGATGTCAGGAAAGACAATAGAGCTGTGC
                     ************************************************************

NM_005347_GRP78      agaaactccggcgcgaggtagaaaaggccaaacgggccctgtcttctcagcatcaagcaa
pcDNA3.1GRP78        AGAAACTCCGGCGCGAGGTAGAAAAGGCCAAACGGGCCCTGTCTTCTCAGCATCAAGCAA
                     ************************************************************

NM_005347_GRP78      gaattgaaattgagtccttctatgaaggagaagactttttctgagaccctgactcgggcca
pcDNA3.1GRP78        GAATTGAAATTGAGTCCTTCTATGAAGGAGAAGAC-------------------------
                     ***********************************
```

【FIG.27b】 pcDNA3.1 GRP78 reverse

```
NM_005347_GRP78      tctcagcatcaagcaagaattgaaattgagtccttctatgaaggagaagacttttctgag
pcDNA3.1GRP78        ----------------------------------TCTATGAAGGAGAAGACTTTTCTGAG
                                                       **************************

NM_005347_GRP78      accctgactcgggccaaatttgaagagctcaacatggatctgttccggtctactatgaag
pcDNA3.1GRP78        ACCCTGACTCGGGCCAAATTTGAAGAGCTCAACATGGATCTGTTCCGGTCTACTATGAAG
                     ************************************************************

NM_005347_GRP78      cccgtccagaaagtgttggaagattctgatttgaagaagtctgatattgatgaaattgtt
pcDNA3.1GRP78        CCCGTCCAGAAAGTGTTGGAAGATTCTGATTTGAAGAAGTCTGATATTGATGAAATTGTT
                     ************************************************************

NM_005347_GRP78      cttgttggtggctcgactcgaattccaaagattcagcaactggttaaagagttcttcaat
pcDNA3.1GRP78        CTTGTTGGTGGCTCGACTCGAATTCCAAAGATTCAGCAACTGGTTAAAGAGTTCTTCAAT
                     ************************************************************

NM_005347_GRP78      ggcaaggaaccatcccgtggcataaacccagatgaagctgtagcgtatggtgctgctgtc
pcDNA3.1GRP78        GGCAAGGAACCATCCCGTGGCATAAACCCAGATGAAGCTGTAGCGTATGGTGCTGCTGTC
                     ************************************************************

NM_005347_GRP78      caggctggtgtgctctctggtgatcaagatacaggtgacctggtactgcttgatgtatgt
pcDNA3.1GRP78        CAGGCTGGTGTGCTCTCTGGTGATCAAGATACAGGTGACCTGGTACTGCTTGATGTATGT
                     ************************************************************

NM_005347_GRP78      ccccttacacttggtattgaaactgtgggaggtgtcatgaccaaactgattccaaggaac
pcDNA3.1GRP78        CCCCTTACACTTGGTATTGAAACTGTGGGAGGTGTCATGACCAAACTGATTCCAAGGAAC
                     ************************************************************

NM_005347_GRP78      acagtggtgcctaccaagaagtctcagatcttttctacagcttctgataatcaaccaact
pcDNA3.1GRP78        ACAGTGGTGCCTACCAAGAAGTCTCAGATCTTTTCTACAGCTTCTGATAATCAACCAACT
                     ************************************************************

NM_005347_GRP78      gttacaatcaaggtctatgaaggtgaaagacccctgacaaaagacaatcatcttctgggt
pcDNA3.1GRP78        GTTACAATCAAGGTCTATGAAGGTGAAAGACCCCTGACAAAAGACAATCATCTTCTGGGT
                     ************************************************************

NM_005347_GRP78      acatttgatctgactggaattcctcctgctcctcgtggggtcccacagattgaagtcacc
pcDNA3.1GRP78        ACATTTGATCTGACTGGAATTCCTCCTGCTCCTCGTGGGGTCCCACAGATTGAAGTCACC
                     ************************************************************

NM_005347_GRP78      tttgagatagatgtgaatggtattcttcgagtgacagctgaagacaagggtacagggaac
pcDNA3.1GRP78        TTTGAGATAGATGTGAATGGTATTCTTCGAGTGACAGCTGAAGACAAGGGTACAGGGAAC
                     ************************************************************

NM_005347_GRP78      aaaaataagatcacaatcaccaatgaccagaatcgcctgacacctgaagaaatcgaaagg
pcDNA3.1GRP78        AAAAATAAGATCACAATCACCAATGACCAGAATCGCCTGACACCTGAAGAAATCGAAAGG
                     ************************************************************

NM_005347_GRP78      atggttaatgatgctgagaagtttgctgaggaagacaaaaagctcaaggagcgcattgat
pcDNA3.1GRP78        ATGGTTAATGATGCTGAGAAGTTTGCTGAGGAAGACAAAAAGCTCAAGGAGCGCATTGAT
                     ************************************************************

NM_005347_GRP78      actagaaatgagttggaaagctatgcctattctctaaagaatcagattggagataaagaa
pcDNA3.1GRP78        ACTAGAAATGAGTTGGAAAGCTATGCCTATTCTCTAAAGAATCAGATTGGAGATAAAGAA
                     ************************************************************

NM_005347_GRP78      aagctgggaggtaaactttcctctgaagataaggagaccatggaaaaagctgtagaagaa
pcDNA3.1GRP78        AAGCTGGGAGGTAAACTTTCCTCTGAAGATAAGGAGACCATGGAAAAAGCTGTAGAAGAA
                     ************************************************************

NM_005347_GRP78      aagattgaatggctggaaagccaccaagatgctgacattgaagacttcaaagctaagaag
pcDNA3.1GRP78        AAGATTGAATGGCTGGAAAGCCACCAAGATGCTGACATTGAAGACTTCAAAGCTAAGAAG
                     ************************************************************

NM_005347_GRP78      aaggaactggaagaaattgttcaaccaattatcagcaaactctatggaagtgcaggccct
pcDNA3.1GRP78        AAGGAACTGGAAGAAATTGTTCAACCAATTATCAGCAAACTCTATGGAAGTGCAGGCCCT
                     ************************************************************

NM_005347_GRP78      cccccaactggtgaagaggatacagcagaaaaagatgagttgtag---------------
pcDNA3.1GRP78        CCCCCAACTGGTGAAGAGGATACAGCAGAAAAAGATGAGTTGTAGTCTAGAGTCCCGTAA
                     *********************************************
```

【FIG.28】
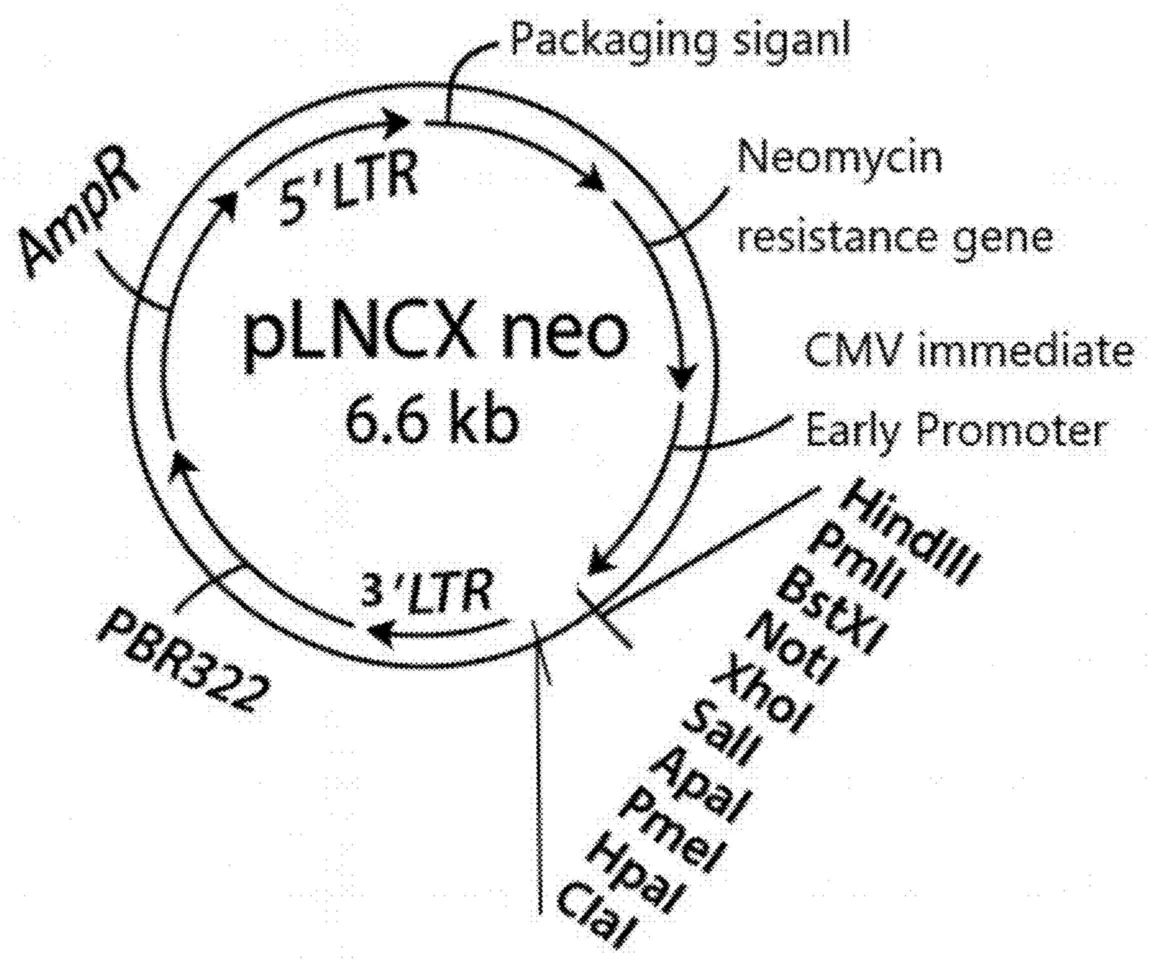

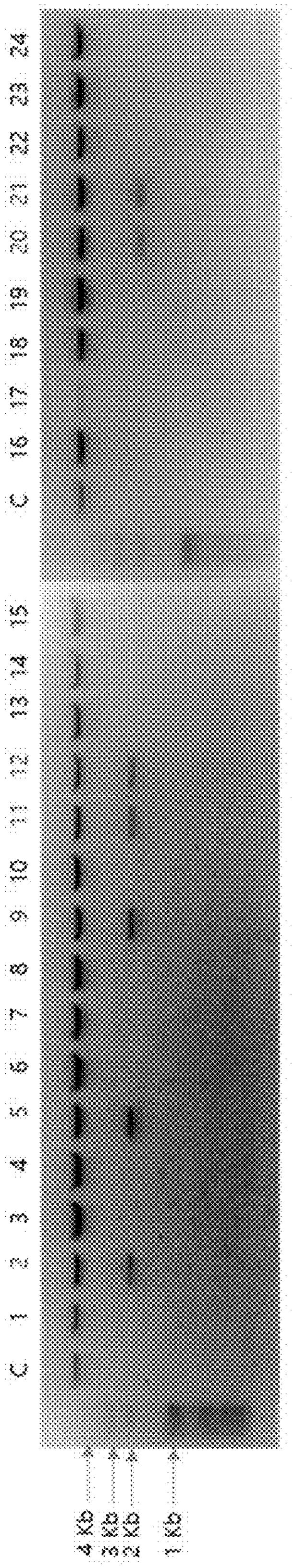
C : pLNCX Neo
2,5,9,11,12,20,21 right construct: pLNCXNeo-GRP78
【FIG.29】

【FIG.30】
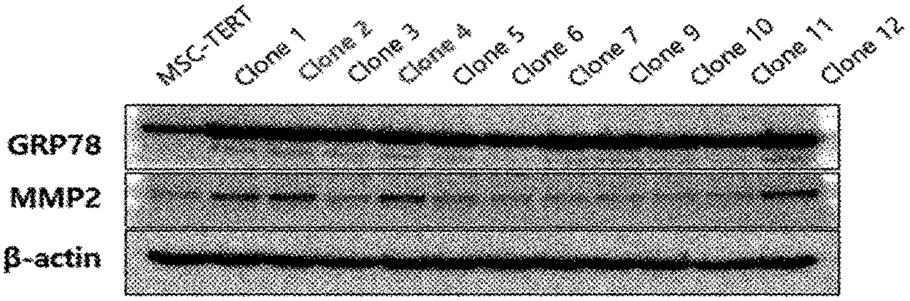

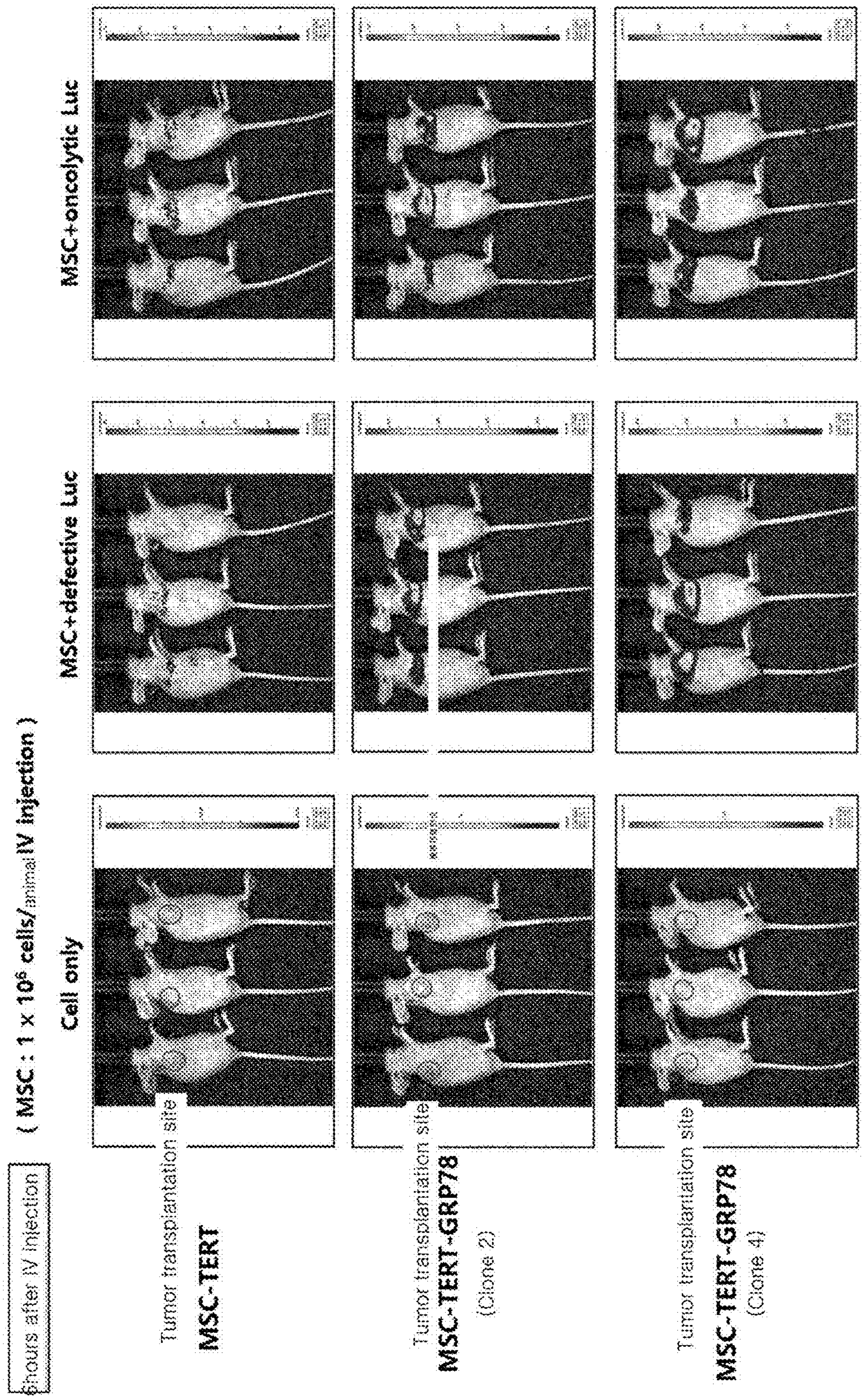
【FIG.31】

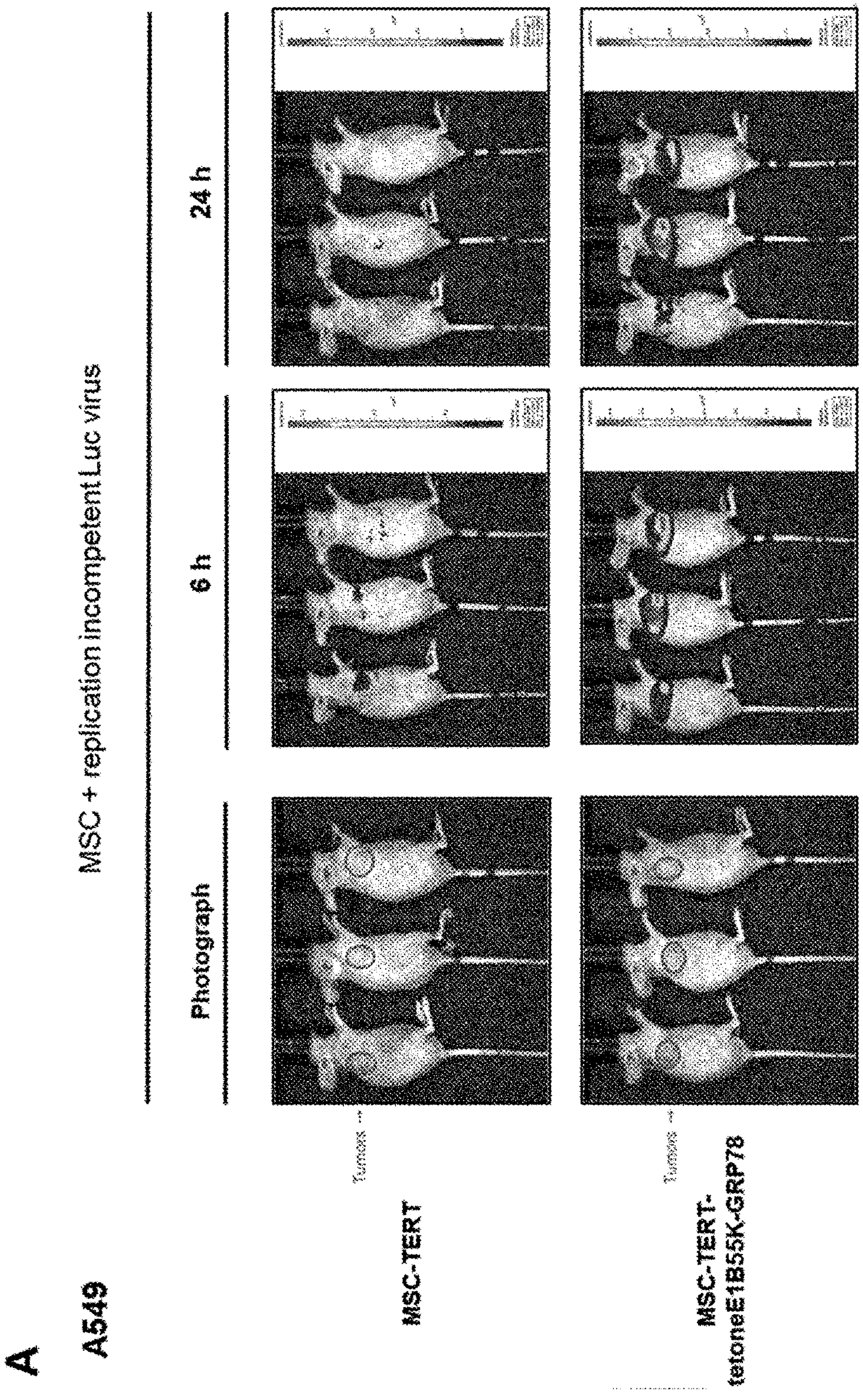
【FIG.32a】

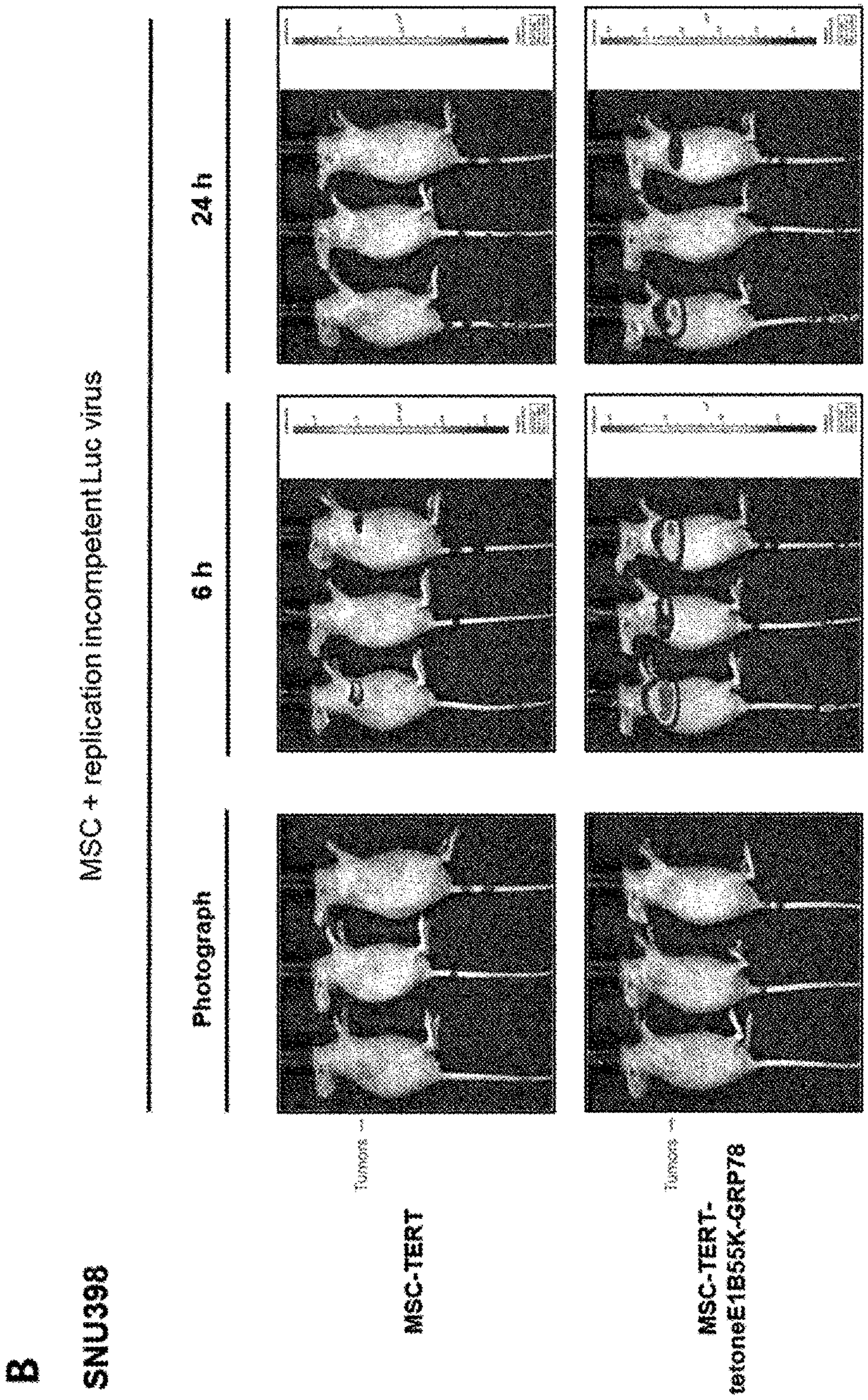
【FIG.32b】

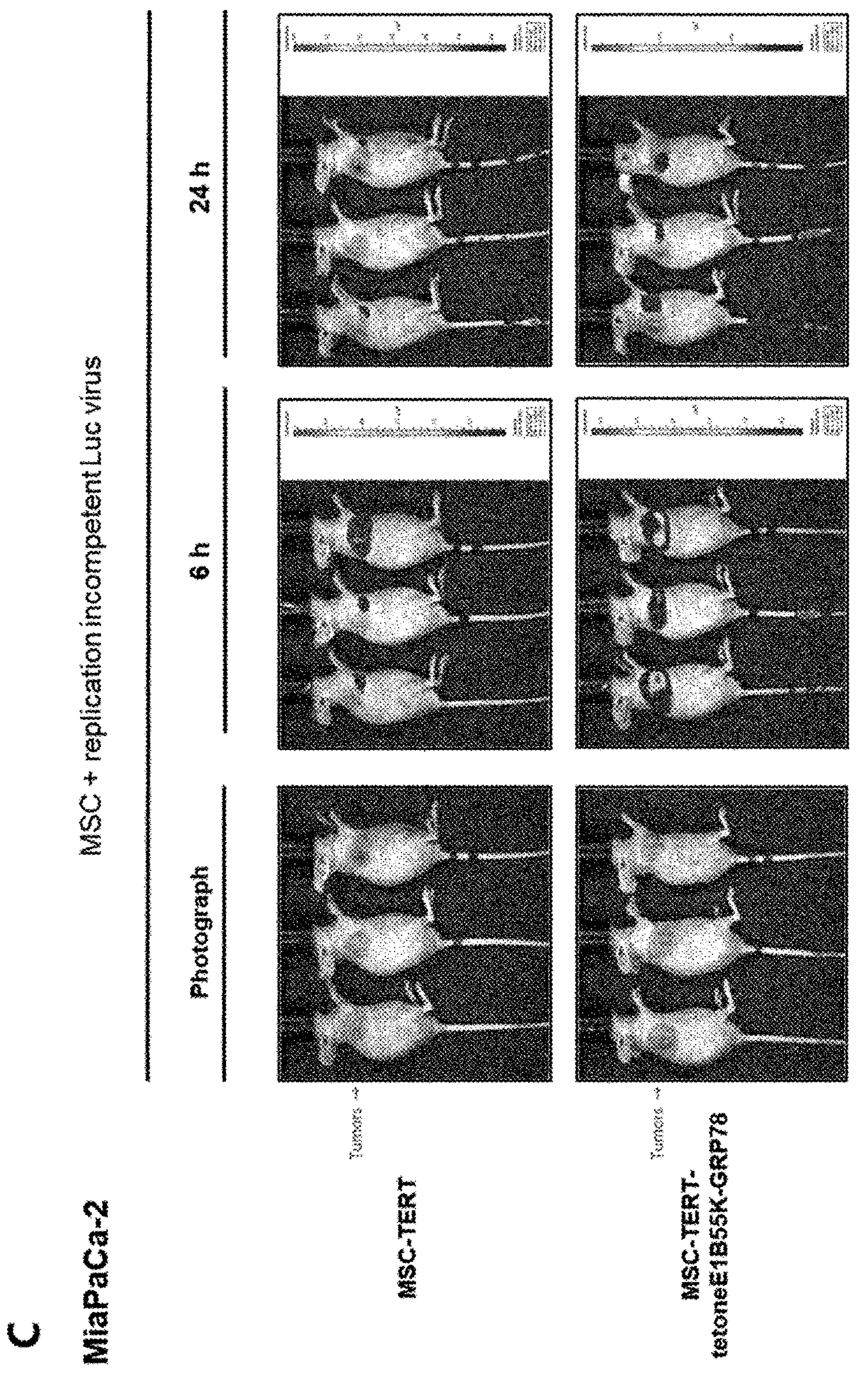
【FIG.32c】

【FIG.33a】
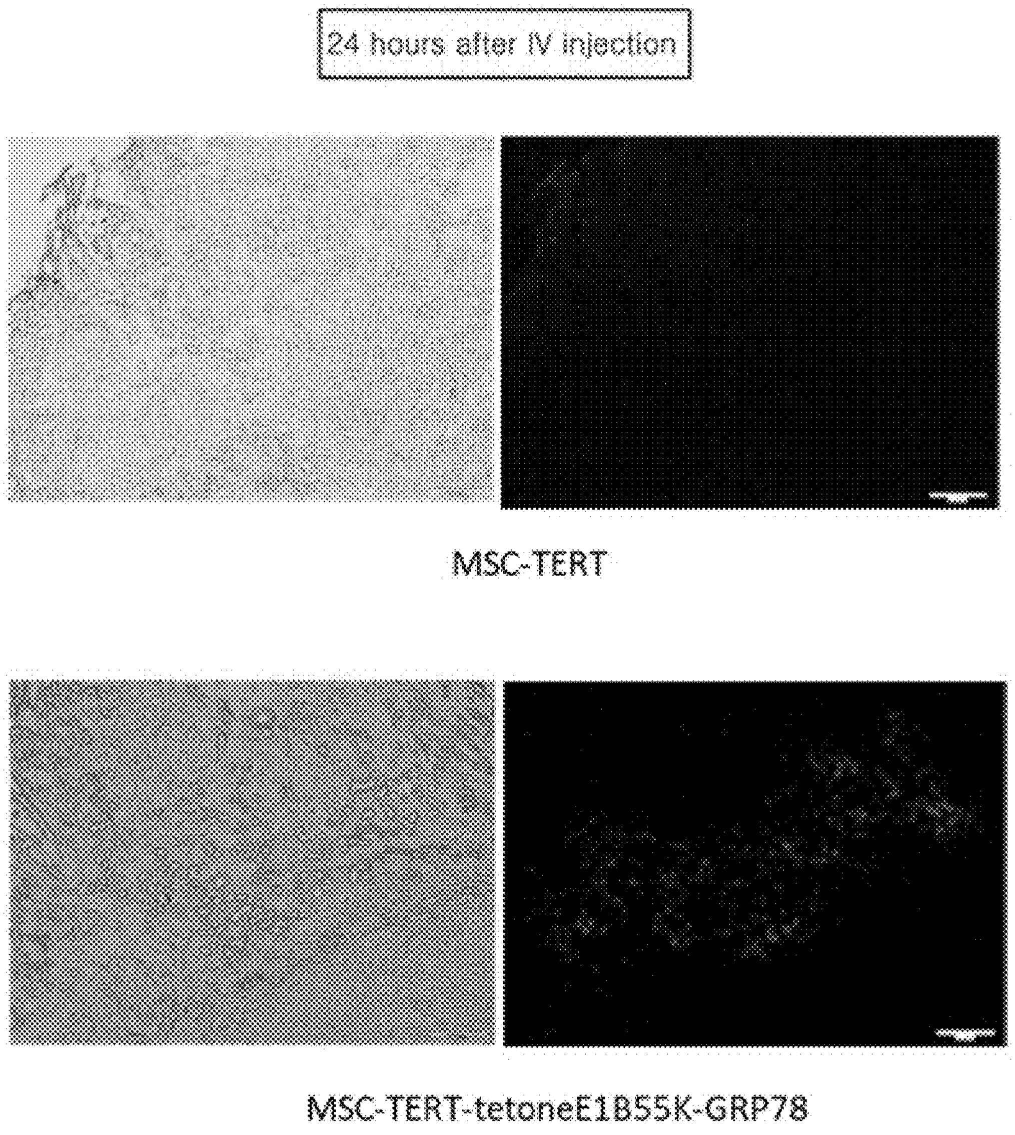

【FIG.33b】
48 hours after IV injection
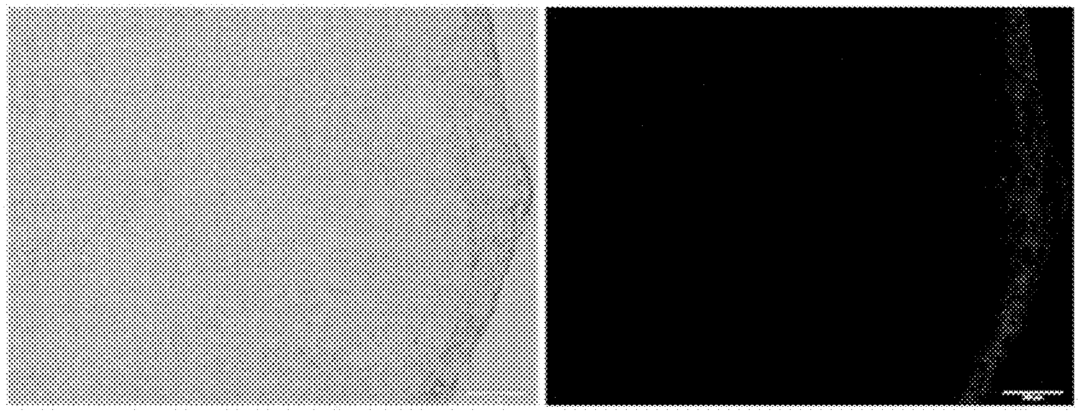
MSC-TERT
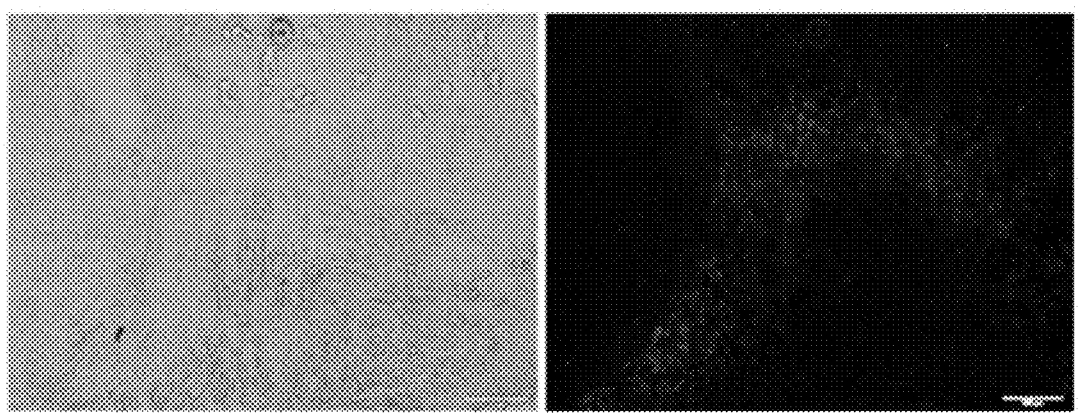
MSC-TERT-tetoneE1B55K-GRP78

【FIG.33c】
72 hours after IV injection
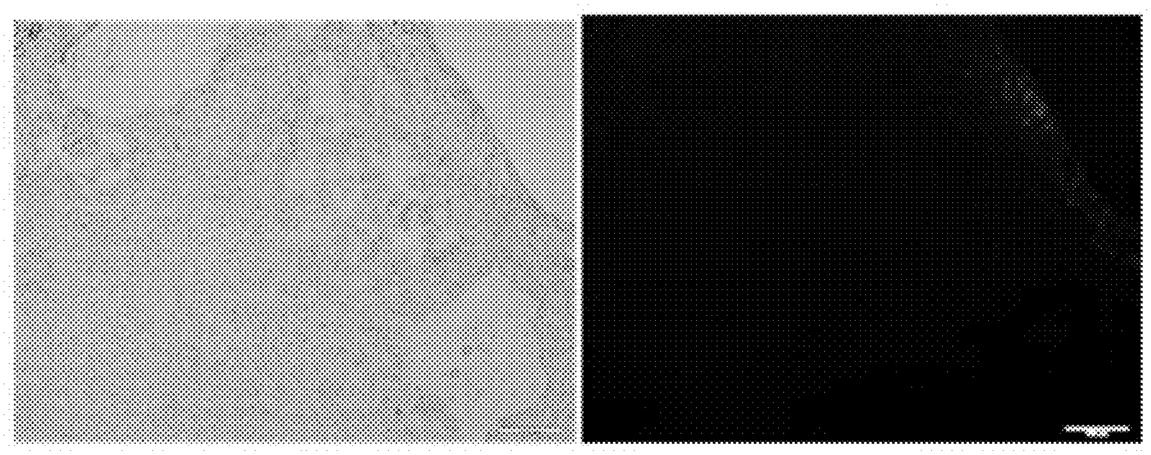
MSC-TERT
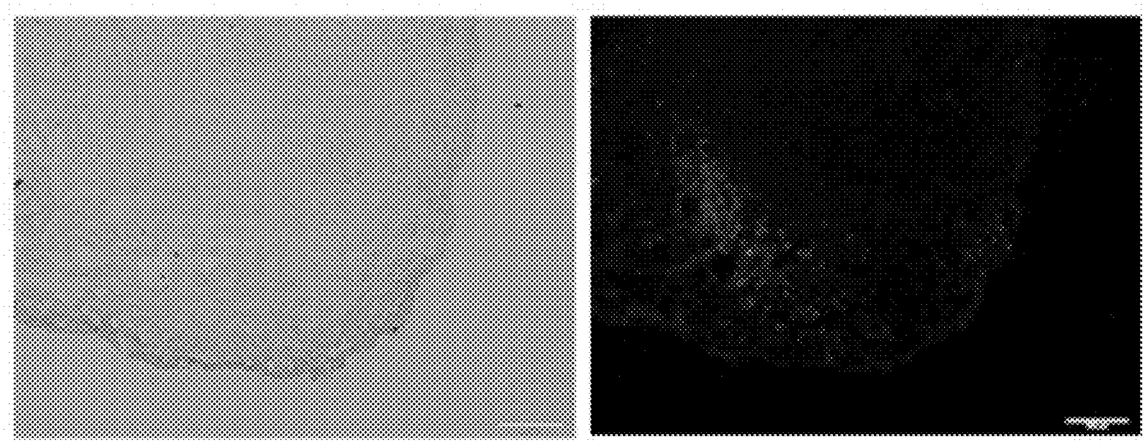
MSC-TERT-tetoneE1B55K-GRP78

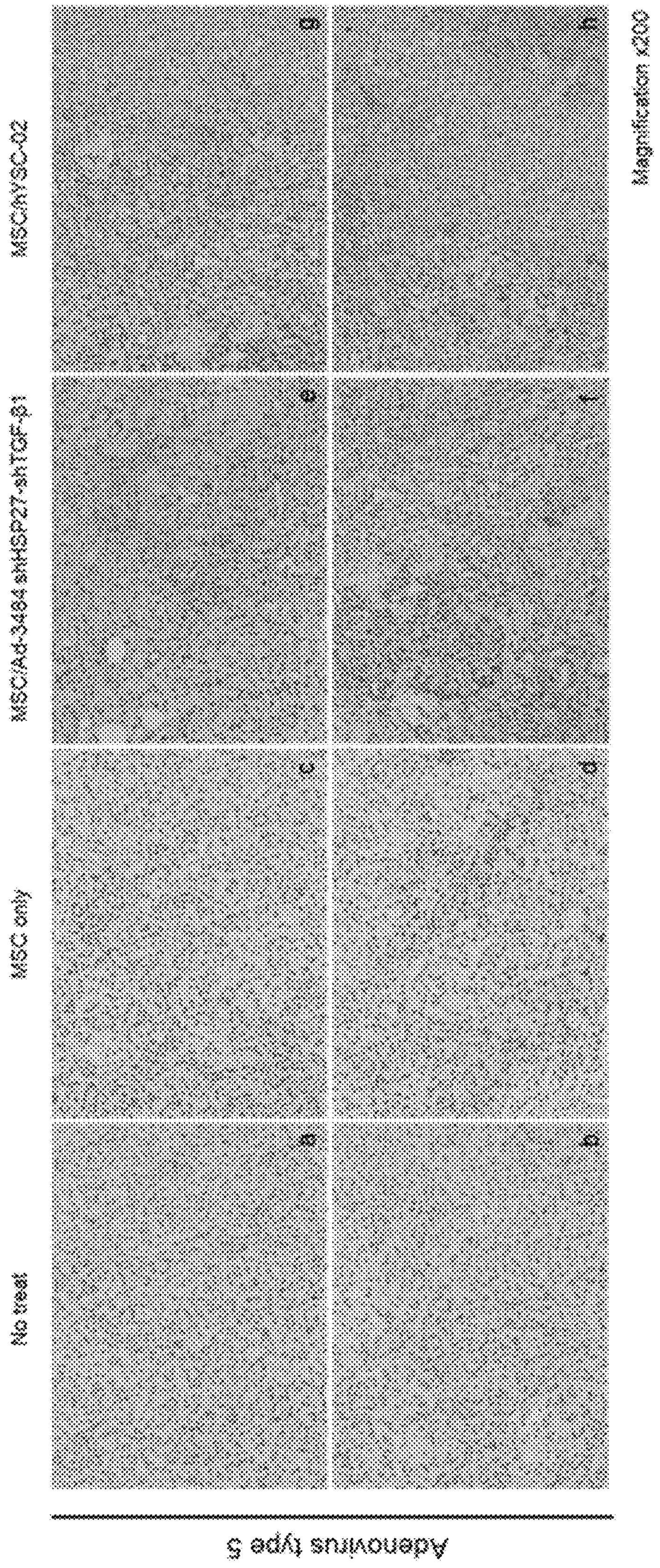
【FIG.34】

【FIG.35】
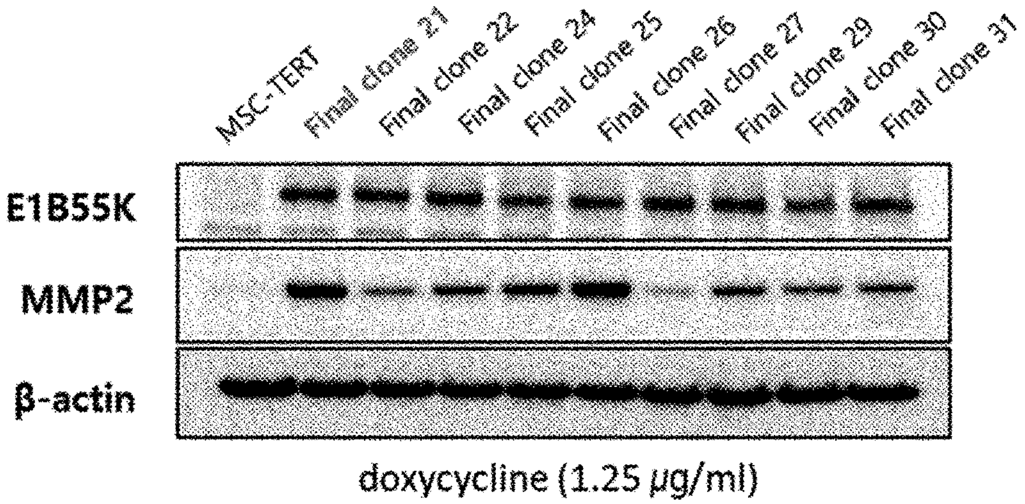
【FIG.36】
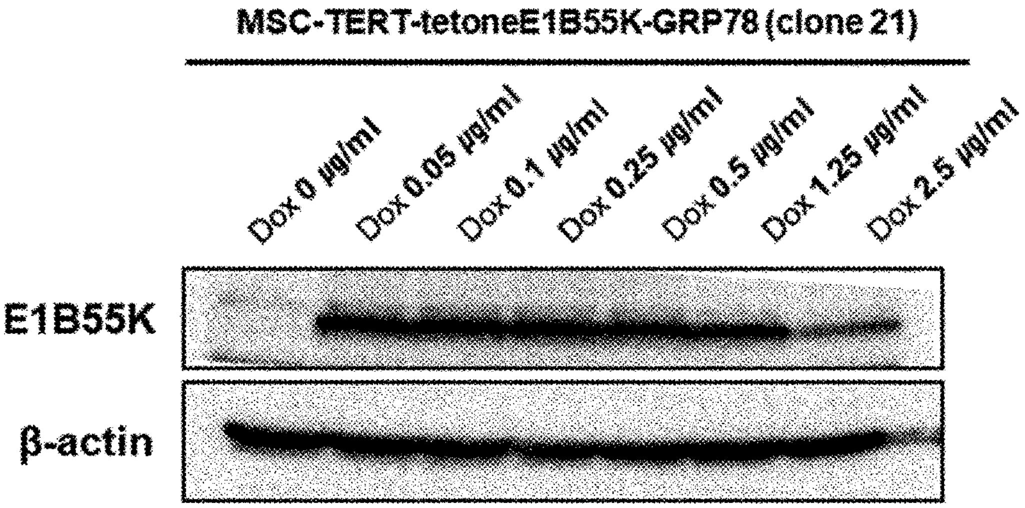
【FIG.37】
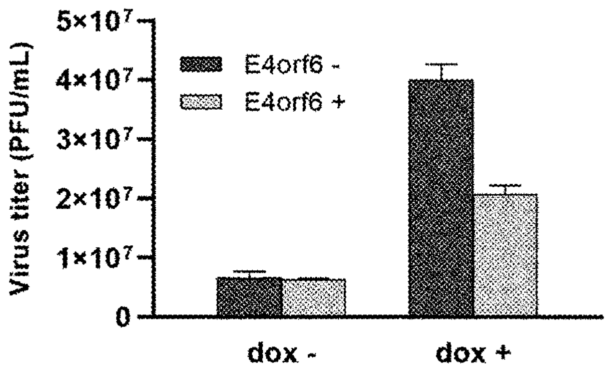

【FIG.38】
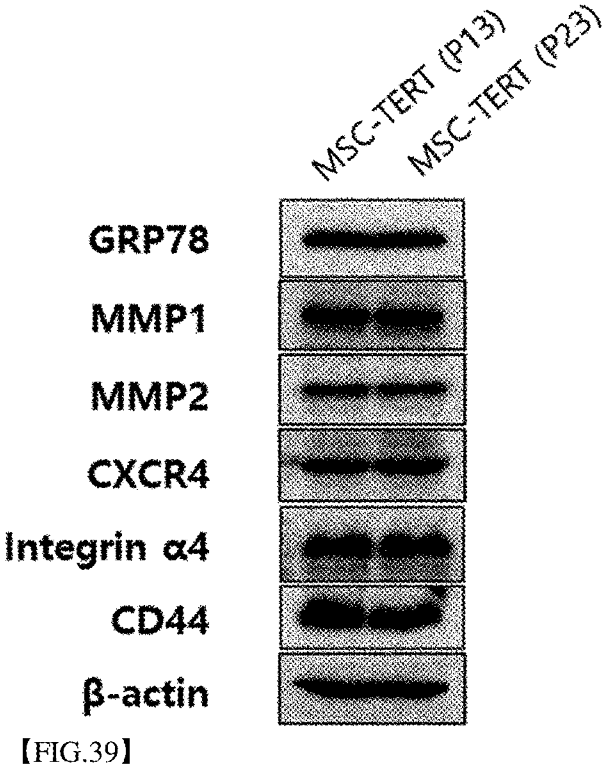
【FIG.39】
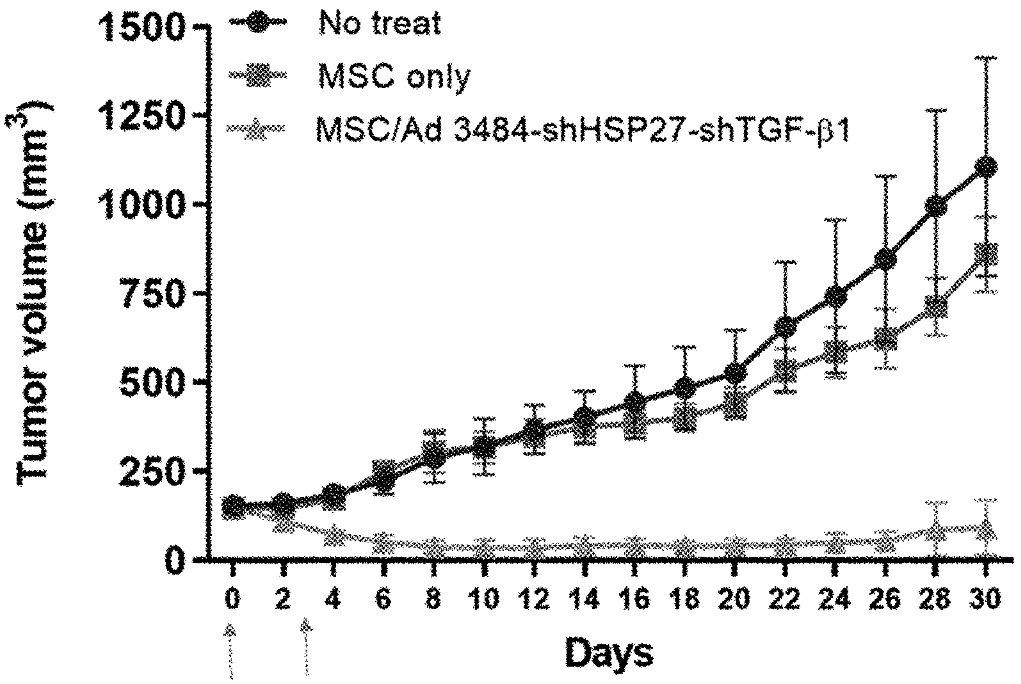

【FIG.40a】
Size of tumor removed 30 days after OV/MSC after 10 animals per group were separated into groups
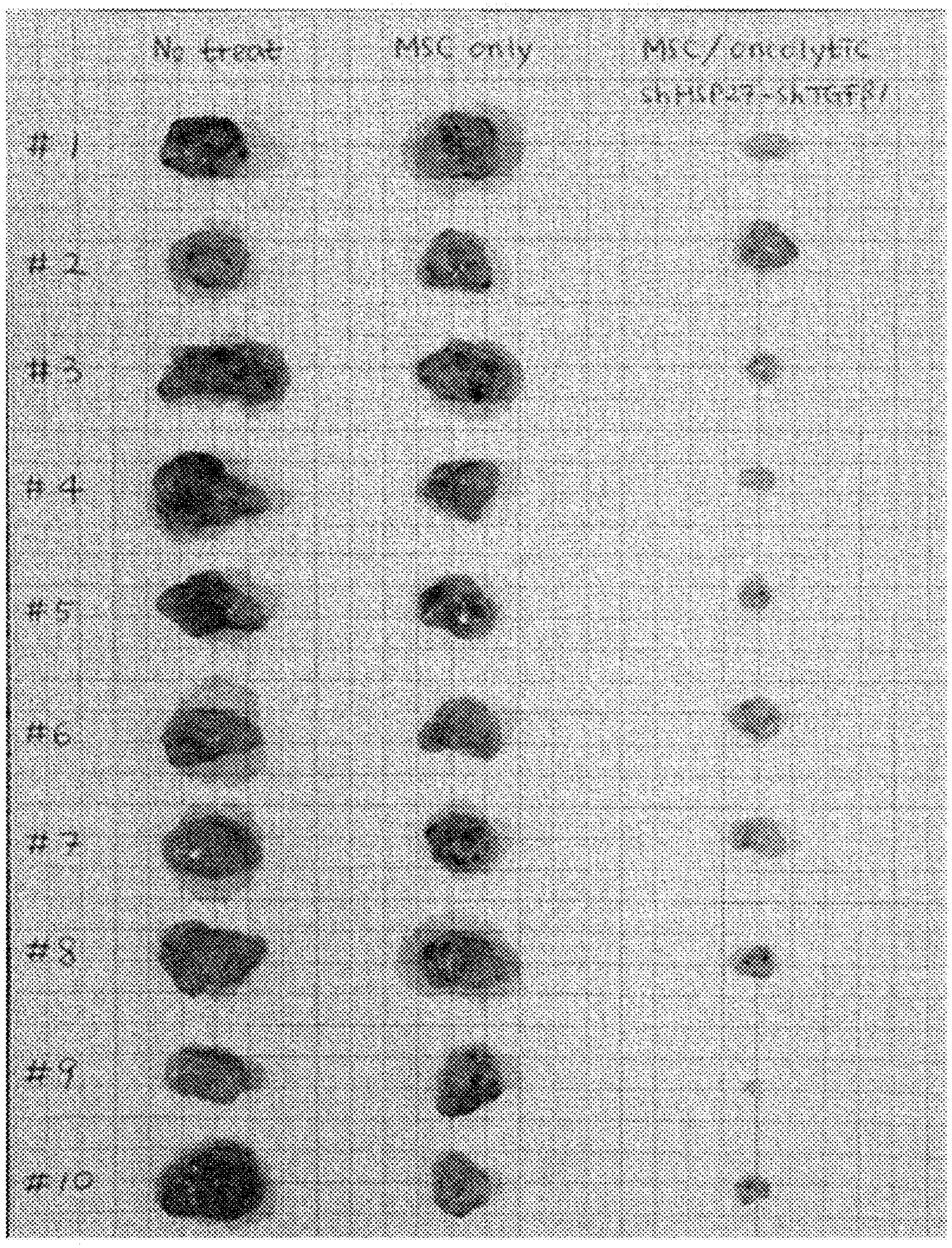

【FIG.40b】
No treat
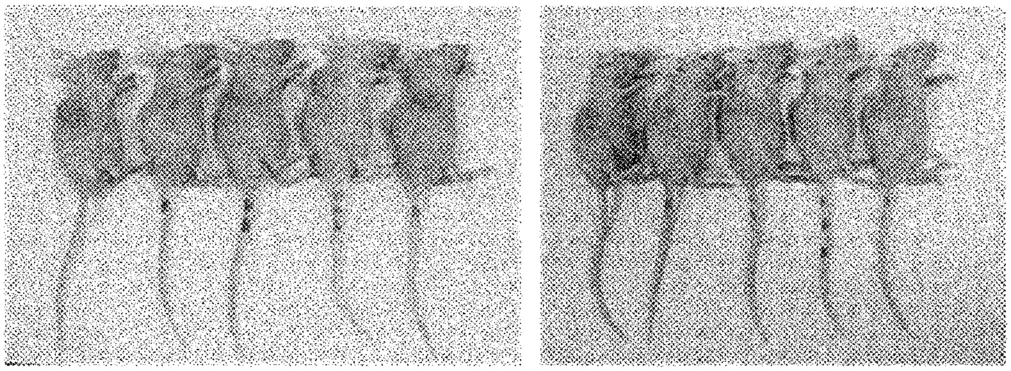
MSC only
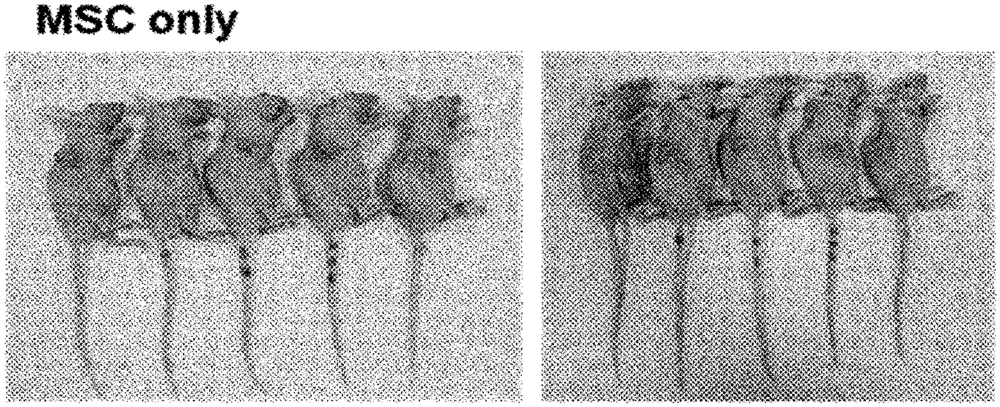
MSC/Ad-3484 shHSP27-shTGF-β1
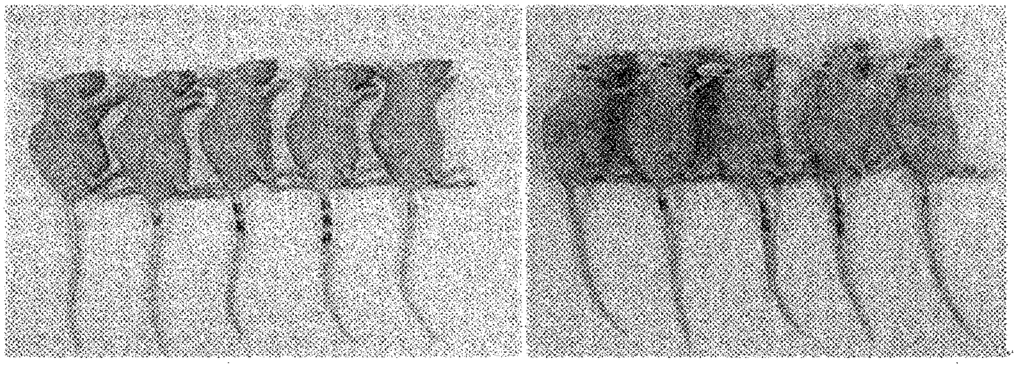

【FIG.41a】
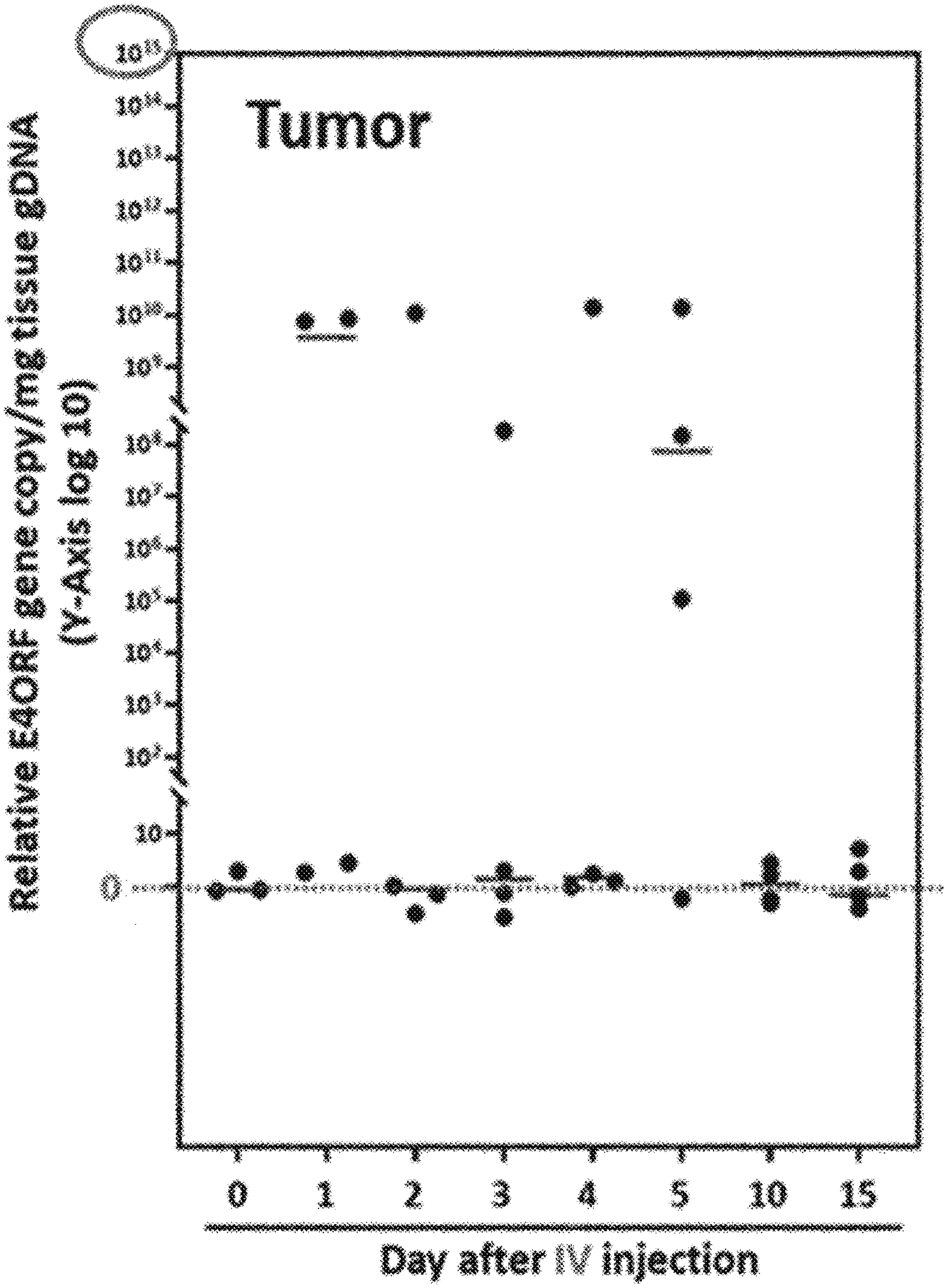

【FIG.41b】
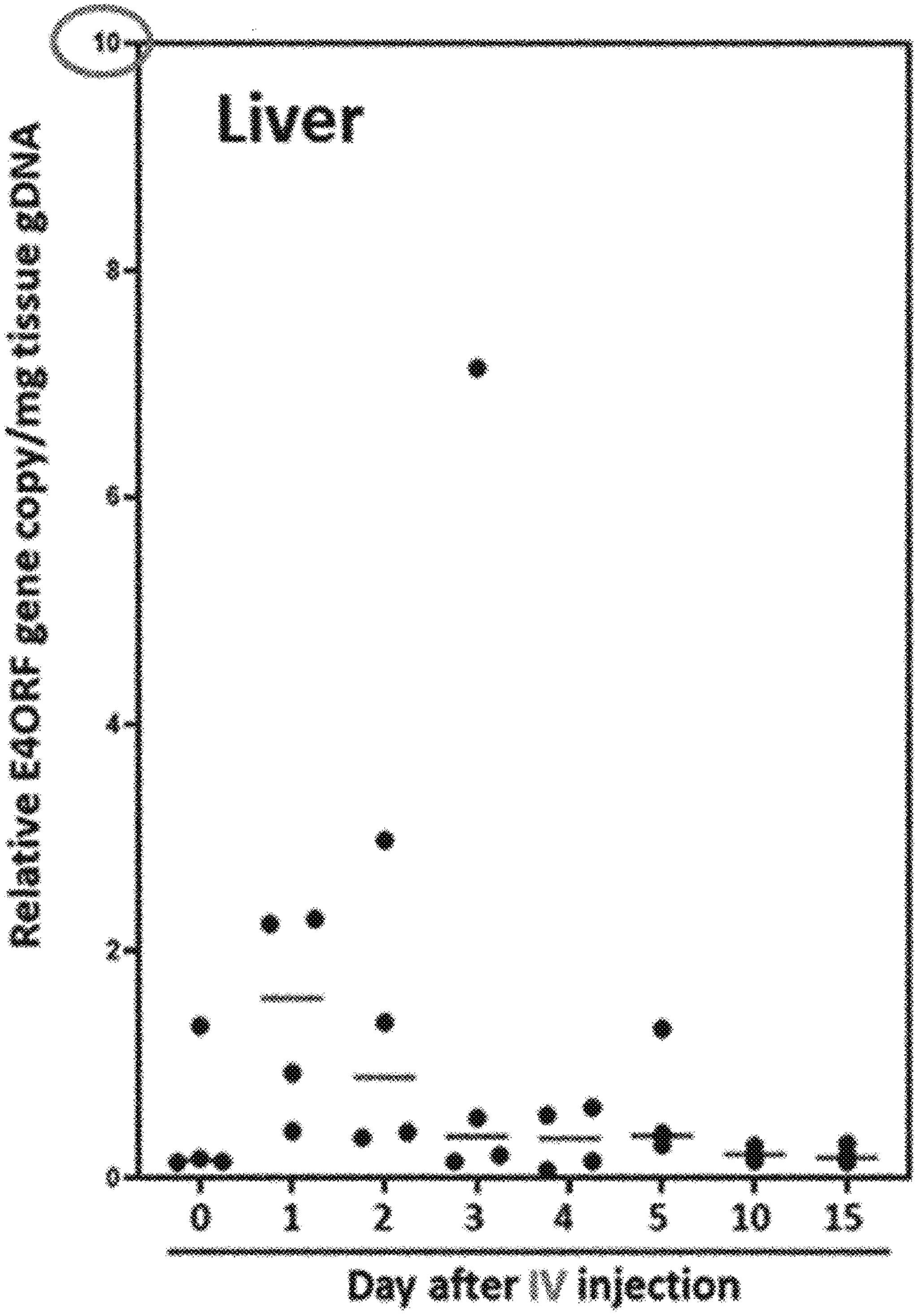

【FIG.41c】
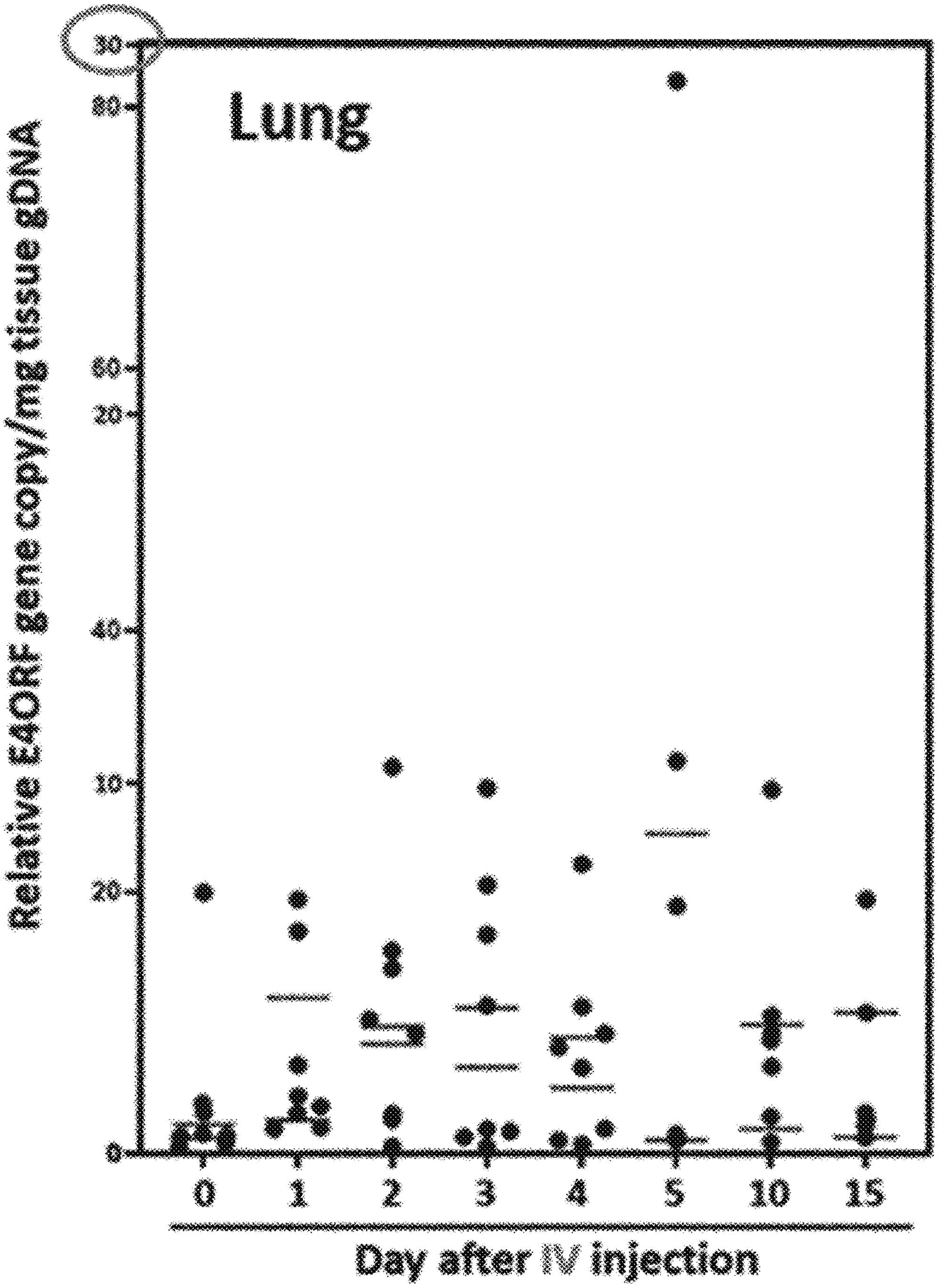

【FIG.41d】
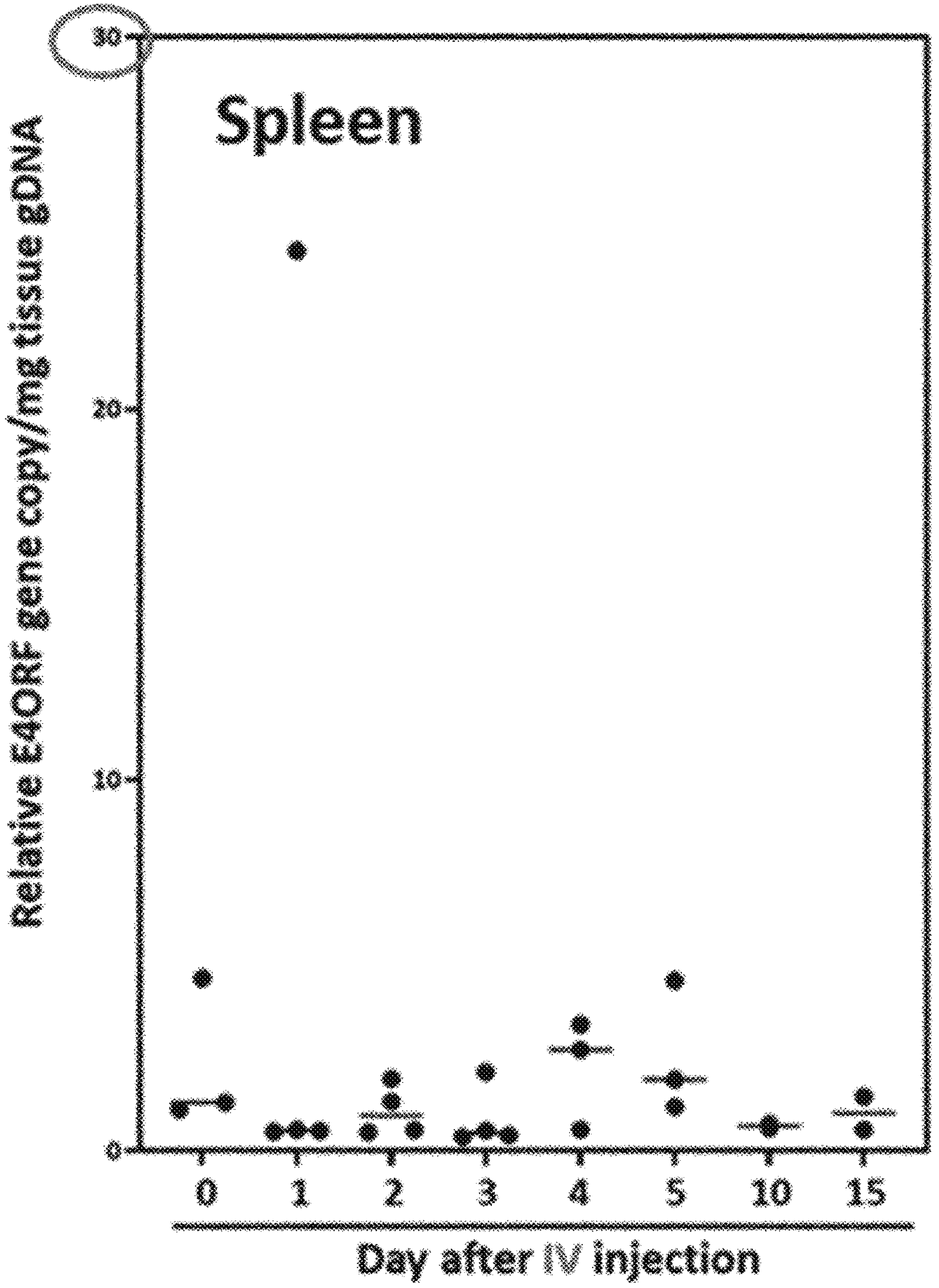

【FIG.41e】
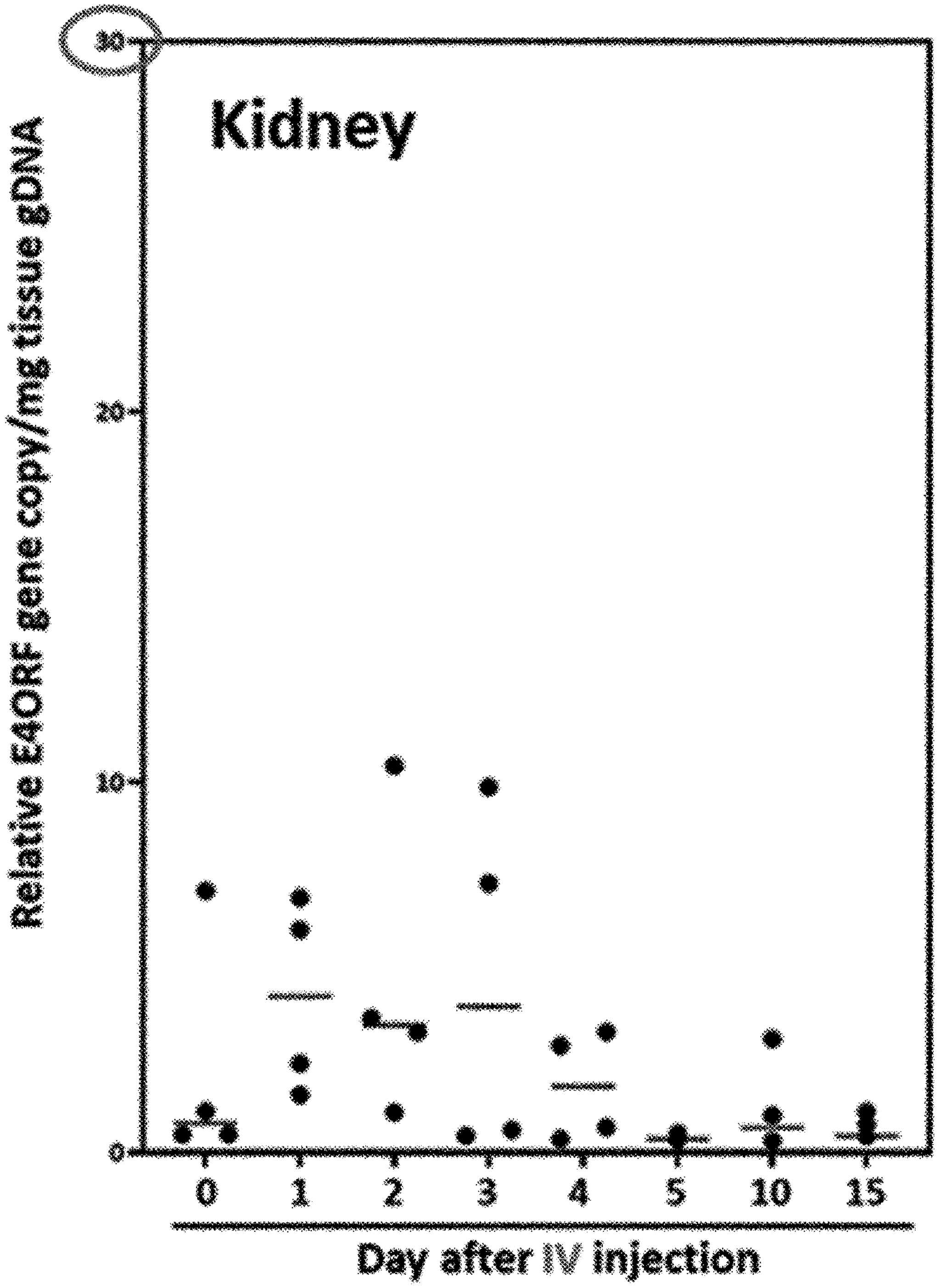

【FIG.41f】
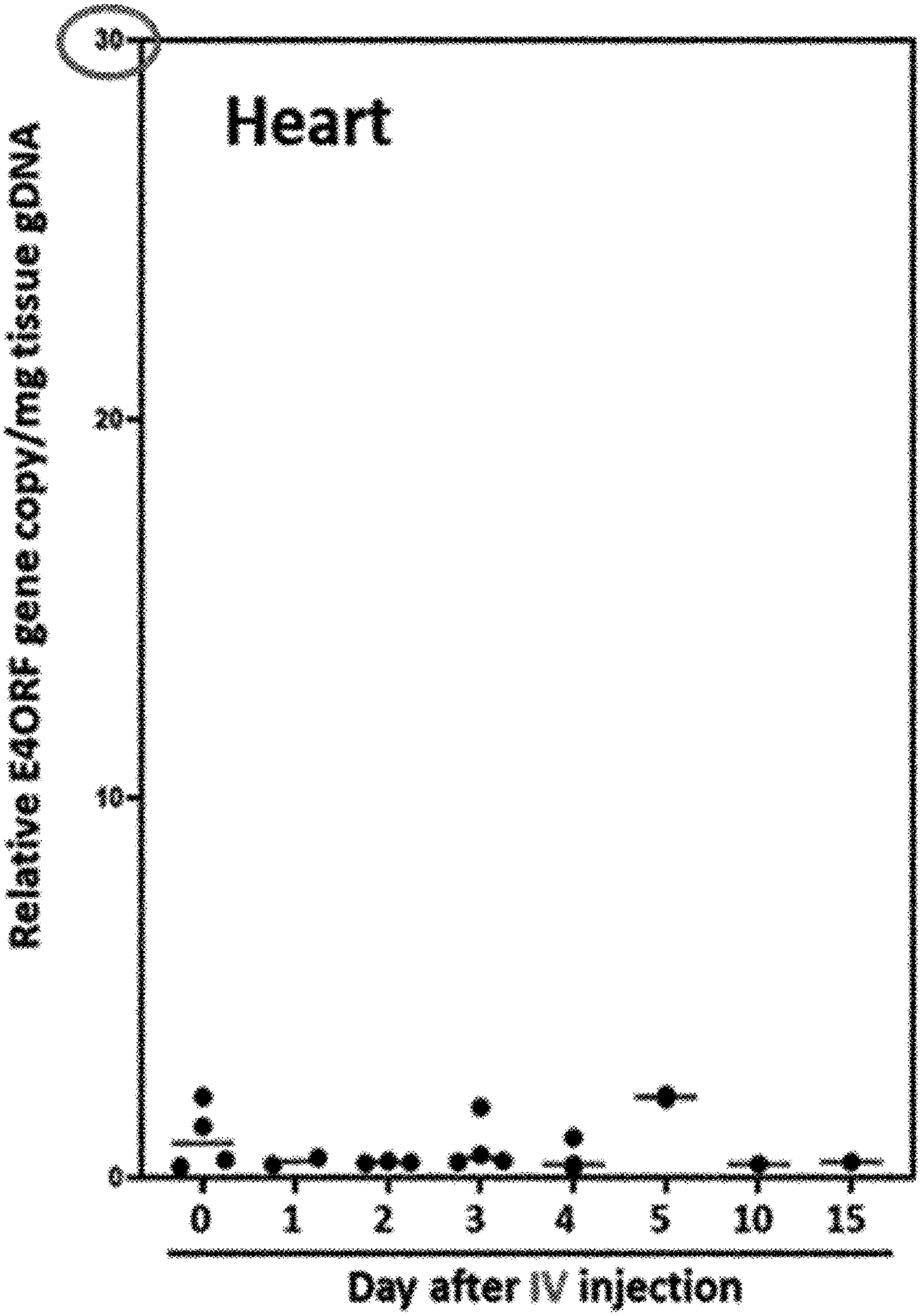

SEQUENCE LISTING

```
<160> NUMBER OF SEQ ID NOS: 31

<210> SEQ ID NO 1
<211> LENGTH: 1965
<212> TYPE: DNA
<213> ORGANISM: Homo sapiens

<400> SEQUENCE: 1

atgaagctct ccctggtggc cgcgatgctg ctgctgctca gcgcggcgcg ggccgaggag     60

gaggacaaga aggaggacgt gggcacggtg gtcggcatcg acctggggac cacctactcc    120

tgcgtcggcg tgttcaagaa cggccgcgtg gagatcatcg ccaacgatca gggcaaccgc    180

atcacgccgt cctatgtcgc cttcactcct gaaggggaac gtctgattgg cgatgccgcc    240

aagaaccagc tcacctccaa ccccgagaac acggtctttg acgccaagcg gctcatcggc    300

cgcacgtgga atgacccgtc tgtgcagcag gacatcaagt tcttgccgtt caaggtggtt    360

gaaaagaaaa ctaaaccata cattcaagtt gatattggag gtgggcaaac aaagacattt    420

gctcctgaag aaatttctgc catggttctc actaaaatga aagaaaccgc tgaggcttat    480

ttgggaaaga aggttaccca tgcagttgtt actgtaccag cctattttaa tgatgcccaa    540

cgccaagcaa ccaaagacgc tggaactatt gctggcctaa atgttatgag gatcatcaac    600

gagcctacgg cagctgctat tgcttatggc ctggataaga gggaggggga gaagaacatc    660

ctggtgtttg acctgggtgg cggaaccttc gatgtgtctc ttctcaccat tgacaatggt    720

gtcttcgaag ttgtggccac taatggagat actcatctgg gtggagaaga ctttgaccag    780

cgtgtcatgg aacacttcat caaactgtac aaaaagaaga cgggcaaaga tgtcaggaaa    840

gacaatagag ctgtgcagaa actccggcgc gaggtagaaa aggccaaacg ggccctgtct    900

tctcagcatc aagcaagaat tgaaattgag tccttctatg aaggagaaga cttttctgag    960

accctgactc gggccaaatt tgaagagctc aacatggatc tgttccggtc tactatgaag   1020

cccgtccaga aagtgttgga agattctgat ttgaagaagt ctgatattga tgaaattgtt   1080

cttgttggtg gctcgactcg aattccaaag attcagcaac tggttaaaga gttcttcaat   1140

ggcaaggaac catcccgtgg cataaaccca gatgaagctg tagcgtatgg tgctgctgtc   1200
```

```
caggctggtg tgctctctgg tgatcaagat acaggtgacc tggtactgct tgatgtatgt   1260

ccccttacac ttggtattga aactgtggga ggtgtcatga ccaaactgat tccaaggaac   1320

acagtggtgc ctaccaagaa gtctcagatc ttttctacag cttctgataa tcaaccaact   1380

gttacaatca aggtctatga aggtgaaaga cccctgacaa aagacaatca tcttctgggt   1440

acatttgatc tgactggaat tcctcctgct cctcgtgggg tcccacagat tgaagtcacc   1500

tttgagatag atgtgaatgg tattcttcga gtgacagctg aagacaaggg tacagggaac   1560

aaaaataaga tcacaatcac caatgaccag aatcgcctga cacctgaaga aatcgaaagg   1620

atggttaatg atgctgagaa gtttgctgag gaagacaaaa agctcaagga gcgcattgat   1680

actagaaatg agttggaaag ctatgcctat tctctaaaga atcagattgg agataaagaa   1740

aagctgggag gtaaactttc ctctgaagat aaggagacca tggaaaaagc tgtagaagaa   1800

aagattgaat ggctggaaag ccaccaagat gctgacattg aagacttcaa agctaagaag   1860

aaggaactgg aagaaattgt tcaaccaatt atcagcaaac tctatggaag tgcaggccct   1920

cccccaactg gtgaagagga tacagcagaa aaagatgagt tgtag                   1965
```

```
<210> SEQ ID NO 2
<211> LENGTH: 3399
<212> TYPE: DNA
<213> ORGANISM: Homo sapiens

<400> SEQUENCE: 2

atgccgcgcg ctccccgctg ccgagccgtg cgctccctgc tgcgcagcca ctaccgcgag     60

gtgctgccgc tggccacgtt cgtgcggcgc ctggggcccc agggctggcg gctggtgcag    120

cgcggggacc cggcggcttt ccgcgcgctg gtggcccagt gcctggtgtg cgtgccctgg    180

gacgcacggc cgcccccgc cgccccctcc ttccgccagg tgtcctgcct gaaggagctg    240

gtggcccgag tgctgcagag gctgtgcgag cgcggcgcga agaacgtgct ggccttcggc    300

ttcgcgctgc tggacggggc ccgcgggggc ccccccgagg ccttcaccac cagcgtgcgc    360

agctacctgc ccaacacggt gaccgacgca ctgcggggga gcggggcgtg gggcctgctg    420

ctgcgccgcg tgggcgacga cgtgctggtt cacctgctgg cacgctgcgc gctctttgtg    480

ctggtggctc ccagctgcgc ctaccaggtg tgcgggccgc cgctgtacca gctcggcgct    540

gccactcagg cccggccccc gccacacgct agtggacccc gaaggcgtct gggatgcgaa    600

cgggcctgga accatagcgt cagggaggcc ggggtccccc tgggcctgcc agccccgggt    660

gcgaggaggc gcgggggcag tgccagccga agtctgccgt tgcccaagag gcccaggcgt    720

ggcgctgccc ctgagccgga gcggacgccc gttgggcagg ggtcctgggc ccacccgggc    780

aggacgcgtg gaccgagtga ccgtggtttc tgtgtggtgt cacctgccag acccgccgaa    840

gaagccacct ctttggaggg tgcgctctct ggcacgcgcc actcccaccc atccgtgggc    900

cgccagcacc acgcgggccc cccatccaca tcgcggccac cacgtccctg ggacacgcct    960

tgtcccccgg tgtacgccga gaccaagcac ttcctctact cctcaggcga caaggagcag   1020

ctgcggccct ccttcctact cagctctctg aggcccagcc tgactggcgc tcggaggctc   1080

gtggagacca tctttctggg ttccaggccc tggatgccag ggactccccg caggttgccc   1140

cgcctgcccc agcgctactg gcaaatgcgg cccctgtttc tggagctgct tgggaaccac   1200

gcgcagtgcc cctacggggt gctcctcaag acgcactgcc cgctgcgagc tgcggtcacc   1260

ccagcagccg gtgtctgtgc ccgggagaag ccccagggct ctgtggcggc cccccgaggag   1320

gaggacacag acccccgtcg cctggtgcag ctgctccgcc agcacagcag cccctggcag   1380
```

-continued

```
gtgtacggct tcgtgcgggc ctgcctgcgc cggctggtgc ccccaggcct ctggggctcc   1440
aggcacaacg aacgccgctt cctcaggaac accaagaagt tcatctccct ggggaagcat   1500
gccaagctct cgctgcagga gctgacgtgg aagatgagcg tgcgggactg cgcttggctg   1560
cgcaggagcc caggggttgg ctgtgttccg gccgcagagc accgtctgcg tgaggagatc   1620
ctggccaagt tcctgcactg gctgatgagt gtgtacgtcg tcgagctgct caggtctttc   1680
ttttatgtca cggagaccac gtttcaaaag aacaggctct ttttctaccg gaagagtgtc   1740
tggagcaagt tgcaaagcat tggaatcaga cagcacttga agagggtgca gctgcgggag   1800
ctgtcggaag cagaggtcag gcagcatcgg gaagccaggc ccgccctgct gacgtccaga   1860
ctccgcttca tccccaagcc tgacgggctg cggccgattg tgaacatgga ctacgtcgtg   1920
ggagccagaa cgttccgcag agaaaagagg gccgagcgtc tcacctcgag ggtgaaggca   1980
ctgttcagcg tgctcaacta cgagcgggcg cggcgccccg gcctcctggg cgcctctgtg   2040
ctgggcctgg acgatatcca cagggcctgg cgcaccttcg tgctgcgtgt gcgggcccag   2100
gacccgccgc ctgagctgta ctttgtcaag gtggatgtga cgggcgcgta cgacaccatc   2160
ccccaggaca ggctcacgga ggtcatcgcc agcatcatca aaccccagaa cacgtactgc   2220
gtgcgtcggt atgccgtggt ccagaaggcc gcccatgggc acgtccgcaa ggccttcaag   2280
agccacgtct ctaccttgac agacctccag ccgtacatgc gacagttcgt ggctcacctg   2340
caggagacca gcccgctgag ggatgccgtc gtcatcgagc agagctcctc cctgaatgag   2400
gccagcagtg gcctcttcga cgtcttccta cgcttcatgt gccaccacgc cgtgcgcatc   2460
aggggcaagt cctacgtcca gtgccagggg atcccgcagg gctccatcct ctccacgctg   2520
ctctgcagcc tgtgctacgg cgacatggag aacaagctgt ttgcggggat tcggcgggac   2580
gggctgctcc tgcgtttggt ggatgatttc ttgttggtga cacctcacct cacccacgcg   2640
aaaaccttcc tcaggaccct ggtccgaggt gtccctgagt atggctgcgt ggtgaacttg   2700
cggaagacag tggtgaactt ccctgtagaa gacgaggccc tgggtggcac ggcttttgtt   2760
cagatgccgg cccacggcct attcccctgg tgcggcctgc tgctggatac ccggaccctg   2820
gaggtgcaga gcgactactc cagctatgcc cggacctcca tcagagccag tctcaccttc   2880
aaccgcggct tcaaggctgg gaggaacatg cgtcgcaaac tctttggggt cttgcggctg   2940
aagtgtcaca gcctgtttct ggatttgcag gtgaacagcc tccagacggt gtgcaccaac   3000
atctacaaga tcctcctgct gcaggcgtac aggtttcacg catgtgtgct gcagctccca   3060
tttcatcagc aagtttggaa gaaccccaca tttttcctgc gcgtcatctc tgacacggcc   3120
tccctctgct actccatcct gaaagccaag aacgcaggga tgtcgctggg ggccaagggc   3180
gccgccggcc ctctgccctc cgaggccgtg cagtggctgt gccaccaagc attcctgctc   3240
aagctgactc gacaccgtgt cacctacgtg ccactcctgg ggtcactcag gacagcccag   3300
acgcagctga gtcggaagct cccggggacg acgctgactg ccctggaggc cgcagccaac   3360
ccggcactgc cctcagactt caagaccatc ctggactga                          3399
```

<210> SEQ ID NO 3
<211> LENGTH: 1491
<212> TYPE: DNA
<213> ORGANISM: Human adenovirus type 5

<400> SEQUENCE: 3
atggagcgaa gaaacccatc tgagcgggga gtacctgctg gattttctgg ccatgcatct 60
gtggagagcg gttgtgagac acaagaatcg cctgctactg ttgtcttccg tccgcccggc 120
gataataccg acggaggagc agcagcagca gcaggaggaa gccaggcggc ggcggcagga 180
gcagagccca tggaacccga gagccggcct ggaccctcgg gaatgaatgt tgtacaggtg 240
gctgaactgt atccagaact gagacgcatt ttgacaatta cagaggatgg gcaggggcta 300
aagggggtaa agagggagcg gggggcttgt gaggctacag aggaggctag gaatctagct 360
tttagcttaa tgaccagaca ccgtcctgag tgtattactt ttcaacagat caaggataat 420
tgcgctaatg agcttgatct gctggcgcag aagtattcca tagagcagct gaccacttac 480
tggctgcagc caggggatga ttttgaggag gctattaggg tatatgcaaa ggtggcactt 540
aggccagatt gcaagtacaa gatcagcaaa cttgtaaata tcaggaattg ttgctacatt 600
tctgggaacg gggccgaggt ggagatagat acggaggata gggtggcctt tagatgtagc 660
atgataaata tgtggccggg ggtgcttggc atggacgggg tggttattat gaatgtaagg 720
tttactggcc ccaattttag cggtacggtt ttcctggcca ataccaacct tatcctacac 780
ggtgttagct tctatgggtt taacaatacc tgtgtggaag cctggaccga tgtaagggtt 840
cggggctgtg ccttttactg ctgctggaag ggggtggtgt gtcgccccaa aagcagggct 900
tcaattaaga aatgcctctt tgaaaggtgt accttgggta tcctgtctga gggtaactcc 960
agggtgcgcc acaatgtggc ctccgactgt ggttgcttca tgctagtgaa aagcgtggct 1020
gtgattaagc ataacatggt atgtggcaac tgcgaggaca gggcctctca gatgctgacc 1080
tgctcggacg gcaactgtca cctgctgaag accattcacg tagccagcca ctctcgcaag 1140
gcctggccag tgtttgagca taacatactg acccgctgtt ccttgcattt gggtaacagg 1200
aggggggtgt tcctacctta ccaatgcaat ttgagtcaca ctaagatatt gcttgagccc 1260
gagagcatgt ccaaggtgaa cctgaacggg gtgtttgaca tgaccatgaa gatctggaag 1320
gtgctgaggt acgatgagac ccgcaccagg tgcagaccct gcgagtgtgg cggtaaacat 1380
attaggaacc agcctgtgat gctggatgtg accgaggagc tgaggcccga tcacttggtg 1440
ctggcctgca cccgcgctga gtttggctct agcgatgaag atacagattg a 1491

<210> SEQ ID NO 4
<211> LENGTH: 29
<212> TYPE: DNA
<213> ORGANISM: Artificial Sequence
<220> FEATURE:
<223> OTHER INFORMATION: BamHI/NotI forward primer

<400> SEQUENCE: 4
gcggatccat ggagcgaaga aacccatct 29

<210> SEQ ID NO 5
<211> LENGTH: 28
<212> TYPE: DNA
<213> ORGANISM: Artificial Sequence
<220> FEATURE:
<223> OTHER INFORMATION: BamHI/NotI reverse primer

<400> SEQUENCE: 5
cggccgctca atctgtatct tcatcgct 28

<210> SEQ ID NO 6

<211> LENGTH: 30
<212> TYPE: DNA
<213> ORGANISM: Artificial Sequence
<220> FEATURE:
<223> OTHER INFORMATION: HindIII forward primer

<400> SEQUENCE: 6
gtacaagctt atgactacgt ccggcgttcc 30

<210> SEQ ID NO 7
<211> LENGTH: 30
<212> TYPE: DNA
<213> ORGANISM: Artificial Sequence
<220> FEATURE:
<223> OTHER INFORMATION: XbaI reverse primer

<400> SEQUENCE: 7
cacctctaga ctacatgggg gtagagtcat 30

<210> SEQ ID NO 8
<211> LENGTH: 30
<212> TYPE: DNA
<213> ORGANISM: Artificial Sequence
<220> FEATURE:
<223> OTHER INFORMATION: CMV30

<400> SEQUENCE: 8
aatgtcgtaa taaccccgcc ccgttgacgc 30

<210> SEQ ID NO 9
<211> LENGTH: 30
<212> TYPE: DNA
<213> ORGANISM: Artificial Sequence
<220> FEATURE:
<223> OTHER INFORMATION: XbaI sense primer

<400> SEQUENCE: 9
ttcatctaga atggagcgaa gaaacccatc 30

<210> SEQ ID NO 10
<211> LENGTH: 30
<212> TYPE: DNA
<213> ORGANISM: Artificial Sequence
<220> FEATURE:
<223> OTHER INFORMATION: HindIII antisense primer

<400> SEQUENCE: 10
gacgaagctt tcaatctgta tcttcatcgc 30

<210> SEQ ID NO 11
<211> LENGTH: 25
<212> TYPE: DNA
<213> ORGANISM: Artificial Sequence
<220> FEATURE:
<223> OTHER INFORMATION: hCMV forward primer

<400> SEQUENCE: 11
gggaggtcta tataagcaga gctcg 25

<210> SEQ ID NO 12
<211> LENGTH: 25
<212> TYPE: DNA
<213> ORGANISM: Artificial Sequence
<220> FEATURE:
<223> OTHER INFORMATION: pCA14 SV40 reverse primer

<400> SEQUENCE: 12
catgatcgat gctagacgat ccaga 25

<210> SEQ ID NO 13
<211> LENGTH: 25
<212> TYPE: PRT
<213> ORGANISM: Artificial Sequence
<220> FEATURE:
<223> OTHER INFORMATION: N terminus of E1B55K

<400> SEQUENCE: 13

Met Glu Arg Arg Asn Pro Ser Glu Arg Gly Val Pro Ala Gly Phe Ser
1 5 10 15

Gly His Ala Ser Val Glu Ser Gly Cys
20 25

<210> SEQ ID NO 14
<211> LENGTH: 40
<212> TYPE: DNA
<213> ORGANISM: Artificial Sequence
<220> FEATURE:
<223> OTHER INFORMATION: E1B55K In-fusion EcoRI sense primer

<400> SEQUENCE: 14
ccctcgtaaa gaattcatgg agcgaagaaa cccatctgag 40

<210> SEQ ID NO 15
<211> LENGTH: 40
<212> TYPE: DNA
<213> ORGANISM: Artificial Sequence
<220> FEATURE:
<223> OTHER INFORMATION: E1B55K In-fusion BamHI antisense primer

<400> SEQUENCE: 15
gaggtggtct ggatcctcaa tctgtatctt catcgctaga 40

<210> SEQ ID NO 16
<211> LENGTH: 26
<212> TYPE: DNA
<213> ORGANISM: Artificial Sequence
<220> FEATURE:
<223> OTHER INFORMATION: XbaI Forward primer

<400> SEQUENCE: 16
gattctcgag atgaagctct ccctgg 26

<210> SEQ ID NO 17
<211> LENGTH: 26
<212> TYPE: DNA
<213> ORGANISM: Artificial Sequence
<220> FEATURE:
<223> OTHER INFORMATION: XbaI Reverse primer

<400> SEQUENCE: 17
ggcctctaga ctacaactca tctttt 26

<210> SEQ ID NO 18
<211> LENGTH: 62
<212> TYPE: DNA
<213> ORGANISM: Artificial Sequence
<220> FEATURE:
<223> OTHER INFORMATION: pLNCX neo Top strand

<400> SEQUENCE: 18
agcttcacgt gccagcacag tggcggccgc tcgagtcgac gggcccgttt aaacgttaac 60
at 62

<210> SEQ ID NO 19
<211> LENGTH: 60
<212> TYPE: DNA
<213> ORGANISM: Artificial Sequence
<220> FEATURE:
<223> OTHER INFORMATION: pLNCX neo Bottom strand

<400> SEQUENCE: 19
cgatgttaac gtttaaacgg gcccgtcgac tcgagcggcc gccactgtgc tggcacgtga 60

<210> SEQ ID NO 20
<211> LENGTH: 20
<212> TYPE: DNA
<213> ORGANISM: Artificial Sequence
<220> FEATURE:
<223> OTHER INFORMATION: E4 ORF Forward primer

<400> SEQUENCE: 20
cgtggtcaaa ctctacagcc 20

<210> SEQ ID NO 21
<211> LENGTH: 20
<212> TYPE: DNA
<213> ORGANISM: Artificial Sequence
<220> FEATURE:
<223> OTHER INFORMATION: E4 ORF Reverse primer

<400> SEQUENCE: 21
gcatgagcat gactacgatg 20

<210> SEQ ID NO 22
<211> LENGTH: 912
<212> TYPE: DNA
<213> ORGANISM: artificial sequence
<220> FEATURE:
<223> OTHER INFORMATION: Flag-E4orf6

<400> SEQUENCE: 22
gactacaaag acgatgacga caagcttatg actacgtccg gcgttccatt tggcatgaca 60
ctacgaccaa cacgatctcg gttgtctcgg cgcactccgt acagtaggga tcgtctacct 120
ccttttgaga cagaaacccg cgctaccata ctggaggatc atccgctgct gcccgaatgt 180
aacactttga caatgcacaa cgtgagttac gtgcgaggtc ttccctgcag tgtgggattt 240
acgctgattc aggaatgggt tgttccctgg gatatggttc taacgcggga ggagcttgta 300
atcctgagga agtgtatgca cgtgtgcctg tgttgtgcca acattgatat catgacgagc 360
atgatgatcc atggttacga gtcctgggct ctccactgtc attgttccag tcccggttcc 420
ctgcagtgta tagccggcgg gcaggttttg gccagctggt ttaggatggt ggtggatggc 480
gccatgttta atcagaggtt tatatggtac cgggaggtgg tgaattacaa catgccaaaa 540
gaggtaatgt ttatgtccag cgtgtttatg aggggtcgcc acttaatcta cctgcgcttg 600
tggtatgatg gccacgtggg ttctgtggtc cccgccatga gctttggata cagcgccttg 660
cactgtggga ttttgaacaa tattgtggtg ctgtgctgca gttactgtgc tgatttaagt 720
gagatcaggg tgcgctgctg tgcccggagg acaaggcgcc ttatgctgcg ggcggtgcga 780
atcatcgctg aggagaccac tgccatgttg tattcctgca ggacggagcg gcggcggcag 840
cagtttattc gcgcgctgct gcagcaccac cgccctatcc tgatgcacga ttatgactct 900
acccccatgt ag 912

<210> SEQ ID NO 23
<211> LENGTH: 1196
<212> TYPE: DNA
<213> ORGANISM: Artificial Sequence
<220> FEATURE:
<223> OTHER INFORMATION: pflag-CMV2-E4orf6

<400> SEQUENCE: 23
aaccgtcaga attgatctac catggactac aaagacgatg acgacaagct tatgactacg 60
tccggcgttc catttggcat gacactacga ccaacacgat ctcggttgtc tcggcgcact 120
ccgtacagta gggatcgtct acctcctttt gagacagaaa cccgcgctac catactggag 180
gatcatccgc tgctgcccga atgtaacact ttgacaatgc acaacgtgag ttacgtgcga 240
ggtcttccct gcagtgtggg atttacgctg attcaggaat gggttgttcc ctgggatatg 300
gttctaacgc gggaggagct tgtaatcctg aggaagtgta tgcacgtgtg cctgtgttgt 360
gccaacattg atatcatgac gagcatgatg atccatggtt acgagtcctg ggctctccac 420
tgtcattgtt ccagtcccgg ttccctgcag tgtatagccg gcgggcaggt tttggccagc 480
tggtttagga tggtggtgga tggcgccatg tttaatcaga ggtttatatg gtaccgggag 540
gtggtgaatt acaacatgcc aaaagaggta atgtttatgt ccagcgtgtt tatgaggggt 600
cgccacttaa tctacctgcg cttgtggtat gatggccacg tgggttctgt ggtccccgcc 660
atgagctttg gatacagcgc cttgcactgt gggattttga acaatattgt ggtgctgtgc 720
tgcagttact gtgctgattt aagtgagatc agggtgcgct gctgtgcccg gaggacaagg 780
cgccttatgc tgcgggcggt gcgaatcatc gctgaggaga ccactgccat gttgtattcc 840
tgcaggacgg agcggcggcg gcagcagttt attcgcgcgc tgctgcagca ccaccgccct 900
atcctgatgc acgattatga ctctaccccc atgtagtcta gaggatcccg ggtggcatcc 960
ctgtgacccc tccccagtgc ctctcctggc cctggaagtt gccactccag tgcccaccag 1020
ccttgtccta ataaaattaa gttgcatcat tttgtctgac taggtgtcct tctataatat 1080
tatggggtgg aggggggggg tatggaacca aggggcaagt tgggaaaaaa acctgaaggg 1140
cctgcgggtc ttattgggaa ccaaactggg agtgcagtgg accaattttg ggttcc 1196

<210> SEQ ID NO 24
<211> LENGTH: 960
<212> TYPE: DNA
<213> ORGANISM: Artificial Sequence
<220> FEATURE:
<223> OTHER INFORMATION: pCA14-E1B55K forward

<400> SEQUENCE: 24
aagacaccgg gaccgatcca gcctggggat cttcgagtcg agggatccct cgagtctaga 60
atggagcgaa gaaacccatc tgagcgggga gtacctgctg gattttctgg ccatgcatct 120
gtggagagcg gttgtgagac acaagaatcg cctgctactg ttgtcttccg tccgcccggc 180
gataataccg acggaggagc agcagcagca gcaggaggaa gccaggcggc ggcggcagga 240
gcagagccca tggaacccga gagccggcct ggaccctcgg gaatgaatgt tgtacaggtg 300
gctgaactgt atccagaact gagacgcatt ttgacaatta cagaggatgg gcaggggcta 360
aagggggtaa agagggagcg gggggcttgt gaggctacag aggaggctag gaatctagct 420
tttagcttaa tgaccagaca ccgtcctgag tgtattactt ttcaacagat caaggataat 480
tgcgctaatg agcttgatct gctggcgcag aagtattcca tagagcagct gaccacttac 540
tggctgcagc caggggatga ttttgaggag gctattaggg tatatgcaaa ggtggcactt 600
aggccagatt gcaagtacaa gatcagcaaa cttgtaaata tcaggaattg ttgctacatt 660
tctgggaacg gggccgaggt ggagatagat acggaggata gggtggcctt tagatgtagc 720
atgataaata tgtggccggg ggtgcttggc atggacgggg tggttattat gaatgtaagg 780
tttactggcc ccaattttag cggtacggtt ttcctggcca ataccaacct tatcctacac 840
ggtgttagct tctatgggtt taacaatacc tgtgtggaag cctggaccga tgtaagggtt 900
cggggctgtg ccttttactg ctgctggaag gggggtggtgt gtcgccccaa aagcagggct 960

<210> SEQ ID NO 25
<211> LENGTH: 1017
<212> TYPE: DNA
<213> ORGANISM: Artificial Sequence
<220> FEATURE:
<223> OTHER INFORMATION: pCA14-E1B55K-reverse

<400> SEQUENCE: 25
tttggtccaa ccggggatga tttgaggggg cttttgggtt tttgcaaagg tgcccttagg 60
ccagattgca attacaaaat cagcaaactt gtaaatttca ggaattgttg ctacatttct 120
gggaacgggg ccgaggtgga gatagatacg gaggataggg tggcctttag atgtagcatg 180
ataaatatgt ggccgggggt gcttggcatg gacggggtgg ttattatgaa tgtaaggttt 240
actggcccca attttagcgg tacggttttc ctggccaata ccaaccttat cctacacggt 300
gttagcttct atgggtttaa caatacctgt gtggaagcct ggaccgatgt aagggttcgg 360
ggctgtgcct tttactgctg ctggaagggg gtggtgtgtc gccccaaaag cagggcttca 420
attaagaaat gcctctttga aaggtgtacc ttgggtatcc tgtctgaggg taactccagg 480
gtgcgccaca atgtggcctc cgactgtggt tgcttcatgc tagtgaaaag cgtggctgtg 540
attaagcata acatggtatg tggcaactgc gaggacaggg cctctcagat gctgacctgc 600
tcggacggca actgtcacct gctgaagacc attcacgtag ccagccactc tcgcaaggcc 660
tggccagtgt ttgagcataa catactgacc cgctgttcct tgcatttggg taacaggagg 720
ggggtgttcc taccttacca atgcaatttg agtcacacta agatattgct tgagcccgag 780
agcatgtcca aggtgaacct gaacggggtg tttgacatga ccatgaagat ctggaaggtg 840
ctgaggtacg atgagacccg caccaggtgc agaccctgcg agtgtggcgg taaacatatt 900
aggaaccagc ctgtgatgct ggatgtgacc gaggagctga ggcccgatca cttggtgctg 960
gcctgcaccc gcgctgagtt tggctctagc gatgaagata cagattgaaa gcttgtc 1017

<210> SEQ ID NO 26
<211> LENGTH: 1172
<212> TYPE: DNA
<213> ORGANISM: Artificial Sequence
<220> FEATURE:
<223> OTHER INFORMATION: primer E1B55K In-fusion EcoRI sense

<400> SEQUENCE: 26
ccggggggca gtacctgctg gattctctgg ccatgcatct gtggagagcg gttgtgagac 60
acaagaatcg cctgctactg ttgtcttccg tccgcccggc gataataccg acggaggagc 120
agcagcagca gcaggaggaa gccaggcggc ggcggcagga gcagagccca tggaacccga 180

-continued

```
gagccggcct ggaccctcgg gaatgaatgt tgtacaggtg gctgaactgt atccagaact    240

gagacgcatt ttgacaatta cagaggatgg gcaggggcta aagggggtaa agagggagcg    300

gggggcttgt gaggctacag aggaggctag gaatctagct tttagcttaa tgaccagaca    360

ccgtcctgag tgtattactt ttcaacagat caaggataat tgcgctaatg agcttgatct    420

gctggcgcag aagtattcca tagagcagct gaccacttac tggctgcagc caggggatga    480

ttttgaggag gctattaggg tatatgcaaa ggtggcactt aggccagatt gcaagtacaa    540

gatcagcaaa cttgtaaata tcaggaattg ttgctacatc tctgggaacg gggccgaggt    600

ggagatagat acggaggata gggtggcctt tagatgtagc atgataaata tgtggccggg    660

ggtgcttggc atggacgggg tggttattat gaatgtaagg tttactggcc ccaattttag    720

cggtacggtt ttcctggcca ataccaacct tatcctacac ggtgttagct tctatgggtt    780

taacaatacc tgtgtggaag cctggaccga tgtaagggtt cggggctgtg ccttttactg    840

ctgctggaag ggggtggtgt gtcgccccaa aagcagggct tcaattaaga aatgcctctt    900

tgaaaggtgt accttgggta tcctgtctga gggtaactcc agggtgcgcc acaatgtggc    960

ctccgactgt ggttgcttca tgctagtgaa aagcgtggct gtgattaagc ataacatggt   1020

atgtggcaac tgcgaggaca gggcctctca gatgctgacc tgctcggacg gcaactgtca   1080

cctgctgaag acattcacgt agccagccct ttcgcaaggc tggccagggt tgagcatacc   1140

tactgacccc ctgttccttg ctttgggaaa aa                                 1172
```

<210> SEQ ID NO 27
<211> LENGTH: 686
<212> TYPE: DNA
<213> ORGANISM: Artificial Sequence
<220> FEATURE:
<223> OTHER INFORMATION: primer: E1B55K internal primer

<400> SEQUENCE: 27

```
acctgtaatt tgtttatttg ggcgtaggtc gggcgtgctt ttactgctgc tggaaggggg     60

tggtgtgtcg ccccaaaagc agggcttcaa ttaagaaatg cctctttgaa aggtgtacct    120

tgggtatcct gtctgagggt aactccaggg tgcgccacaa tgtggcctcc gactgtggtt    180

gcttcatgct agtgaaaagc gtggctgtga ttaagcataa catggtatgt ggcaactgcg    240

aggacagggc ctctcagatg ctgacctgct cggacggcaa ctgtcacctg ctgaagacca    300

ttcacgtagc cagccactct cgcaaggcct ggccagtgtt tgagcataac atactgaccc    360

gctgttcctt gcatttgggt aacaggaggg ggtgttcct accttaccaa tgcaatttga    420

gtcacactaa gatattgctt gagcccgaga gcatgtccaa ggtgaacctg aacggggtgt    480

ttgacatgac catgaagatc tggaaggtgc tgaggtacga tgagacccgc accaggtgca    540

gaccctgcga gtgtggcggt aaacatatta ggaaccagcc tgtgatgctg gatgtgaccg    600

aggagctgag gcccgatcac ttggtgctgg cctgcacccg cgctgagttt ggctctagcg    660

atgaagatac agattgagga tccaga                                         686
```

<210> SEQ ID NO 28
<211> LENGTH: 483
<212> TYPE: DNA
<213> ORGANISM: Artificial Sequence
<220> FEATURE:
<223> OTHER INFORMATION: E1B55K 5' near internal reverse primer

<400> SEQUENCE: 28
aaagaattca tggagcgaag aaacccatct gagcggggag tacctgctgg attctctggc 60
catgcatctg tggagagcgg ttgtgagaca caagaatcgc ctgctactgt tgtcttccgt 120
ccgcccggcg ataataccga cggaggagca gcagcagcag caggaggaag ccaggcggcg 180
gcggcaggag cagagcccat ggaacccgag agccggcctg gaccctcggg aatgaatgtt 240
gtacaggtgg ctgaactgta tccagaactg agacgcattt tgacaattac agaggatggg 300
caggggctaa agggggtaaa gagggagcgg ggggcttgtg aggctacaga ggaggctagg 360
aatctagctt ttagcttaat gaccagacac cgtcctgagt gtattacttt tcaacagatc 420
aaggataatt gcgctaatga gctgatctgc gcgcagacgc gccaacaaaa caagagtcca 480
gtc 483

<210> SEQ ID NO 29
<211> LENGTH: 1246
<212> TYPE: DNA
<213> ORGANISM: Artificial Sequence
<220> FEATURE:
<223> OTHER INFORMATION: primer:E1B55K In-fusion BamHI antisense

<400> SEQUENCE: 29
aaaggatggc agggctaaag ggtaaagag gagcgggggc ttggaggcta cagaggaggc 60
taggaatcta gcttttagct taatgaccag acaccgtcct gagtgtatta cttttcaaca 120
gatcaaggat aattgcgcta atgagcttga tctgctggcg cagaagtatt ccatagagca 180
gctgaccact tactggctgc agccagggga tgattttgag gaggctatta gggtatatgc 240
aaaggtggca cttaggccag attgcaagta caagatcagc aaacttgtaa atatcaggaa 300
ttgttgctac atctctggga acggggccga ggtggagata gatacggagg atagggtggc 360
ctttagatgt agctctggga acggggccga ggtggagata gatacggagg atagggtggc 420
ctttagatgt agctctggga acggggccga ggtggagata gatacggagg atagggtggc 480
ctttagatgt agctttactg gccccaattt tagcggtacg gttttcctgg ccaataccaa 540
ccttatccta cacggtgtta gcttctatgg gtttaacaat acctgtgtgg aagcctggac 600
cgatgtaagg gttcggggct gtgcctttta ctgctgctgg aagggggtgg tgtgtcgccc 660
caaaagcagg gcttcaatta agaaatgcct ctttgaaagg tgtaccttgg gtatcctgtc 720
tgagggtaac tccagggtgc gccacaatgt ggcctccgac tgtggttgct tcatgctagt 780
gaaaagcgtg gctgtgatta agcataacat ggtatgtggc aactgcgagg acagggcctc 840
tcagatgctg acctgctcgg acggcaactg tcacctgctg aagaccattc acgtagccag 900
ccactctcgc aaggcctggc cagtgtttga gcataacata ctgacccgct gttccttgca 960
tttgggtaac aggagggggg tgttcctacc ttaccaatgc aatttgagtc acactaagat 1020
attgcttgag cccgagagca tgtccaaggt gaacctgaac ggggtgtttg acatgaccat 1080
gaagatctgg aaggtgctga ggtacgatga gacccgcacc aggtgcagac cctgcgagtg 1140
tggcggtaaa catattagga accagcctgt gatgctggat gtgaccgagg agctgaggcc 1200
cgatcacttg gtgctggcct gcacccgcgc tgagtttggc ccccgt 1246

<210> SEQ ID NO 30
<211> LENGTH: 995
<212> TYPE: DNA
<213> ORGANISM: Artificial Sequence
<220> FEATURE:

-continued

<223> OTHER INFORMATION: pcDNA3.1 GRP78 forward

<400> SEQUENCE: 30
tggtggaatt ctgcagatat ccagcacagt ggcggccgct cgagatgaag ctctccctgg 60
tggccgcgat gctgctgctg ctcagcgcgg cgcgggccga ggaggaggac aagaaggagg 120
acgtgggcac ggtggtcggc atcgacctgg ggaccaccta ctcctgcgtc ggcgtgttca 180
agaacggccg cgtggagatc atcgccaacg atcagggcaa ccgcatcacg ccgtcctatg 240
tcgccttcac tcctgaaggg gaacgtctga ttggcgatgc cgccaagaac cagctcacct 300
ccaaccccga gaacacggtc tttgacgcca agcggctcat cggccgcacg tggaatgacc 360
cgtctgtgca gcaggacatc aagttcttgc cgttcaaggt ggttgaaaag aaaactaaac 420
catacattca agttgatatt ggaggtgggc aaacaaagac atttgctcct gaagaaattt 480
ctgccatggt tctcactaaa atgaaagaaa ccgctgaggc ttatttggga aagaaggtta 540
cccatgcagt tgttactgta ccagcctatt ttaatgatgc ccaacgccaa gcaaccaaag 600
acgctggaac tattgctggc ctaaatgtta tgaggatcat caacgagcct acggcagctg 660
ctattgctta tggcctggat aagagggagg gggagaagaa catcctggtg tttgacctgg 720
gtggcggaac cttcgatgtg tctcttctca ccattgacaa tggtgtcttc gaagttgtgg 780
ccactaatgg agatactcat ctgggtggag aagactttga ccagcgtgtc atggaacact 840
tcatcaaact gtacaaaaag aagacgggca aagatgtcag gaaagacaat agagctgtgc 900
agaaactccg gcgcgaggta gaaaaggcca aacgggccct gtcttctcag catcaagcaa 960
gaattgaaat tgagtccttc tatgaaggag aagac 995

<210> SEQ ID NO 31
<211> LENGTH: 1046
<212> TYPE: DNA
<213> ORGANISM: Artificial Sequence
<220> FEATURE:
<223> OTHER INFORMATION: pcDNA3.1 GRP78 reverse

<400> SEQUENCE: 31
tctatgaagg agaagacttt tctgagaccc tgactcgggc caaatttgaa gagctcaaca 60
tggatctgtt ccggtctact atgaagcccg tccagaaagt gttggaagat tctgatttga 120
agaagtctga tattgatgaa attgttcttg ttggtggctc gactcgaatt ccaaagattc 180
agcaactggt taaagagttc ttcaatggca aggaaccatc ccgtggcata aacccagatg 240
aagctgtagc gtatggtgct gctgtccagg ctggtgtgct ctctggtgat caagatacag 300
gtgacctggt actgcttgat gtatgtcccc ttacacttgg tattgaaact gtgggaggtg 360
tcatgaccaa actgattcca aggaacacag tggtgcctac caagaagtct cagatctttt 420
ctacagcttc tgataatcaa ccaactgtta caatcaaggt ctatgaaggt gaaagacccc 480
tgacaaaaga caatcatctt ctgggtacat ttgatctgac tggaattcct cctgctcctc 540
gtggggtccc acagattgaa gtcacctttg agatagatgt gaatggtatt cttcgagtga 600
cagctgaaga caagggtaca gggaacaaaa ataagatcac aatcaccaat gaccagaatc 660
gcctgacacc tgaagaaatc gaaaggatgg ttaatgatgc tgagaagttt gctgaggaag 720
acaaaaagct caaggagcgc attgatacta gaaatgagtt ggaaagctat gcctattctc 780
taaagaatca gattggagat aaagaaaagc tgggaggtaa actttcctct gaagataagg 840
agaccatgga aaaagctgta gaagaaaaga ttgaatggct ggaaagccac caagatgctg 900
acattgaaga cttcaaagct aagaagaagg aactggaaga aattgttcaa ccaattatca 960

-continued

```
gcaaactcta tggaagtgca ggccctcccc caactggtga agaggataca gcagaaaaag   1020

atgagttgta gtctagagtc ccgtaa                                        1046
```

MESENCHYMAL STEM CELLS THAT ENABLE TUMOR TARGETING IMPROVEMENT AND VIRUS MASS-PRODUCTION

REFERENCE TO AN ELECTRONIC SEQUENCE LISTING

The content of the electronic sequence listing submitted on Mar. 9, 2023, as a text file named "G22U18C0815P_US_amended.txt" created on Feb. 15, 2023, and having a size of 26.7 KB, is herein incorporated by reference in its entirety pursuant to 37 C.F.R. § 1.52 (e) (5).

TECHNICAL FIELD

The present invention relates to the preparation of mesenchymal stem cells, which are for the proliferation of viral vectors and viruses, and enable virus production and release timing control such that tumor targeting can be improved and viruses can be mass-produced.

BACKGROUND ART

As it was reported that in the case of vesicular stomatitis virus, the rate of reaching a tumor was 0.01% within 24 hours compared to an intravenously administered virus (input virus) [Non-Patent Document 1], and the biggest constraint was the very low efficiency of delivery to a target during intravenous injection of the virus.

Since the majority of mortality in cancer patients is caused by metastatic tumors, it is essential that there is tropism to tumors and a sufficient amount of tumor-killing (oncolytic) virus be delivered to tumors relative to the administered virus.

However, upon intravascular injection, most viruses are absorbed by Kupffer cells in the liver, rapidly cleared by mechanical deposition, easily destroyed by intravascular virus-neutralizing antibodies and complements, and further, there is a problem in that the proportion of intravascular viruses released at tumor sites is considerably low. Due to these problems, in particular, the introduction of an adenovirus alone by intravenous injection could not be expected to be effective.

Solutions to the above problems include genetic modification of viruses, the introduction of nanotechnology, the use of mesenchymal stem cells with tropism to tumor sites, and the like. In particular, around 2010, research had been conducted on tumor-tropic cells such as mesenchymal stem cells [Non-Patent Document 2]. However, although mesenchymal stem cells (MSCs) have many advantages in ethical and technical convenience, low immunogenicity, and genetic stability, problems of decreases in adenovirus infection rate and replication rate for MSCs have emerged.

In order to become a carrier and amplifier of an oncolytic adenovirus, infection and replication with respect to MSCs need to be maintained at a certain level or higher, but these problems, the present inventors prepared a genetically modified MSC to get a patent registration in Korea [Patent Document 2]. However, it was confirmed that passage extension was not easy for these MSCs, and the state of a cell line deteriorated as the passage number increased.

In addition, Non-Patent Document 3 confirmed that the intravascular delivery of MSCs for the delivery of oncolytic viruses is accessible for treating multiple brain tumors, but there are problems such as the tumor growth potential of MSCs.

Meanwhile, a technique of constructing a platform that temporarily releases a virus whose production has increased at desired time points after the virus has migrated to tumors has been reported [Non-Patent Document 4]. When an MSC is used as a viral vector, carrier cells (MSCs) loaded with genes that induce cell death are quickly lysed before reaching a tumor site to release the virus, so the technique raised various problems which may be caused by the release of the virus, above all, safety problems, and the like.

Therefore, in reality, most deaths from cancer are caused by recurrence and metastasis, and there is a need for a technique capable of overcoming the major obstacles which have not yet been solved in the treatment of tumors with oncolytic viruses.

RELATED ART DOCUMENTS

Patent Documents (Patent Document 1) Korean Patent No. 10-2169798 (Oct. 26, 2020)

Non-Patent Documents (Non-Patent Document 1) Silva, N et al., Double trouble for tumors: Exploiting the tumor microenvironment to enhance anticancer effect of oncolytic viruses, Cytokine & Growth Factor Reviews 21: 135, 2010

(Non-Patent Document 2) Xia, X et al, Mesenchymal stem cells as carriers and amplifiers in CRAd delivery to tumors, Molecular Cancer 10: 134, 2011

(Non-Patent Document 3) Kerrigan BCP, Shimizu Y, Andreeff M, Lang FF. Mesenchymal stromal cells for the delivery of oncolytic viruses in gliomas. Cytotherapy 2017: 19:445-457

(Non-Patent Document 4) Nakashima H, Kaur 3, Chiocca EA. Directing systemic oncolytic viral delivery to tumors via carrier cells. Cytokine Growth Factor Rev 2010: 21:119-126

DISCLOSURE

Technical Problem

Thus, the present inventors have conducted studies and made efforts to solve the above-described problems, and as a result, developed mesenchymal stem cells capable of controlling the timing of virus production and release to improve the tumor targeting of mesenchymal stem cells for the proliferation of viral vectors and viruses and to enable the mass production of viruses, thereby completing the present invention.

Accordingly, an object of the present invention is to provide mesenchymal stem cells for delivering an oncolytic virus, having improved tumor-targeting ability, into which a glucose regulated protein 78 (GRP78) gene is introduced.

Further, another object of the present invention is to provide mesenchymal stem cells for delivering an oncolytic virus into which an E1B55K gene is introduced such that the expression thereof is induced by an expression inducer.

In addition, still another object of the present invention is to provide mesenchymal stem cells for delivering an oncolytic virus, including a glucose regulated protein 78 (GR- P78) gene and an E1B55K, in which the E1B55K is expressed by an expression inducer.

Furthermore, yet another object of the present invention is to provide a composition for delivering an anticancer gene, including the mesenchymal stem cells and the oncolytic virus.

Further, yet another object of the present invention is to provide an anticancer pharmaceutical composition including the mesenchymal stem cells and the oncolytic virus.

In addition, yet another object of the present invention is to provide a composition for diagnosing cancer, including the mesenchymal stem cells and the oncolytic virus.

Furthermore, yet another object of the present invention is to provide a method for treating cancer, the method including: administering a therapeutically effective amount of a pharmaceutical composition including the mesenchymal stem cells and the oncolytic virus to a subject.

Technical Solution

The three major difficulties posed by tumor treatment methods by a virus alone are as follows.

First, destruction by circulating antiviral antibodies against an oncolytic adenovirus, second, non-specific adsorption by other non-tumor tissues such as liver and spleen, and third, viral outflow from blood vessels to tumor sites rarely occurs.

In order to overcome these fundamental problems of virotherapy, mesenchymal stem cells were used as a cell carrier to facilitate the systemic blood transport of oncolytic viruses, and in addition to virus delivery, a genetically modified mesenchymal stem cell line (MSC) was developed for effective anti-tumor action caused by a large amount of virus produced during migration to a target tumor site.

The present invention relates to the preparation of mesenchymal stem cells, which are for the proliferation of viral vectors and viruses, and enable virus production and release timing control such that tumor targeting can be improved and viruses can be mass-produced.

Advantageous Effects

Since the majority of mortality in cancer patients is due to metastatic tumors, the migration to tumors relative to the administered virus and the existing adenoviral replication rate reduction in MSCs were remarkably improved such that a sufficient amount of an oncolytic virus could be delivered to tumors, and simultaneously, MSCs with improved tumor targeting were developed.

The MSCs according to the present invention can achieve innovative improvements in stability and anticancer efficacy while minimizing side effects caused by a remarkable improvement in tumor targeting and simultaneously a remarkable increase in infectious virus particle/virus particle (IVP/VP) using MSCs as virus production factories with efficiencies comparable to existing virus-producing cell lines. That is, it is possible to simultaneously achieve the efficacy maximization and toxicity minimization of MSCs loaded with an oncolytic virus by solving the most difficult problems of virus-based anticancer drugs, such as tumorigenesis, tumor tropism, tumor migration ability, and control of virus production/release at an appropriate time point.

DESCRIPTION OF DRAWINGS

FIG. 1 shows the confirmation of TERT expression of human adipose MSC-TERT by western blotting.

FIG. 2 shows the confirmation of whether the passage extension of human adipose MSC-TERT is effective even at passage 30 by western blotting.

FIG. 3 shows the confirmation of the adenovirus infection ability of human adipose MSC-TERT by fluorescence microscopy.

FIG. 4 shows that the reductions in p53 accumulation and survival-related signals upon induction of E1B55K expression in human bone marrow and adipose MSCs occur, as confirmed by western blotting.

FIG. 5 shows the confirmation of an increase in p53 promoter activity by the expression of E1B55K in the presence of doxycycline by a Tet-One inducible expression system by luminescence intensity.

FIG. 6 shows that the increase in p53 promoter activity by E1B55K is decreased by E4orf6, as confirmed by luminescence intensity.

FIG. 7 shows that an E4orf6 gene in an adenoviral backbone d1324-BstB3 is amplified by PCR, transferred to a pFlag-CMV2 vector, and sequenced to confirm 100% matching.

FIG. 8 shows the insertion of an E1B55K gene into pCA14, which is an adenovirus shuttle vector, as confirmed by DNA electrophoresis.

FIG. 9 shows the confirmation of the E1B55K sequence of pCA14-E1B55K.

FIG. 10A confirms that E1B55K detection by a polyclonal antibody against E1B55K is normal.

FIG. 10B shows that the detection result of a replication-incompetent virus expressing purified E1B55K by MOI confirms that normal expression is achieved.

FIG. 11 shows the confirmation of the transfection of MSC-TERT with an E1B55K-expressing plasmid and the improvement in virus production during the infection of an oncolytic adenovirus by virus titration.

FIG. 12 shows the confirmation of the improvement in virus production according to the increase in MOI during the additional infection of an oncolytic adenovirus after infecting MSC-TERT with a replication-incompetent virus expressing purified E1B55K for each MOI by virus titration.

FIG. 13 illustrates the protocol for the Tet-One inducible expression system.

FIG. 14 illustrates PCR conditions during construction of pRetro-x-tetone-puro-E1B55K.

FIG. 15 shows the confirmation of a construct plasmid in which E1B55K is properly inserted into pRetro-x-Tetone by the in-fusion method of exogenous gene transfer.

FIG. 16 is a cleavage map of the pRetro-x-Tetone-puro-E1B55K vector used for construction.

FIG. 17 shows the confirmation of final introduction by sequence analysis of an E1B55K plasmid inserted into pRetro-x-Tetone.

FIG. 18 shows the confirmation of whether E1B55K, which is a gene inserted into pRetro-x-Tetone, is induced to be expressed as a protein by doxycycline.

FIG. 19 shows protein expression of E1B55K in pRetro-x-tetone-puro-E1B55K according to the amount of doxycycline during treatment with doxycycline.

FIG. 20 compares virus production with and without treatment with doxycycline after infection with an oncolytic adenovirus after transfection of human adipose MSC-TERT with pRetro-Tetone-E1B55K.

FIG. 21 shows the results of western blotting in which an MSC-TERT-tetoneE1B55K cell line is established from MSC-TERT.

FIG. 22 shows the results of confirming p53 accumulation by western blot in the presence of doxycycline (2.5 μg/ml) from the MSC-TERT-tetoneE1B55K cell line.

FIG. 23 confirms the possibility of removing the tumorigenesis of the MSC-TERIT-tetoneE1B55K cell line.

FIG. 24A confirms that the expression of all factors acting at each stage of MSC homing is increased by the increase in GRP78.

FIG. 24B shows the confirmation of an increase in the expression of GRP78 mRN-Aby introducing pcDNA3.1-GRP78 into human MSC-TERT in order to confirm that the expression of GRP78 is assured.

FIG. 25 shows the result of confirming whether a GRP78 gene is inserted into a pcDNA3.1-hygro vector [C: pcDNA3.1-hygro].

FIG. 26 shows that a liver cancer cell line is transfected with a plasmid obtained from a pcDNA3.1-GRP78 clone, and then an increase in protein expression of GRP78 is confirmed by western blotting to verify gene introduction.

FIG. 27 shows the result of analyzing the base sequence of the GRP78 gene introduced from a plasmid obtained from a pcDNA3.1-GRP78 clone.

FIG. 28 illustrates a cleavage map of an LNCXneo vector with increased restriction enzyme recognition sites in an LNCX vector.

FIG. 29 shows the results of screening plasmid clones in which the GRP78 gene is inserted into LNCXneo by restriction enzyme digestion.

FIG. 30 shows the results of screening GRP78-expressing clones by introducing a retrovirus expressing the GRP78 gene into an MSC-TERI cell line.

FIG. 31 shows the results of clearly confirming that an MSC-TERT-GRP78-arrival site gathers at tumor tissue sites without adsorption to other organs within a very short period of time.

FIG. 32 shows the results of confirming the tumor targeting verification (rapid and accurate targeting of tumors) of a final type of MSC-TERT-tetoneE1B55K-GRP78 whose gene transfer is completed in lung cancer (a), liver cancer (b), and pancreatic cancer (c) cell lines.

FIG. 33 shows the results of confirming the enhanced intratumoral infiltration of the final type MSC-TERT-tetoneE1B55K-GRP78 at 24 hours (a), 48 hours (b) and 72 hours (c) after injection.

FIG. 34 shows the expression of adenovirus-related proteins in tumor tissue in the presence of doxycycline when the final type MSC-TERT-tetoneE1B55K-GR-P78 is infected with oncolytic viruses.

FIG. 35 shows the results of establishing final type MSC-TERT-tetone E1B55K-GRP78 cell line clone 21, 24, 25 and 26 cell lines.

FIG. 36 shows the result of confirming that E1B55K induction by doxycycline in the final clone 21 is effectively and sufficiently induced without being leaked even at a very low concentration.

FIG. 37 shows the amount of virus produced when the final type MSC-TERT-tetoneE1B55K-GRP78 is infected with an oncolytic virus according to the presence of doxycycline or during expression of E4orf6.

FIG. 38 shows that the expression of tumor homing markers according to an increase in the passage of MSC-TERT is confirmed.

FIG. 39 shows the anti-tumor effect of MSC-TERT-tetoneE1B55K-GRP78 infected with an oncolytic adenovirus by confirming changes in tumor size in mice by a graph.

FIG. 40A confirms the anti-tumor effect of MSC-TERT-tetoneE1B55K-GRP78 infected with an oncolytic adenovirus by the change in size after removal of mouse tumors.

FIG. 40B shows the anti-tumor effect of MSC-TERT-tetoneE1B55K-GRP78 infected with an oncolytic adenovirus by confirming changes in tumor size in mice by photographs of mice.

FIG. 41 illustrates the ratio of virus adsorption to a tumor (A) and other organs [liver (B), lung (C), spleen (D), kidney (E) and heart (F)].

MODES OF THE INVENTION

Hereinafter, the present invention will be described in more detail.

The present invention includes mesenchymal stem cells for delivering an oncolytic virus into which a human glucose regulated protein 78 (GRP78) gene (GenBank_NM_005347) is introduced.

Further, the present invention provides mesenchymal stem cells for delivering an oncolytic virus with improved tumor-targeting ability by introducing the GIRP78 gene into mesenchymal stem cells used as a viral vector.

The GRP78 gene is a glucose regulated protein 78 gene, whose role of increasing cell infiltration by increasing cell motility is already known, and its gene sequence is as shown in GenBank NM_005347 SEQ NO. 1 (human). In the present invention, a tumor homing marker serves to improve tumor targeting ability.

[SEQ ID NO: 1]

```
atg aagctctccc tggtggccgc gatgctgctg ctgctcagcg cggcgcgggc cgaggaggag

gacaagaagg aggacgtggg cacggtggtc ggcatcgacc tggggaccac ctactcctgc gtcggcgtgt

tcaagaacgg ccgcgtggag atcatcgcca acgatcaggg caaccgcatc acgccgtcct atgtcgcctt

cactcctgaa ggggaacgtc tgattggcga tgccgccaag aaccagctca cctccaaccc cgagaacacg

gtctttgacg ccaagcggct catcggccgc acgtggaatg acccgtctgt gcagcaggac atcaagttct

tgccgttcaa ggtggttgaa aagaaaacta aaccatacat tcaagttgat attggaggtg ggcaaacaaa

gacatttgct cctgaagaaa tttctgccat ggttctcact aaaatgaaag aaaccgctga ggcttatttg

ggaaagaagg ttacccatgc agttgttact gtaccagcct attttaatga tgcccaacgc caagcaacca

aagacgctgg aactattgct ggcctaaatg ttatgaggat catcaacgag cctacggcag ctgctattgc

ttatggcctg gataagaggg agggggagaa gaacatcctg gtgtttgacc tgggtggcgg aaccttcgat
```

-continued gtgtctcttc tcaccattga caatggtgtc ttcgaagttg tggccactaa tggagatact catctgggtg gagaagactt tgaccagcgt gtcatggaac acttcatcaa actgtacaaa aagaagacgg gcaaagatgt caggaaagac aatagagctg tgcagaaact ccggcgcgag gtagaaaagg ccaaacgggc cctgtcttct cagcatcaag caagaattga aattgagtcc ttctatgaag gagaagactt ttctgagacc ctgactcggg ccaaatttga agagctcaac atggatctgt tccggtctac tatgaagccc gtccagaaag tgttggaaga ttctgatttg aagaagtctg atattgatga aattgttctt gttggtggct cgactcgaat tccaaagatt cagcaactgg ttaaagagtt cttcaatggc aaggaaccat cccgtggcat aaacccagat gaagctgtag cgtatggtgc tgctgtccag gctggtgtgc tctctggtga tcaagataca ggtgacctgg tactgcttga tgtatgtccc cttacacttg gtattgaaac tgtgggaggt gtcatgacca aactgattcc aaggaacaca gtggtgccta ccaagaagtc tcagatcttt tctacagctt ctgataatca accaactgtt acaatcaagg tctatgaagg tgaaagaccc ctgacaaaag acaatcatct tctgggtaca tttgatctga ctggaattcc tcctgctcct cgtggggtcc cacagattga agtcaccttt gagatagatg tgaatggtat tcttcgagtg acagctgaag acaagggtac agggaacaaa aataagatca caatcaccaa tgaccagaat cgcctgacac ctgaagaaat cgaaaggatg gttaatgatg ctgagaagtt tgctgaggaa gacaaaaagc tcaaggagcg cattgatact agaaatgagt tggaaagcta tgcctattct ctaaagaatc agattggaga taaagaaaag ctgggaggta aactttcctc tgaagataag gagaccatgg aaaaagctgt agaagaaaag attgaatggc tggaaagcca ccaagatgct gacattgaag acttcaaagc taagaagaag gaactggaag aaattgttca accaattatc agcaaactct atggaagtgc aggccctccc ccaactggtg aagaggatac agcagaaaaa gatgagttgt ag In the present invention, it was confirmed that the tumor tropism was improved by the GRP78 gene, and in particular, the virus was delivered to tumor tissue sites without adsorption to organs other than tumors.

Although the passage extension in the case of human mesenchymal stem cells in order to facilitate the introduction of such a specific gene is difficult, a telomerase reverse transcriptase (TERT) gene, which induces cell proliferation, may be additionally introduced to overcome this difficulty.

The TERT gene is a telomerase reverse transcriptase gene, and its gene sequence is as shown in GenBank NM_198253, SEQ ID NO: 2 (human).

[SEQ ID NO: 2]

atgccgcgcgc tccccgctgc cgagccgtgc gctccctgct gcgcagccac taccgcgagg tgctgccgct ggccacgttc gtgcggcgcc tggggcccca gggctggcgg ctggtgcagc gcggggaccc ggcggctttc cgcgcgctgg tggcccagtg cctggtgtgc gtgccctggg acgcacggcc gccccccgcc gccccctcct tccgccaggt gtcctgcctg aaggagctgg tggcccgagt gctgcagagg ctgtgcgagc gcggcgcgaa gaacgtgctg gccttcggct tcgcgctgct ggacggggcc cgcgggggcc cccccgaggc cttcaccacc agcgtgcgca gctacctgcc caacacggtg accgacgcac tgcgggggag cggggcgtgg gggctgctgc tgcgccgcgt gggcgacgac gtgctggttc acctgctggc acgctgcgcg ctctttgtgc tggtggctcc cagctgcgcc taccaggtgt gcgggccgcc gctgtaccag ctcggcgctg ccactcaggc ccggcccccg ccacacgcta gtggaccccg aaggcgtctg ggatgcgaac gggcctggaa ccatagcgtc agggaggccg gggtcccct gggcctgcca gccccgggtg cgaggaggcg cgggggcagt gccagccgaa gtctgccgtt gcccaagagg cccaggcgtg gcgctgcccc tgagccggag cggacgcccg ttgggcaggg gtcctgggcc cacccgggca ggacgcgtgg accgagtgac cgtggtttct gtgtggtgtc acctgccaga cccgccgaag aagccacctc tttggagggt gcgctctctg gcacgcgcca ctcccaccca tccgtgggcc gccagcacca cgcgggcccc ccatccacat cgcggccacc acgtccctgg gacacgcctt gtcccccggt gtacgccgag accaagcact tcctctactc ctcaggcgac aaggagcagc tgcggccctc cttcctactc agctctctga ggcccagcct gactggcgct cggaggctcg tggagaccat ctttctgggt tccaggccct -continued

```
ggatgccagg gactccccgc aggttgcccc gcctgcccca gcgctactgg caaatgcggc ccctgtttct
ggagctgctt gggaaccacg cgcagtgccc ctacggggtg ctcctcaaga cgcactgccc gctgcgagct
gcggtcaccc cagcagccgg tgtctgtgcc cgggagaagc ccccagggctc tgtggcggcc cccgaggagg
aggacacaga cccccgtcgc ctggtgcagc tgctccgcca gcacagcagc ccctggcagg tgtacggctt
cgtgcgggcc tgcctgcgcc ggctggtgcc cccaggcctc tggggctcca ggcacaacga acgccgcttc
ctcaggaaca ccaagaagtt catctccctg gggaagcatg ccaagctctc gctgcaggag ctgacgtgga
agatgagcgt gcgggactgc gcttggctgc gcaggagccc aggggttggc tgtgttccgg ccgcagagca
ccgtctgcgt gaggagatcc tggccaagtt cctgcactgg ctgatgagtg tgtacgtcgt cgagctgctc
aggtctttct tttatgtcac ggagaccacg tttcaaaaga acaggctctt tttctaccgg aagagtgtct ggagcaagtt
gcaaagcatt ggaatcagac agcacttgaa gagggtgcag ctgcgggagc tgtcggaagc agaggtcagg
cagcatcggg aagccaggcc cgccctgctg acgtccagac tccgcttcat ccccaagcct gacgggctgc
ggccgattgt gaacatggac tacgtcgtgg gagccagaac gttccgcaga gaaaagaggg ccgagcgtct
cacctcgagg gtgaaggcac tgttcagcgt gctcaactac gagcgggcgc ggcgccccgg cctcctgggc
gcctctgtgc tgggcctgga cgatatccac agggcctggc gcaccttcgt gctgcgtgtg cgggcccagg
acccgccgcc tgagctgtac tttgtcaagg tggatgtgac gggcgcgtac gacaccatcc cccaggacag
gctcacggag gtcatcgcca gcatcatcaa accccagaac acgtactgcg tgcgtcggta tgccgtggtc
cagaaggccg cccatgggca cgtccgcaag gccttcaaga gccacgtctc taccttgaca gacctccagc
cgtacatgcg acagttcgtg gctcacctgc aggagaccag cccgctgagg gatgccgtcg tcatcgagca
gagctcctcc ctgaatgagg ccagcagtgg cctcttcgac gtcttcctac gcttcatgtg ccaccacgcc
gtgcgcatca ggggcaagtc ctacgtccag tgccagggga tcccgcaggg ctccatcctc tccacgctgc
tctgcagcct gtgctacggc gacatggaga acaagctgtt tgcggggatt cggcgggacg ggctgctcct
gcgtttggtg gatgatttct tgttggtgac acctcacctc acccacgcga aaaccttcct caggaccctg
gtccgaggtg tccctgagta tggctgcgtg gtgaacttgc ggaagacagt ggtgaacttc cctgtagaag
acgaggccct gggtggcacg gcttttgttc agatgccggc ccacggccta ttcccctggt gcggcctgct
gctggatacc cggaccctgg aggtgcagag cgactactcc agctatgccc ggacctccat cagagccagt
ctcaccttca accgcggctt caaggctggg aggaacatgc gtcgcaaact ctttggggtc ttgcggctga
agtgtcacag cctgtttctg gatttgcagg tgaacagcct ccagacggtg tgcaccaaca tctacaagat
cctcctgctg caggcgtaca ggtttcacgc atgtgtgctg cagctcccat ttcatcagca agtttggaag
aaccccacat ttttcctgcg cgtcatctct gacacggcct ccctctgcta ctccatcctg aaagccaaga
acgcagggat gtcgctgggg gccaagggcg ccgccggccc tctgccctcc gaggccgtgc agtggctgtg
ccaccaagca ttcctgctca agctgactcg acaccgtgtc acctacgtgc cactcctggg gtcactcagg
acagcccaga cgcagctgag tcggaagctc ccggggacga cgctgactgc cctggaggcc gcagccaacc
cggcactgcc ctcagacttc aagaccatcc tggactga
```

In the present invention, an MSC-TERT-GRP78 cell line was established, and the improvement in the tumor targeting of mesenchymal stem cells for the proliferation of viral vectors and viruses was confirmed. Therefore, the mesenchymal stem cells may be used for both tumor diagnosis and treatment.

In addition, the present invention provides mesenchymal stem cells for delivering an oncolytic virus into which an E1B55K gene is introduced such that the expression thereof is induced by an expression inducer.

The E1B55K gene is a viral gene encoding the E1B55K protein that is expressed at the early stage in the life of an adenovirus. The gene sequence is as shown in GenBank AC_000008, SEQ ID NO: 3. (The underlined a in the first line was originally g, but the KpnI site is removed by substitution. The underlined t in the 14th line is one in which a was originally substituted with t to remove the HindIII site.)

[SEQ ID NO: 3]

```
atggagcgaaga aacccatctg agcggggagt acctgctgga ttttctggcc atgcatctgt
ggagagcggt tgtgagacac aagaatcgcc tgctactgtt gtcttccgtc cgcccggcga taataccgac
ggaggagcag cagcagcagc aggaggaagc caggcggcgg cggcaggagc agagcccatg gaacccgaga
gccggcctgg accctcggga atgaatgttg tacaggtggc tgaactgtat ccagaactga gacgcatttt
gacaattaca gaggatgggc aggggctaaa gggggtaaag agggagcggg ggcttgtga ggctacagag
gaggctagga atctagcttt tagcttaatg accagacacc gtcctgagtg tattactttt caacagatca aggataattg
cgctaatgag cttgatctgc tggcgcagaa gtattccata gagcagctga ccacttactg gctgcagcca
ggggatgatt ttgaggaggc tattagggta tatgcaaagg tggcacttag gccagattgc aagtacaaga
tcagcaaact tgtaaatatc aggaattgtt cctacatttc tgggaacggc gccgagctgg agatagatac
ggaggatagg gtggccttta gatgtagcat gataaatatg tggccggggg tgcttggcat ggacggggtg
gttattatga atgtaaggtt tactggcccc aattttagcg gtacggtttt cctggccaat accaacctta tcctacacgg
tgttagcttc tatgggttta acaatacctg tgtggaagcc tggaccgatg taagggttcg ggctgtgcc ttttactgct
gctggaaggg ggtggtgtgt cgccccaaaa gcagggcttc aattaagaaa tgcctctttg aaaggtgtac
cttgggtatc ctgtctgagg gtaactccag ggtgcgccac aatgtggcct ccgactgtgg ttgcttcatg
ctagtgaaaa gcgtggctgt gattaagcat aacatggtat gtggcaactg cgaggacagg gcctctcaga
tgctgacctg ctcggacggc aactgtcacc tgctgaagac cattcacgta gccagccact ctcgcaaggc
ctggccagtg tttgagcata acatactgac ccgctgttcc ttgcatttgg gtaacaggag gggggtgttc ctaccttacc
aatgcaattt gagtcacact aagatattgc ttgagcccga gagcatgtcc aaggtgaacc tgaacggggt
gtttgacatg accatgaaga tctggaaggt gctgaggtac gatgagaccc gcaccaggtg cagaccctgc
gagtgtggcg gtaaacatat taggaaccag cctgtgatgc tggatgtgac cgaggagctg aggcccgatc
acttggtgct ggcctgcacc cgcgctgagt ttggctctag cgatgaagat acagattga
```

The present inventors established a human MSC-CAR-E1B55K cell line from bone marrow-derived human MSCs that have already been filed (Patent Document 1), and confirmed an increase in virus production, but confirmed that passage extension was not easy and the condition of cell lines deteriorates as the passage number increased, and confirmed that animal experiments and master cell banking were impossible for this reason, and it took a lot of time to figure out the cause. In particular, a new function of E1B55K was confirmed. This is the fact that E1B55K not only induces an increase in viral proliferation, but also induces a decrease in viability of cell lines at the same time.

The increase in tumorigenic potential by the TERT gene, which was inevitably introduced for mass production of MSC cell lines, could provide a solution by determining, for the first time, that E1B55K induces not only an increase in viral replication, but also an overall decrease in viability of MSC cells. That is, the time difference induction of the expression time point of the E1B55K enabled the passage extension of MSCs, thereby enabling mass production through cell banking, and at the same time, fundamentally blocking the tumorigenesis of MSCs.

In the examples, the Tet-on system was applied in order to induce the expression time point of the E1B55K gene with a time difference, that is, to allow for expression after introduction of mesenchymal stem cells into the body, but any other time difference induction system is also possible. Furthermore, an expression inducer is preferably doxycycline, tetracycline, or the like.

In the present invention, an MSC-TERT-tetoneE1B55K cell line was established, and E1B55K was expressed (oncolysis) at desired time points through a time difference to fundamentally block the mass production of viruses and the tumorigenesis of MSCs.

Further, the present invention includes mesenchymal stem cells for delivering an oncolytic virus, including a glucose regulated protein 78 (GRP78) gene and an E1B55K, wherein the E1B55K is expressed by an expression inducer.

In the present invention, an MSC-TERT-tetoneE1B55K-GRP78 cell line was established, and it was confirmed that it is possible to control virus production and release timing such that tumor targeting can be improved and viruses can be mass-produced.

The mesenchymal stem cell line used in the present invention is preferably human-derived. The mesenchymal stem cell line is preferably derived from bone marrow, cord blood or fat.

The oncolytic virus used in the present invention may be an oncolytic adenovirus, an oncolytic adeno-associated virus (AAV), an oncolytic retrovirus, an oncolytic lentivirus, an oncolytic herpes simplex virus or an oncolytic vaccinia virus.

In addition, the oncolytic adenovirus may be an oncolytic adenovirus described in Korean Patent Application No. 2016-0166171 developed by the present inventors.

The present invention also includes a composition for delivering an anticancer gene, including the mesenchymal stem cells for delivering an oncolytic virus and the oncolytic virus.

The composition for delivering a gene of the present invention may be for systemic administration.

Stem cells (Ad-MSCs) loaded with the virus of the present invention, in addition to having cancer-specific characteristics, have a low or no immune response, and thus, can be systemically administered, and are highly targeted to tumor cells, have an effect of not inducing toxicity, and thus can remarkably enhance gene delivery efficiency.

The mesenchymal stem cells may be isolated from bone marrow, cord blood, fat, and the like, and allogeneic mesenchymal stem cells may be used using the patient's own or blood bank databases. Therefore, when the adenovirus-loaded stem cells of the present invention are used as a gene carrier, not only self-treatment but also allogeneic treatment is possible, so the unit cost of gene therapy may be further reduced.

Methods for introducing the adenovirus including the gene of the present invention into mesenchymal stem cells may be carried out by various methods known in the art. Specifically, the gene may be introduced by a virus infection method known in the art.

As used herein, the term "anticancer pharmaceutical composition" refers to a "pharmaceutical composition for use in treating cancer".

Since the mesenchymal stem cells included as an active ingredient in the anticancer pharmaceutical composition of the present invention are the same as the mesenchymal stem cells of the present invention described above, the detailed description on mesenchymal stem cells is equally applied to the compositions of the present invention. Therefore, the description on common matters is omitted to avoid undue complication due to unnecessary repeated descriptions of the present specification.

Since the oncolytic adenovirus included in the compositions of the present invention exhibits killing efficacy against various tumor cells as described above, the pharmaceutical composition of the present invention may be used for the treatment of cancer such as gastric cancer, lung cancer, breast cancer, ovarian cancer, liver cancer, bronchial cancer, nasopharyngeal cancer, laryngeal cancer, pancreatic cancer, biliary tract cancer, bladder cancer, colorectal cancer, colon cancer, cervical cancer, brain cancer, prostate cancer, bone cancer, head and neck cancer, skin cancer, kidney cancer, polyploid carcinoma, thyroid cancer, parathyroid cancer or ureteral cancer. As used herein, the term "treatment" includes: (i) prevention of tumor cell formation; (ii) inhibition of tumor-related diseases or disorders upon removal of tumor cells; and (iii) relief of tumor-related diseases or disorders upon removal of tumor cells. Therefore, as used herein, the term "therapeutically effective amount" refers to an amount sufficient to achieve the aforementioned pharmacological effect.

A pharmaceutically acceptable carrier included in the composition of the present invention is a pharmaceutically acceptable carrier typically used in formulation, and includes lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like, but is not limited thereto.

The pharmaceutical composition of the present invention may additionally include a lubricant, a wetting agent, a sweetening agent, a flavoring agent, an emulsifier, a suspending agent, a preservative, and the like, in addition to the aforementioned ingredients.

The pharmaceutical composition of the present invention is preferably parenterally administered, and may be administered, for example, using intravenous administration, intraperitoneal administration, intramuscular administration, subcutaneous administration or topical administration. The pharmaceutical composition of the present invention is administered intraperitoneally to treat ovarian cancer and administered through the hepatic portal vein to treat liver cancer, by an injection method, and in the case of liver cancer, melanoma and breast cancer, the pharmaceutical composition may be administered by direct injection into a tumor mass, and in the case of colon cancer, the pharmaceutical composition may be administered by direct injection into an enema, and in the case of bladder cancer, the pharmaceutical composition may be administered by direct injection into a catheter.

A suitable administration amount of the pharmaceutical composition of the present invention may vary depending on factors, such as formulation method, administration method, age, body weight, sex or disease condition of a patient, diet, administration time, administration route, excretion rate and response sensitivity, and a doctor with ordinary skill may readily determine and prescribe an effective dosage for a desired treatment. In general, the pharmaceutical composition of the present invention includes $1\times10^5$ to $1\times10^{15}$ pfu/ml of oncolytic virus, and typically, the amount of virus that infects MSCs (based on $1\times10^6$ cells) at one injection is $1\times10^7$ to $1\times10^8$ pfu.

The pharmaceutical composition of the present invention may be prepared in the form of a unit dose or by being contained in a multi-dose container by being formulated using a pharmaceutically acceptable carrier and/or excipient according to a method that can be readily implemented by a person with ordinary skill in the art to which the present invention pertains. In this case, the formulation may also be in the form of a solution in an oil or aqueous medium, a suspension or in the form of an emulsion, an extract, a powder, a granule, a tablet or a capsule, and the pharmaceutical composition of the present invention may additionally include a dispersant or a stabilizer.

The pharmaceutical composition of the present invention may be used as a single therapy, but may also be used in combination with a common type of chemotherapy or radiation therapy, and when such combination therapy is implemented, cancer may be more effectively treated. A chemotherapeutic agent that can be used together with the composition of the present invention includes gemcitabine, sorafenib, cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin, methotrexate, and the like. A radiation therapy that can be used together with the composition of the present invention includes X-ray radiation, γ-ray radiation, and the like.

The mesenchymal stem cells according to the present invention may exhibit anticancer effects against gastric cancer, lung cancer, breast cancer, ovarian cancer, liver cancer, bronchial cancer, nasopharyngeal cancer, laryngeal cancer, pancreatic cancer, biliary tract cancer, bladder cancer, colorectal cancer, colon cancer, cervical cancer, brain cancer, prostate cancer, bone cancer, head and neck cancer, skin cancer, kidney cancer, polyploid carcinoma, thyroid cancer, parathyroid cancer or ureteral cancer.

Furthermore, the present invention may include a composition for diagnosing cancer, including a virus/stem cell complex including the mesenchymal stem cells and the oncolytic virus.

As used herein, the term "diagnosis" means confirming the presence or characteristics of the pathological state. Diagnosis in the present invention is to confirm the presence or absence of cancer and its progression.

The virus/stem cell complex refers to a stem cell infected or loaded with a virus.

The virus/stem cell complex may be combined with a luminescent material, a fluorophore, or an isotope to diagnose cancer through imaging.

The luminescent material refers to any material that emits light.

In the examples of the present invention, it was confirmed that after MSCs were infected with a luciferase-expressing adenovirus, luminescence was captured as images by intraperitoneally administering luciferin to mice.

The fluorophore is preferably a phosphor, a fluorescent protein, or other imaging materials capable of binding to the peptide that specifically binds to NRP1, but is not limited thereto.

The fluorophore is preferably fluorescein, BODYPY, tertramethylrhodamine, Alexa, Cyanine, allopicocyanine or derivatives thereof, but is not limited thereto.

The fluorescent protein is preferably Dronpa protein, fluorescent chromogenic gene (EGFP), red fluorescent protein (DsRFP), Cy5.5, which is a cyanine fluorophore exhibiting near-infrared fluorescence, or other fluorescent proteins, but is not limited thereto. Other imaging materials are preferably iron oxide, radioactive isotopes, and the like, but are not limited thereto, and may be applied to imaging equipment such as MR and PET.

The present invention also includes a method for treating cancer, the method including: administering a therapeutically effective amount of a pharmaceutical composition including the mesenchymal stem cells and the oncolytic virus to a subject.

All of the above-described contents in relation to the method for treating cancer can be applied to the above-described mesenchymal stem cells of the present invention and the composition including the same as they are or applied correspondingly.

The cancer may be specifically gastric cancer, lung cancer, breast cancer, ovarian cancer, liver cancer, bronchial cancer, nasopharyngeal cancer, laryngeal cancer, pancreatic cancer, biliary tract cancer, bladder cancer, colorectal cancer, colon cancer, cervical cancer, brain cancer, prostate cancer, bone cancer, head and neck cancer, skin cancer, kidney cancer, polyploid carcinoma, thyroid cancer, parathyroid cancer or ureteral cancer, but is not limited thereto.

As used herein, the term "subject" refers to a mammal that is the subject of treatment, observation or experimentation, preferably a human.

As used herein, the term "therapeutically effective amount" refers to an amount of active ingredient or pharmaceutical composition which induces a biological or medical response in a tissue system, animal or human considered by a researcher, veterinarian, physician or other clinicians, and this includes an amount that induces alleviation of the symptoms of a disease or disorder being treated. It is obvious to those skilled in the art that the therapeutically effective amount and frequency of administration of the active ingredient of the present invention will vary according to the desired effect. Therefore, the optimal dosage to be administered can be easily determined by those skilled in the art, and the range thereof varies according to the type of disease, the severity of disease, the content of active ingredient and other ingredients contained in the composition, the type of formulation, the body weight, age, sex, health condition, and diet of a patient, the administration time, the administration method, the excretion rate, and the like. In the treatment method of the present invention, $1\times10^5$ to $1\times10^{15}$ pfu/ml of oncolytic virus is included, and typically, the amount of virus that infects MSCs (based on $1\times10^6$ cells) at one injection is $1\times10^7$ to $1\times10^8$ pfu.

In the treatment method of the present invention, the pharmaceutical composition of the present invention may be administered orally or parenterally (for example, applied intravenously, subcutaneously, intraperitoneally or topically) according to the desired method.

MODE FOR INVENTION

Hereinafter, the present invention will be described in more detail through the Examples according to the present invention, but the scope of the present invention is not limited by the Examples suggested below.

EXAMPLES

Reference Example 1: Construction of Human Oncolytic Adenovirus YSC-02

YSC-02 was constructed as described in Preparation Example 19 of Korean Patent Application No. 2016-0166171.

Reference Example 2: Construction of Human Oncolytic Adenovirus Dl324-3484-H1-shHSP27-U6-shTGFβ1 dl324-3484-H1-shHSP27-U6-shTGFβ1 was constructed as described in Preparation Example 9 of Korean Patent Application No. 2016-0166171.

Preparation Example 1: Introduction of TERT Gene for Mass Production of MSC Cell Line 1) Confirmation of Human Adipose MSC-TERT Single Clone Expression A TERT gene was introduced to induce the expression of a specific gene that overcomes the short supply and lifespan of MSCs. In the case of human MSCs, passage extension is not easy. To overcome this problem, a telomerase reverse transcriptase (TERT) gene, which induces cell proliferation, was inserted and clones highly expressing TERT were selected.

The method for introducing the TERT gene is as follows.

A retrovirus vector pBABE-hygro-hTERT was purchased from Addgene, and cell clones resistant to 200 μg/ml hygromycin B Gold were obtained by infecting human adipose MSCs with a filtered medium obtained by transfecting platinum-A packaging cells (Cell Biolabs) with 1 μg of the retrovirus vector pBABE-hygro-hTERT, and then screened and selected as in FIG. 1. MSC clone 22 was finally selected, and clone 22 was used for human adipose MSC-TERT used in subsequent experiments.

2) Confirmation of Passage Extension

FIG. 2 confirms the passage extension of hum an MSCs, which was proliferated to 30 passages. It was confirmed that the increase in expression level of TERT from the MSCs extensively passaged to 30 passages was still very clearly increased and the expression of other MSC-related major markers was also maintained or increased compared to the wild type.

3) Confirmation of Adenovirus Infection Ability

A TERT-expressing MSC clone (No. 22) was infected with a replication-incompetent adenovirus expressing red fluorescence protein (RFP) at 20 MOI and 100 MOI, and 48 hours later, fluorescence-stained cells were observed under a fluorescence microscope. As a result of comparison with a wild type MSC, which is a control, it was confirmed that the infection rate of human MSC-TERT was improved compared to the control, and at least a two-fold increase in infection rate at (20 MOI) and a 90% or more infection rate at 100 MOI were met (FIG. 3).

Example 1: Confirmation of New Function of Adenoviral Gene E1B55K

When MSCs are to be used as a cell line for clinical mass production, master cell banking needs to be conducted. For this purpose, it is essential that the passage extension of MSCs be possible above all else. However, on the other hand, a principle that extension induction must not contribute to an increase in turmorigenic potential also needs to be maintained. Although the dilemma of simultaneously satisfying these two conditions was considered impossible at first, a solution was suggested for the first time in the present inventor's laboratory while constructing a stable MSC cell line in which CAR and E1B55K genes were introduced into MSCs. A human MSC-CAR-E1B55K cell line was established from bone marrow-derived human MSCs that had been filed, and an increased virus production was confirmed [Patent Document 1]. However, it was confirmed several times that passage extension was not easy and the condition of the cell line deteriorated as the passage number increased. Accordingly, it was confirmed that in the case of animal experiments, master cell banking was impossible, and as a result of finding out the cause, it was confirmed that E1B55K induces increased viral proliferation and reduced viability of cell lines at the same time (FIG. 4). That is, it was confirmed that not only p53, which is well known as a tumor suppressor gene and a cytostatic factor, is distinctly accumulated, but also the expression of factors associated with cell survival (HSP27, HSP70, Daxx, phospho-p65, NF-κB, c-Me) was decreased by E1B55K.

The experimental process for this is as follows.

First, E155K was cloned into pcDNA3.1 hygro (+). To extract an E1B55K gene from pBSK-3484 including the E1B55K gene, after PCR (initial denaturing: 95° C. for 2 minutes, denaturing: 95° C. for 30 seconds, annealing: 58° C. for 30 seconds, extension: 72° C. for 2 minutes; 30 cycles) and BamHI/NotI digestion with primers each having BamHI and NotI (forward, 5'-GCGGATCCATG-GAGCGAAGAAACCCATICT-3: SEQ ID NO: 4, reverse, 5'-GAG CGGCCGCTCAATCTGTATCTTCATCGCT-3': SEQ ID NO: 5), a plasmid was constructed by introducing the E1B55K into pcDNA3.1 hygro (+) (Invitrogen), which had been previously digested with BanHI/NotI.

It was confirmed by transfecting the plasmid expressing E1B55K into bone marrow-derived MSCs and adipose-derived MSCs that the cell line long-term expression of E1B55K reduced the viability of the cell line. That is, the accumulation of p53 and the reduction of various survival-related signals were observed.

In order to confirm how the accumulation of p53, reduction of cell survival signals and induction of cell death were caused by E1B55K expression, the following assumption was made. That is, it was known that E1B55K maintains cell survival by well-known p53 degradation in the related art only through a complex with an E4orf6 protein. Therefore, a hypothesis was made, in which when the expression of E1B55K alone is induced in MSC cells, (stoichiometrically) free E1B55K alone acts as a transcriptional activator that promotes p53 transcription to reduce cell viability due to the quantitative comparative advantage of E1B55K over E4orf6, and experiments were carried out as follows.

After the MSC-TERT-tetoneE1B55K cell line was co-transfected with 1 μg of pFlag-CMV2-E4orf6 subcloned with a pGL2-p53 promoter (pGL2-356 bp, Addgene) constructed such that a constant portion (−344 to +12) of the p53 promoter was positioned in front of a site where a luciferase coding gene was inserted and the E4orf6 gene or 1 μg of pFlag-CMV2 (Sigma) as a control, luciferase activity with and without doxycycline (1.25 μg/ml for 48 hours) was confirmed by luminescence intensity.

The analytical method used in this case was a Dual-Luciferase Reporter Assay System from Promnega (catalog number #E1910, FIG. 5).

E1B55K, whose expression was induced in the MSC-TERT-tetoneE1B55K cell line by doxycycline treatment, was directly or indirectly bound to the p53 promoter to activate transcription, resulting in a 4-fold increase in luminescence intensity due to luciferase activity (FIG. 5). Conversely, it was confirmed that when the expression of E4orf6 occurred as in E1B55K-expressing MSCs, the increase in luminescence intensity did not exceed 1.5-fold. These results show that E4orf6 interferes with the action of E1B55K alone due to the formation of a complex with E1B55K, and at the same time, more actively fulfills its already known role in promoting the degradation of the p53 protein (FIG. 6).

Here, subcloning of the E4orf6 (GenBank AC 000008; also called E434K) gene was performed to transfer the E4orf6 gene from an adenoviral backbone d1324-BstBI into a pFlag-CM V2 vector. For this purpose, an E4orf6 coding gene site was amplified by PCR (initial denaturing: 95° C. for 2 minutes, denaturing: 95° C. for 30 seconds, annealing: 58° C. for 30 seconds, extension: 72° C. for 1 minute and 30 seconds; 30 cycles) in dl324-BstBI using a primer for E4orf6 PCR (forward 5'-GTACAAGCTTATGACTAC GTCCGGCGTTCC-3' including HindIII: SEQ ID NO: 6 and reverse 5'-CACCTCTAGACTA-CATGGGGGTAGAGTCAT-3' including XbaI: SEQ ID NO: 7), and then doubly digested with HindIII/XbaI and ligated to pFlag-C MV2 digested with HindIII and XbaI. 100% matching was confirmed by performing sequencing using CMV30, one of the universal primers from Cosmo-genetech Co. Ltd., to confirm whether subcloning was properly performed (FIG. 7).

From the above experimental results, the induction of overexpression of E1B55K acts directly or indirectly on the p53 promoter, which is contrary to the main action of E1B55K in adenovirus wild type (forms a complex with E4orf6 to induce degradation of p53 protein), so a new action that induces the accumulation of p53 was discovered through transcriptional induction. In addition, in order to confirm how the increase in MSC cell death and the decrease in viability signal depending on the increase in expression of E1B55K affect the virus production ability in MSCs, it was intended to again confirm whether the virus production ability in MSCs increased by externally supplying E1B55K using an adenoviral vector. For this purpose, a replication-incompetent adenovirus expressing E1B55K was constructed as follows.

1) Construction of Replication-Incompetent Adenovirus (pCA14-E1B55K) Expressing E1B55K The E1B55K was cloned into pCA14 which is an adenovirus shuttle vector. E1B55K was included in pBSK-3484, and a primer including XbaI and HindIII at both ends thereof (sense 5-TTCAICTAGAATGGAGCGAAGAAACCCATC-3' (XbaI): SEQ LD NO: 9, antisense 5'-GiACGAAGCTTT-CAATCTGTATCTTCATCGC-3 (HindIII): SEQ ID NO: 10) was constructed and amplified by PCR (initial denaturing: 95° C. for 2 minutes, denaturing: 95° C. for 30 seconds, annealing: 58° C. for 30 seconds, extension: 72° C. for 2 minutes; 30 cycles) and ligated into pCA14 (Microbix, Canada) digested in advance with XbaI/HindIII. As a result, it was confirmed that all E11355K PCR fragments were inserted into PCA14 (FIG. 8). A confirmed adenoviral shuttle vector, pCA14-E1B55K, was linearized again with XmnI digestion after sequence confirmation (FIG. 9), an adenoviral vector, dl324-BstBI, was linearized with Bsp119I digestion, these two were cotransformed into *E. coli* 13.15183 to induce homologous recombination to construct an adenoviral vector expressing E1B55K, and then the vector was transfected into 293A, and then virus production was induced to expand production, and after isolation and purification, the titer was calculated.

It was confirmed that 1, 2, and 3 out of pc14-E1B55K plasmid clones 1, 2, 3, and 4 read in the forward and reverse directions with a primer dedicated to pCA14 sequence analysis (self-constructed forward (hCMV): 5'-GGG AGGTCTATATAAGCAGAGCTCG-3': SEQ ID NO: 11, reverse (pCA14 SV40): 5-CATGATCGATGCTAG ACGATCCAGA-3: SEQ ID NO: 12) matched, and here, FIG. 9 shows the results of sequence analysis of sample #3 clone plasmid DNA In the forward non-matching two (red) sequences shown in FIG. 9, the first base of E1B55K of the existing wild adenovirus type 5, a, is the 2019$^{th}$ base of AC_000008 in GenBank, and the 2048$^{th}$ base, g, in the forward primer was intentionally substituted with a to remove a KpnI site (GGTACC→AGTACC) and the 2084$^{th}$ base, a, in the forward primer (overlapped with red of the reverse primer) was substituted with t to intentionally remove a HindIII site (AAGCTT→TAGCTT) (100% homology).

2) Confirmation of E1B55K Expression in MSC Lysate Infected with Virus Expressing E1B55K After it was confirmed that the detection of E1B55K by a polyclonal antibody secured by commissioning the construction of a specific antibody against E1B55K for E1B55K expression was not abnormal (FIG. 10A), and as a result of detecting the produced and purified virus at each MOI, normal expression was confirmed by western blotting (FIG. 10B). The drawing on the right side of FIG. 10A is attached as raw data for the drawing on the left side in order to confirm the correct size and band of a polyclonal antibody E1B55K. In Lane 3 of FIG. 10A, 3 μg of adenoviral vector (d1324-E1B55K) DNA expressing E11B55K was digested with Pact, then transfected into 293A, and after confirmation of virus production, human adipocyte-derived MSC-TERT was infected with the harvested soup, in Lane 4, a final soup was infected by freezing and thawing the soup and plus cells obtained in the same manner as Lane 3, and in Lane 5, the starting amount of DNA during the first transfection is 2.5 μg. In FIG. 10B, it was confirmed that the polyclonal antibody against E1B55K is working normally by confirming that after a viral soup obtained tinder the conditions of Lane 5 was amplified and purified, the intensity of a band corresponding to E1B55K is also increasing as the MOI increases when MSC-TERT is infected with a virus expressing the replication-incompetent E1B55K at each MOI by calculating virus infectivity particles.

The process of constructing a polyclonal antibody specific to E1B55K is as follows.

First, a peptide sequence located at the N-terminal site of E1B55K (MERRNPSERGVPAGFSGHASVESGC: SEQ ID NO: 13) was synthesized, bovine serum albumin (BSA) was conjugated to an immunogen carrier, and then New Zealand White rabbits were immunized and serum was purified to obtain the polyclonal antibody (GW Vitek, Korea).

3) Comparison of Virus Production According to E1B55K Expression Level in Human Adipose MSC-TERT→Validation of Innovative Expansion of Virus Production Ability of MSCs According to Gene Transfer First, human adipocyte-derived MSC-TERT was transfected with 1 μg of an E1B55K-expressing plasmid (pcDNA3.1-E1B55K) (FIG. 11) or infected with a replication-incompetent adenovirus expressing E1B55K at each MOI (FIG. 12), then the medium was replaced after 4 hours. And after infection with an oncolytic adenovirus (YSC-02) at 100 MOI, all of the medium and cells were harvested 48 hours later, and then frozen and thawed to excite the virus as much as possible, and then the results of performing the titration of an infectious virus in a supernatant obtained by centrifugation are shown. As a result, it was confirmed that virus production was clearly increased compared to the control after infection with the oncolytic adenovirus in the E1B55K-expressing MSC-TERT (FIG. 12).

Example 2: Innovative Viral Production Increase Induction, Regulation of Expression Time Point of Loaded Gene, and Intrinsic Tumorigenesis Control Technique can be Simultaneously Realized by Introducing Time-Difference Expression Regulation System of E1B55K The increase in control of tumorigenic potential by the TERT gene, which was inevitably introduced for mass production of MSC cell lines, could provide a solution by determining, for the first time, that E1B55K induces not only an increase in viral replication, but also an overall decrease in viability of MSC cells. That is, a control technique, in which the time difference induction of the expression time point of the E1B55K gene enabled the passage extension of MSCs, thereby enabling mass production through cell banking, and at the same time, fundamentally blocking the tumorigenesis of MSCs, was developed. It is of great significance that this has provided an innovative turning point for virus/MSC therapeutic agents.

The protocol in FIG. 13 was referenced for the Retro-X™Tet-One™ induced expression system (TAKARA cat #634307).

1) Construction of pRetro-X-Tet-one-puro-E1B55K

In order to insert the E1B55K gene into a Retro-X-Tet-one-purovector plasmid, both ends need to have EcoRI and BamHI recognition sites, respectively pCA14-E1B55K was used as a template for the construction of E1B55K having recognition sites, an E1B55K In-fusion EcoRI sense primer is 5'-CCCTCGTAAAGAATTCATG-GAGCGAAGAAACCCATCTGAG-3' (SEQ ID NO: 14), and an E1B55K In-fusion BamHI antisense primer is 5'-GAGGTGGTCTGGATCCTCAATCTGTATCTT-CATCGCTAGA-3' (SEQ ID NO: 15).

PCR conditions are as follows (FIG. 14).

After initial denaturing at 95° C. for 2 minutes, 30 cycles of denaturing at 95° C. for 40 seconds, annealing at 61° C. for 40 seconds, and extension at 72° C. for 1 minute and 50 seconds were performed.

A Promega (#M750B) product was used to perform PCR.

After a construct plasmid (sample pRetro-X-Tetone-E1B55K #13 in FIG. 15), in which E1B55K was properly inserted into pRetro-X-Tetone by the in-fusion method of exogenous gene introduction, was secured, the introduction was finally confirmed by performing sequence analysis (FIG. 17). Next, it was confirmed whether the expression of the E1B55K protein, which is an actually inserted gene, was induced by doxycycline (FIG. 18). As in Lane 5 in FIG. 18, it was confirmed that the expression of E1B55K was induced when A549 was transfected with the pRetro-X-Tetone-E1B55K plasmid only in the presence of doxycycline (2.5 μg/ml), and the expression of E1B55K was not induced when A549 was transfected with the same plasmid in the absence of doxycycline. That is, no leakage phenomenon occurred. The rightmost lane is a positive condition under which E1B55K was constitutively expressed and thus E1B55K expression was confirmed.

The pRetro-X-tetone-puro-E1B55K vector used for construction is shown in FIG. 16.

2) Confirmation of pRetro-X-Tetone-Puro-E1B55K Expression

After transfection with the pRetro-X-Tetone-puro-E1B55K plasmid, the expression of E1B55K was confirmed in pRetro-X-tetone-puro-E1B55K according to the amount of doxycycline during treatment with doxycycline. When a tet one system was introduced to investigate whether the time difference expression regulation of E1B55K could be controlled with the tet one system, it was confirmed that no E1B55K expression occurred at all before the treatment with doxycycline (FIG. 19). That is, it was confirmed that no leakage occurs. Conversely, even treatment with a very low concentration of 0.05 μg/ml of doxycycline immediately induced the expression of E1B55K. This means that cell survival can be maintained before treatment with doxycycline and expression can be induced immediately after treatment with doxycycline after reaching tumors.

The time difference virus release was secondarily verified as follows.

After human adipose MSC-TERT was transfected with a pRetro-tetone-E1B55K plasmid (4 hours) and then infected with an oncolytic adenovirus expressing a red florescence protein (REP) (4 hours), virus production was compared with and without treatment with doxycycline 48 hours later.

As a result, it was confirmed that viral production was clearly increased 10-fold or more upon treatment with doxycycline (FIG. 20).

3) Establishment of MSC-TERT-tetoneE1B55K Cell Line

After a gene encoding E1B55K, which is an early region 1B-55 kDa of an adenovirus, was introduced into a Retro-X-Tet-One inducible expression system (TAKARA Bio Inc.), MSC-TERT was infected with the same to secure clones expressing E1B55K in the presence of doxycycline. For this purpose, GP2-293 packaging cells were co-transfected with pRetroX-TetOne-E1B55K and a pAmpho vector encoding the membrane protein (included in the TAKRA kit). After 48 hours, MSC-TERT, which is a target cell, was infected with the filtered retroviral supernatant. All clones selected with puromycin during the culture process were subjected to western blotting again to confirm that the induction of E1B55K expression (FIG. 21) and p53 accumulation (FIG. 22) proceeded simultaneously in the presence of doxycycline (2.5 μg/ml).

These results indicated that the induction of viral production could be increased at desired time points by regulating the expression time point of E1B55K, which is a loaded gene, according to the treatment with doxycycline. (Since the gene expression of E1B55K must be induced, the virus appears to begin to increase at least 24 hours after treatment with doxycycline.)

4) Realization of Intrinsic Tumorigenesis Control Technique

It was confirmed whether clone 2 or 10 in FIG. 21 could control tumorigenesis. For this purpose, long-term (about 14 days) culture was performed after 6-wells in which cloned cell lines were aliquoted were treated with doxycycline.

As a result, it was confirmed that after 2 weeks of culture with doxycycline treatment (1.25 μg/ml), most of the cells lost their viability (1.25 μg/ml) (FIG. 23). Accordingly, even for uninfected MSCs other than by lysis caused by infection with an oncolytic virus, the used cell lines infected and selected by the E1B55K-expressing retrovirus eventually leads to cell death, thereby fundamentally ruling out the possibility of tumorigenesis.

Example 3: Establishment of Innovative Increase in Tumor Targeting—Discovery of Tumor Homing Improvement Factor By inducing the additional expression of GRP78 in human adipose MSC-TERT, the expression of tumor tropism-related markers was confirmed.

It was confirmed that the expression of all factors acting at each stage of MSC homing is increased by the increase in GRP78 (FIG. 24A).

In order to confirm that GRP7S was certainly expressed, an increase in mRNA expression of GRP78 was confirmed by transfecting human MSC-TERT with pcDNA3.1-GRP78 (2 μg) (FIG. 24B).

1) GRP78 Cloning into pcDNA3.1 Hygro (+)

RNA was extracted from SNU449, a liver cancer cell line with a high expression level of GRP78, with Trizol. The extracted RNA was reverse transcribed using SuperScript™ First-Strand Synthesis System for RT-PCR kit from Invirogen. The primers used to perform PCR were then sequenced by adding an XhoI site in the forward direction and an XbaI site in the reverse direction. PCR (initial denaturing: 95° C. for 2 minutes; denaturing: 95° C. for 40 seconds; annealing: 58° C. for 40 seconds; extension: 72° C. for 2 minutes and 30 seconds; 30 cycles) cloning was performed using Forward (5'-GATTCTCGAGATGAAGCTCTCCCTGG-3': SEQ ID NO: 16) and Reverse (5'-GGCCTCTAGACTACAATCATCTTTT-3': SEQ 11) NO: 17) primers. After PCR and digestion with XhoI/XbaI, the backbone pcDNA3.1-hygro vector was also digested with XhoI/XbaI and ligated. Colonies obtained after transformation into bacteria were cultured. Each of the plasmids thus obtained was digested simultaneously with XhoI/XbaI to confirm a size-matched insertion only in plasmid 5 by confirming insertion (FIG. 25). After transfection of a liver cancer cell line SNU449 with No. 5 pcDNA3.1-GRP78, an increase in protein expression of GRP78 was confirmed by western blotting (FIG. 26). Also, sequence analysis of the sample 5 plasmid showed 100% homology with NCBINM_005347 (FIG. 27).

2) GRP78 Cloning into PLNCX Neo

The following procedure was performed to introduce the (GRP78 gene into MSC-TERT or MSC-TERT-tetonE1B55K.

In order to introduce GRP78 into a retroviral vector pLNCXneo, a pcDNA3.1-GRP78 vector was digested with XhoI/PmeI to extract a GRP78 site, and the GRP78 site was ligated and inserted into PLNCXneo previously digested with XhoI/PmeI.

pLNCX neo was originally constructed by increasing the restriction enzyme recognition site from HindIII-HpaI-ClaI, which is a cloning site in existing LNCX, to HindIII-PmlI-BstXI-NotI-XhoI-SalI-ApaI-PmeI-HpaI-ClaI (FIG. 28).

In this case, a strand sequence is as follows.

```
Top
                                         (SEQ ID NO: 18)
5'-AGCTTCACGTGCCAGCACAGTGGCGGCCGCTCGAGTCGACGGGCCC
GTTTAAACGTTAACAT-3',

Bottom
                                         (SEQ ID NO: 19)
5'-CGATGTTAACGTTTAAACGGGCCCGTCGACTCGAGCGGCCGCCACT
GTGCTGGCACGTGA-3.
```

To confirm whether LNCXneo-GRP78 was inserted, pLNCXneo (control) and pcDNA3.1-GRP78 (GRUP78 gene-providing plasmid) as controls were digested with HindIII/PmeI, respectively, and the GRP78 fragments derived from linearized PLNTCXneo and pcDNA3.1-GRP78 were ligated and transformed into DH5u competent cells, and then it was confirmed that pLNCXneo-GRP78 candidate constructs (Samples 1 to 24) were cleaved at the same time and inserted into Samples 2, 5, 9, 11, 12, 20 and 21 by obtaining plasmids (FIG. 29).

3) Construction of MSC-TERT-GRP78 Cell Line

Platinum-A packaging cells (Cell Biolabs) were transfected with a retroviral vector pLNCXneo-GRP78, and after 48 hours, the medium was filtered. Cell clones resistant to G418 (500 μg to 600 μg/ml) were obtained by infecting MSC-TERT with a medium solution containing the retrovirus obtained by filtration, and then screened to select clones 2 and 4 clearly expressing GRP78 and MMP2 (FIG. 30).

4) Tumor Targeting of MSCs with Gene Transfer: Confirmation of Conditions to Specifically Reach Only the Tumor Site within Very Short Period of Time ① (Verification of tumor targeting of MSC-TERT-GRP78

$2\times10^6$ SNU398 cells (a liver cancer cell line) were subcutaneously transplanted into the shoulder regions of 6-week-old BALB/c thymic nude mice, and 7 days later, $1\times10^6$ MSC-TERT-GRP78 cells infected with a replication-incompetent adenovirus expressing firefly luciferase were injected into the tail veins. 150 mg of D-luciferin per kg of mouse was injected intraperitoneally into the mice in order to use an in vivo imaging system (IVIS) device that recognizes luminescence. The biodistribution of MSC-TERT-GRP78 infected with an adenovirus expressing luciferase in vivo was observed 6 hours after injection into the tail vein by imaging using an IVIS Spectrum System (PerkinElmer). A feature of this experiment is that MSC-TERT-GRP78 with GRP78 gene transfer is allowed to form tumors in the shoulder to distinguish them from internal organs such as the liver and lungs in order to accurately distinguish how much tumor migration ability the MSC-TERT-GRP78 has, clearly confirming that the arrival sites of MSC-TERT-GRP78 gathered at tumor tissue sites within a very short time without adsorption to other organs (FIG. 31).

② Verification of Tumor Targeting of Gene-Transferred Final Type MSC-TERT-tetoneE1B55K-GRP78

$8\times100^6$ A549 cells (a lung cancer cell line), $2\times10^6$ SNU398 cells (a liver cancer cell line) or $2\times10^6$ MiaPaCa-2 cells (a pancreatic cancer cell line) were subcutaneously transplanted into the shoulder regions of 6-week-old BALB/c thymic nude mice, and 7 days later, $1\times10^6$ MSC-TERT-tetoneE1B55K-GRP78 cells infected with a replication-incompetent adenovirus expressing firefly luciferase were injected into the tail veins. 150 mg of D-luciferin per kg of mouse was injected intraperitoneally into the mice in order to use an IVIS device that recognizes luminescence. The biodistribution of MSCs infected with an adenovirus expressing luciferase in vivo was observed 6 hours or 24 hours later using the IVIS Spectrum System (PerkinElmer).

As a result, similarly to the previous targeting experiment T, tumors were formed on the shoulder side in order to distinguish them from internal organs such as the liver and lungs, thereby clearly confirming that the arrival sites of MSC gathered at tumor tissue sites within a very short time without adsorption to other organs (FIG. 32). As can be seen here, it can be observed that a final type of MSC-TERT-tetoneE1B55K-GRP78 including GRP78 migrated to the tumor site within a very short time, as compared to MSCs without GRP78, regardless of cancer type, and it can be confirmed that there is a certain intensity difference when compared to the luciferase activity intensity values (minimally 10-fold up to maximally 100-fold depending on the luminescence intensity in tumors). This shows that tumor targeting occurs very quickly and accurately. Here, E1B55K is not expressed because the diet does not include doxycycline.

Such surprisingly rapid and accurate trafficking of luciferase-expressing MSC-GRP7S to tumors and targeting to various tumor types greatly enhances the possibility of utilizing MSC-GRP78 for tumor diagnosis. In a primary mouse model, solid cancer was artificially transplanted subcutaneously, and the tumor site was confirmed by allowing MSC-GRP7S to migrate, but when there is a tumor in the same manner as in the primary mouse model, even in a metastatic model present in the body, MSC-GRP78 can be delivered to the tumor site to emit light, or tumors can be detected by labeling the tumors with a higher resolution isotope. This can be applied to tumor diagnosis, and it will be possible to construct an OV/MSC complex simultaneously capable of tumor diagnosis and treatment in the long term.

③ Confirmation of Infiltration of Gene-Transferred Final Type MSC-TERT-tetoneE1B55K-GRP78 into Tumors It was confirmed that the final type of MSC-TERT-tetoneE1B55K-GRP78 reached tumor sites, and the following experiment was performed to confirm whether the MSCs that actually reached the tumor sites infiltrated into tumor tissue.

First, A549 cells were transplanted into the subcutaneous tissue of mice to form tumors. Then, the final type of MSC cells (MSC-TERT-tetoneE1B55K-GRP78) was labeled with a fluorescent cell tracker probe (Invitrogen, C34565) and then injected into the mouse tail vein. At 24 hours, 48 hours and 72 hours after the injection, the tumor tissue was removed and tissue-sectioned, and then the fluorescent site was confirmed under a fluorescence microscope. As shown in FIG. 33, it could be confirmed that an excessively large number of MSCs with GRP78 were present in the tumor. In the case of MSCs lacking GRP78, it was observed that the MSCs remained predominantly at the tumor interface with low fluorescence intensity.

④ Confirmation of Expression of Adenovirus-Related Proteins in Tumor Tissue

Viruses were released from MSC-TERT-tetoneE1B55K-GRP78 that had infiltrated into tumor tissue to infect tumor cells, and the following experiments were performed to confirm whether the virus was replicated and maintained for a certain period of time after virus production.

$8\times10^6$ A549 cells (a lung cancer cell line) were subcutaneously transplanted into the flank regions of 6-week-old BALD/c thymic nude mice, and $1\times10^6$ MSC-TERT-tetoneE1B55K-GRP78 cells infected with an oncolytic adenovirus expressing shHSP27-shTGFβ were injected into the tail veins of each of every 2 mice whose tumor size reached an average of 150 $mm^3$. Then, 3 days later, $1\times10^6$ MSC-TERT-tetoneE1B55K-GRP7S cells infected with an oncolytic adenovirus expressing shHSP27-shTGFβ1 were additionally injected. Then, 7 days after the second injection, tumors were removed from the mice in each group, and tumor-sectioned samples were reacted with an adenovirus type 5-specific antibody (Abeam, Cambridge, UK) to perform a DAB coloring reaction with a secondary antibody, and control staining for immunohistochemistry was performed with hematoxylin nuclear stain. In this case, a diet containing doxycycline (625 mg/kg) as feed was fed to all groups.

As a result, adenovirus-specific proteins were confirmed in most confirmed areas (FIG. 34). An adenovirus was released from MSCs in the tumor tissue until at least 7 days after tail vein injection, indicating that replication, proliferation and spreading occurred repeatedly and confirming the possibility that the virus remained until around 20 days, when the size of the tumor had decreased to a level of almost zero.

5) Establishment of Human Adipose MSC-TERT-tetoneE1B55K-GRP78 Cell Line—Confirmation of E1B55K Expression after 1.25 μg/mL Doxycycline Treatment for 48 Hours After infection with a retroviral soup obtained by co-transfecting GP2-293 packaging cells with pRetroX-TetOne-E1B55K and a pAmpho vector encoding a membrane protein, puromycin selection (0.8 μg/ml to 1.0 μg/ml) was performed, and after infection with a retroviral soup obtained by transfecting platinum-A packaging cells again with a retroviral vector pLNCXneo-GRP7S, G418 selection (500 μg/ml to 600 μg/ml) was performed, and final clones with clear E1B55K and M1P2 protein expression were selected in the presence of doxycycline (1.25 μg/ml) (FIG. 35, final clones 21, 24, 25, and 26).

In final clone 21, it is shown that the E1B55K induction concentration by doxycycline was effectively and sufficiently induced without any leakage even at a very low concentration, less than 1/10 of the 1.25 μg/ml used (FIG. 36). This suggests that it can be reliably turned on/off in vivo and thus viral production can be induced at desired time points because it is not greatly affected by the treatment amount of doxycycline, which is an expression inducer in vivo, and responds very sensitively to the presence or absence of doxycycline.

For the ability of human adipose MSC-TERT-tetoneE1B55K-GRP78 (Clone 21) to produce viruses, after infection with an oncolytic adenovirus expressing shHSP27/shTGFβ1, the increased rate of virus production was confirmed after 48 hours in MSCs during treatment with doxycycline (1.25 μg/ml), and in this case, the difference in virus production according to the expression of the E4orf6 gene was also confirmed. For this experiment, Clone 21 MSCs were transfected with 1 μg of pFlag-CMV2-E4orf6 in which the E4orf6 gene was subcloned or 1 ag of pFlag-CMV2 as a control, and after additional infection with an oncolytic adenovirus expressing shHSP27/shTGFβ1, the cells were treated with doxycycline (1.25 μg/ml for 48 hours), and then the total amount of virus in the harvested soup and remaining cells was determined by titration. As a result, in final clone 21, a nearly 10-fold increase in virus production upon treatment with doxycycline was confirmed, and differences in virus production were observed depending on the presence or absence of transfection with the E4orf6 gene (FIG. 37). That is, the amount of virus production was decreased according to the E4orf6 external expression induction. This seems that an increase in virus production by the action of E1B55K alone acts as a virus production inhibitory factor caused by complex formation by E4ORF6. (It was confirmed that induction of cell death process of MSCs by E11355K alone contributes to virus production. The E1B55K/E4orf6 complex interferes with the cell death of MSCs, resulting in missing the optimal time for virus production.)

6) Comparison of Efficacy Maintenance in Human Adipose MSC-TERT Low Passage and High Passage It is essential to confirm that MSC efficacy is maintained during mass production of 200 vials or more of master cell bank cell lines. That is, it was confirmed, by western blotting, from samples in which each cell acquired at low passage (p13) and high passage (p23) was lysed whether biomarkers known as markers related to tumor homing, which is an MSC characteristic caused by differences in passage of final MSC-TERT-tetoneE1B55K-GRP78, were maintained.

As a result, it was confirmed that even when the passage was increased to 20, there was no difference in the expression of proteins known as a tumor homing marker (FIG. 38).

Example 4: Anticancer Efficacy of MSC-TERT-tetoneE1B55K-GRP78 Infected with Oncolytic Adenovirus $8\times10^6$ A549 cells (a lung cancer cell line) were subcutaneously transplanted into the flanks of 6-weeks-old BALB/c thymic nude mice, and mice with tumors reaching an average size of 150 $mm^3$ were divided into groups of 10 mice each. $1\times10^6$ MSC-TERT-tetoneE1B55K-GRP78 cells infected with an oncolytic adenovirus expressing sh-SP27-shTGFβ1 were injected into the mouse tail veins. Then, 3 days later, $1\times10^6$ MSC-TERT-tetoneE1B55K-GRP78 cells infected with an oncolytic adenovirus expressing shHSP27-shTGFTβ1 were additionally injected intravenously. As a control, a group transplanted with tumor cells alone (no treat) and a group injected with the final MSC-TERT-tetoneE1B55K-GRP78 (MSC only) were used. In this case, a diet containing doxycycline (625 mg/kg) as feed was fed to all groups.

As a result, it was observed that when an antitumor effect obtained by direct intratumoral injection of the oncolytic virus (Ad-3484-shHSP27-shTGFβ1) (a state in which the growth rate of the tumor size was delayed compared to the control, but the tumor size itself decreased and thus did not regress) was compared, the tumor size was significantly reduced and the tumor almost disappeared within a few days when an oncolytic virus (Ad-3484-shHSβ27-shTGFβ1) in the final MSC-TERT-tetoneE1B55K-GRP78 was injected into the tail veins compared to untreated tumors or the control in which the final type of MSC alone was injected into the tail vein as observed in FIG. 39, and it could be seen that for 20 days after injection, the tumors almost disappeared, and then tumors were again grew slightly in several individuals. Through individual photographs of mice in each group and photographs of tumors taken for each group after removal of tumors one month after the first injection of OV/MSC, the antitumor effect of the oncolytic virus (Ad- 3484-shHSP27-shTGFβ1) was confirmed more reliably in the final MSC-TERT-tetoneE1B55K-GRP78 (FIG. 40).

Example 5: Confirmation of Adsorption to Organs Other than Tumors

After it was confirmed that tumor targeting occurs very efficiently, the copy number of adenoviral genes was measured for each time period for the amount of adenovirus in each major organ including tumors in order to confirm the amount captured in major organs other than tumors (lungs, liver, spleen, and the like), the migration to the tumor site, the elapsed time, and the like in more detail. The viral genomic plasmid DNA was defined as standard known DNA, and confirmed by drawing a standard curve (in the case of the viral DNA of the currently used oncolytic adenovirus, 1 copy is 10 μg).

For this purpose, after infection with a replication-incompetent defective E1B55K virus, a single dose of MSC-TERT-GRP78 ($1\times10^6$) infected with the YSC-02 oncolytic virus of Reference Example 1 was administered IV through the tail once, and samples were collected by date (day 0, 1, 2, 3, 4, 5, 10, and 15). The collected tissues (tumors, lungs, liver, spleen, kidneys, heart) were immediately stored in liquid nitrogen, and on the day when tissue sampling was completed, genomic DNA was extracted from each tissue under the same conditions. To confirm whether the gene was expressed using the extracted genomic DNA, real-time PCR was performed using primers for the E40RF gene. The primers for screening E40RF used at this time are as follows.

```
Forward
                                        SEQ ID NO: 20
5'-CGTGGTCAAACT CTACAGCC-3':

Reverse
                                        SEQ ID NO: 21
5'-GCATGAGCATGACTACGATG-3':
```

As can be seen in FIG. 41, although the variation between individuals is severe, it can be seen that the range in individual tissues when the oncolytic virus enters the tumor tissue is $10^4$ to $10^{10}$ copies, and almost all viruses are adsorbed and absorbed in tumor tissue compared to several to 10 copies found in all other organs.

The invention claimed is:

1. A mesenchymal stem cell for delivering an oncolytic virus, having improved tumor-targeting ability, wherein a glucose regulated protein 78 (GRP78) gene is introduced into the mesenchymal stem cell, wherein the mesenchymal stem cell is loaded with an oncolytic virus, and wherein the mesenchymal stem cell expresses a GRP78 protein for improving tumor-targeting ability.

2. A mesenchymal stem cell for delivering an oncolytic virus, wherein an E1B55K gene is introduced into the mesenchymal stem cell such that the expression thereof is induced in the presence of an inducible expression system comprising doxycycline or tetracycline, and wherein the E1B55K gene is expressed after the mesenchymal stem cell is introduced into a body.

3. A mesenchymal stem cell for delivering an oncolytic virus, comprising a glucose regulated protein 78 (GRP78) gene and an E1B55K gene, wherein the GRP78 gene and the E1B55K gene are introduced into the mesenchymal stem cell, and wherein the E1B55K gene is expressed by an expression inducer after the mesenchymal stem cell is introduced into a body.

4. The mesenchymal stem cells of claim 1, wherein the oncolytic virus is an oncolytic adenovirus, an oncolytic adeno-associated virus (AAV), an oncolytic retrovirus, an oncolytic lentivirus, an oncolytic herpes simplex virus or an oncolytic vaccinia virus.

5. The mesenchymal stem cells of claim 3, wherein the expression inducer is doxycycline or tetracycline.

6. The mesenchymal stem cells of claim 1, wherein the mesenchymal stem cells are derived from cord blood, bone marrow or fat.

7. A composition for delivering an anticancer gene, comprising the mesenchymal stem cell of claim 1, wherein the mesenchymal stem cell is loaded with an oncolytic virus comprising the anticancer gene.

8. An anticancer pharmaceutical composition comprising the mesenchymal stem cell of claim 1, wherein the mesenchymal stem cell is loaded with an oncolytic virus.

9. A method for treating cancer, the method comprising administering, to a subject, a therapeutically effective amount of a pharmaceutical composition comprising the mesenchymal stem cell of claim 1, wherein the mesenchymal stem cell is loaded with an oncolytic virus.

* * * * *